(12) United States Patent
Luo

(10) Patent No.: US 8,871,726 B2
(45) Date of Patent: Oct. 28, 2014

(54) C-ARYL GLUCOSIDE DERIVATIVE, PREPARATION METHOD THEREFOR, AND USE THEREOF

(75) Inventor: Huibing Luo, Shanghai (CN)

(73) Assignee: Shanghai Allist Pharmaceuticals, Inc., Shanghai (CN)

( * ) Notice: Subject to any disclaimer, the term of this patent is extended or adjusted under 35 U.S.C. 154(b) by 0 days.

(21) Appl. No.: 13/881,939

(22) PCT Filed: Oct. 27, 2011

(86) PCT No.: PCT/CN2011/001794
§ 371 (c)(1),
(2), (4) Date: May 15, 2013

(87) PCT Pub. No.: WO2012/055169
PCT Pub. Date: May 3, 2012

(65) Prior Publication Data
US 2013/0225514 A1 Aug. 29, 2013

(30) Foreign Application Priority Data

Oct. 27, 2010 (CN) .......................... 2010 1 0523465

(51) Int. Cl.
| | |
|---|---|
| *A61K 31/70* | (2006.01) |
| *C07H 17/02* | (2006.01) |
| *C07H 15/24* | (2006.01) |
| *C07H 15/14* | (2006.01) |
| *C07D 409/10* | (2006.01) |
| *C07D 409/14* | (2006.01) |

(52) U.S. Cl.
CPC .............. *C07H 15/14* (2013.01); *C07D 409/10* (2013.01); *C07D 409/14* (2013.01)
USPC ............................ 514/24; 536/17.6; 536/18.1

(58) Field of Classification Search
None
See application file for complete search history.

(56) References Cited

FOREIGN PATENT DOCUMENTS

| WO | 98/31697 | 7/1998 |
|---|---|---|
| WO | 01/27128 A1 | 4/2001 |
| WO | 03/099836 A1 | 12/2003 |
| WO | WO2005/012326 | * 2/2005 |
| WO | WO2005012326 A1 | 2/2005 |
| WO | WO2008042688 A2 | 4/2008 |

OTHER PUBLICATIONS

International Search Report dated Feb. 2, 2012, issued in corresponding International Application No. PCT/CN2011/001794.
Ehrenkranz J.R.L. et al., "Phlorizin: A Review", Diabetes/Metabolism Research and Reviews 21:31-38 (2005).
Han S. et al., "Dapagliflozin, a Selective SGLT2 Inhibitor, Improves Glucose Homeostatis in Normal and Diabetic Rats", Diabetes 57:1723-1729 (Jun. 2008).
Nomura S. et al., "Discovery of Canagliflozin, a Novel C-Glucoside with Thiophene Ring, as Sodium-Dependent Glucose Contransporter 2 Inhibitor for the Treatment of Type 2 Diabetes Mellitus", Journal of Medicinal Chemistry 53:6355-6360 (2010).
Rossetti L. et al., "Correction of Hyperglycemia with Phlorizin Normalizes Tissue Sensitivity to Insulin in Diabetic Rats", The Journal of Clinical Investigation 79:1510-1515 (May 1987).
Rossetti L. et al., Effect of Chronic Hyperglycemia on In Vivo Insulin Secretion in Partially Pancreatectomized Rats, The Journal of Clinical Investigation 80:1037-1044 (Oct. 1987).
Extended Supplementary European Search Report dated Jan. 23, 2014 received from related Application No. 11835443.0.

* cited by examiner

*Primary Examiner* — Traviss C McIntosh, III
(74) *Attorney, Agent, or Firm* — Scully, Scott, Murphy & Presser, P.C.

(57) ABSTRACT

The present invention relates to a C-aryl glucoside derivative of Formula (I) below, a preparation method therefor and a use thereof, wherein X, $R^1$, $R^2$, $R^3$, $R^4$, m and n are as defined in specification. The derivative of the present invention is a sodium-glucose co-transporter 2 (SGLT-2) inhibitor associated with glucose reabsorption of bowel or kidney, and has a good urine glucose excreting effect, thus being useful as a therapeutic agent for treating diabetes and related diseases.

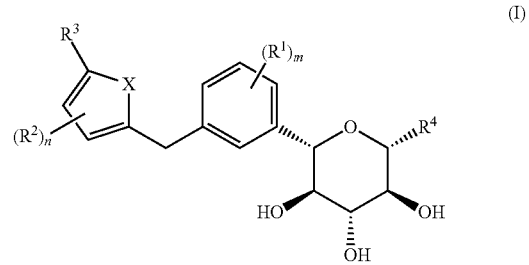

(I)

14 Claims, 1 Drawing Sheet

C-ARYL GLUCOSIDE DERIVATIVE, PREPARATION METHOD THEREFOR, AND USE THEREOF

TECHNICAL FIELD

The present invention relates to a C-aryl glucoside derivative that inhibits the activity of the sodium-dependent glucose cotransporter 2 (SGLT-2) relevant to the intestinal or renal glucose reabsorption, a preparation method therefor, a pharmaceutical composition containing said derivative, and a use thereof in treating diabetes mellitus and the related diseases.

BACKGROUND OF THE INVENTION

The incidence of diabetes mellitus (diabetes) is rising years by years. This disease seriously harms the health of human being. In the patients having diabetes mellitus, most of them are the type II (i.e. noninsulin-dependent) diabetic patient, who is characterized by the insulin resistance. The hyperglycemia is a sign of the type II diabetes mellitus, and is considered as a major risk factor for forming a complication of diabetes mellitus. Currently, the clinically-used anti-diabetic drug mainly includes dimethyl biguanides, sulfonyl ureas, and insulin sensitivity enhancers. Dimethyl biguanides and sulfonyl ureas occasionally show the side-effects such as lactic acidosis and hypoglycemia. Insulin sensitivity enhancers occasionally show the side-effects such as edema and obesity. The newly marketed anti-diabetic drugs include the drugs such as thiazolidinediones and α-glucosidase inhibitors. These drugs have good therapeutic effects, but still have the safe problem if administered for a long term. Therefore, in order to solve these problems, there is a need to develop the anti-diabetic drug having a new action mechanism.

Sodium-dependent glucose cotransporter (SGLT) is a new target that is discovered recently and used for treating diabetes mellitus. It can be divided into two sub-types, SGLT-1 and SGLT-2. SGLT-2 is a protein composed of 672 amino acids and containing 14 transmembrane segments; and is mainly expressed in the first 51 segments of the proximal renal tubule. SGLT-1 is distributed in small intestine, heart and kidney. SGLT-2 absorbs 90% of glucose in the primary urine. Only 10% of glucose is recycled to the body by the SGLT-1 absorption. It is promising for the selective inhibition of SGLT-2 to normalize the glucose in the blood plasma by increasing the urine glucose excretion, so as to increase the insulin sensitivity and retard the development of the complication of diabetes mellitus. Because the SGLT-2 inhibitor is not involved in the glucose metabolism, therefore it can be used as the supplementary means for the main method of controlling the blood glucose. Therefore, it is urgently desired to develop an anti-diabetic drug that has a strong inhibitory activity on SGLT-2 and has the new action mechanism. It is believed that this drug may reduce or prevent obesity while it promotes the excretion of the excessive glucose through the urine and therefore reduce the accumulation of glucose in the body.

A study shows that a glucose derivative, phlorizine, which is separated from nature substance and has a structure as shown below, may hinder the re-absorption of the excessive glucose in the kidney, promote the excretion of the glucose, and have an effect of reducing the blood glucose (Rossetti, L., et al. J. Clin. Invest., Vol. 80, page 1037, 1987; Vol. 79, page 1510, 1987). By modifying the structure of phlorizine, the related analogues can be divided into O-carbocyclic glycoside derivative, O-heterocyclic glycoside derivative, C-carbocyclic glycoside derivative, C-heterocyclic glycoside derivative, N-glycoside derivative, and the like. As a specific inhibitor for SGLT-2, phlorizine or the above closely related analogues can promote the excretion of the glucose but have no side effect of low blood glucose. They can inhibit the glucose re-uptaking in the experiment with dogs suffering from diabetes mellitus, and therefore cause the glucose level in the plasma to normalize.

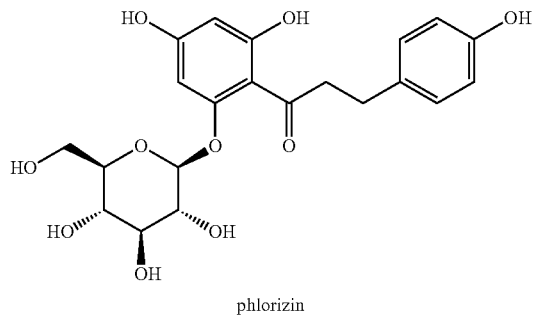 [SMILES: O=C(CCc1ccc(O)cc1)c1c(O)cc(O)cc1O[C@@H]1O[C@H](CO)[C@@H](O)[C@H](O)[C@H]1O]

phlorizin

It is reported that upon the oral administration of O-carbocyclic glycoside derivative or O-heterocyclic glycoside derivative, the glucoside bond is hydrolyzed by the β-glycosidase present in the small intestine, and there is a poor absorption efficiency for the glycoside derivative in its original form (Ehrenkranz, J. R., Lewis, N. G., Kahn, C. R. & Roth, J. Phlorizin: a review. Diabetes Metab. Res. Revs. 21, 31-38 (2005)).

WO 01/27128 (Bristol-Myers Squibb) discloses a compound represented by the following structure:

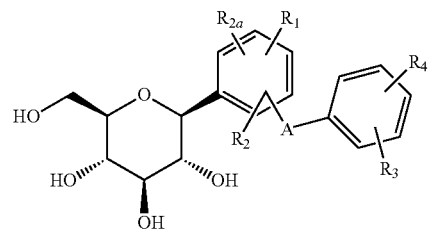

wherein A is O, S, NH or $(CH_2)_n$, n is 0-3; $R_1$, $R_2$ and $R_{2a}$ are independently H, OH, alkyl, $CF_3$, $OCHF_2$, $OCF_3$, halogen or the like; $R_3$ and $R_4$ are independently H, OH, O-aryl, $OCH_2$-aryl, alkyl, cycloalkyl, $CF_3$, —$OCHF_2$, —$OCF_3$, halogen, or like. It is reported that these compounds are the inhibitors of the SGLT-2 transport protein, and therefore represent an approach for treating diabetes mellitus and its complications.

WO 2003/099836 (Bristol-Myers Squibb) further discloses a SGLT-2 inhibiting compound, which has a structure as shown below and is subsequently named as dapagliflozin:

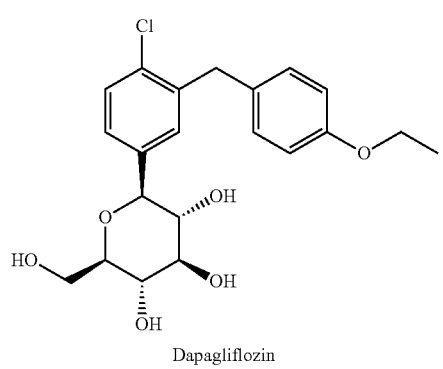 [SMILES: CCOc1ccc(Cc2cc([C@@H]3O[C@H](CO)[C@@H](O)[C@H](O)[C@H]3O)ccc2Cl)cc1]

Dapagliflozin

This application teaches a method of treating diabetes mellitus and the related diseases by administering a SGLT-2 inhibitory amount of the above compound alone or in combination with other anti-diabetic agents or other therapeutic agents. It is also reported that Dapagliflozin is a SGLT-2 inhibitor having a good selectivity, and has an $IC_{50}$ value on the human SGLT-2 of 1.12 nM and an $IC_{50}$ value on the human SGLT-1 of 1391 nM (Diabetes 57:1723-1729, 2008). Dapagliflozin is now in the stage III clinical trial, and has an effect of regulating the glucosuria, controlling the blood glucose and reducing the body weight. Its side effect mainly includes the hypoglycemia and the vaginal infection.

WO 98/31697 discloses a compound represented by the following structure:

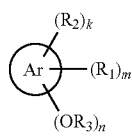

wherein Ar can be an aryl having 6-18 carbon atoms, including phenyl, biphenyl, diphenylmethane, diphenylethane and diphenylether, and $R_1$ is glycoside, $R_2$ is H, OH, amino, halogen, carboxyl, alkyl, cycloalkyl or the like, $R_3$ is hydrogen, alkyl or acyl, and each of k, m and n is independently 1-4. It is said that the disclosed compound can be used to treat or prevent inflammatory diseases, autoimmune diseases, infections, cancer and cancer metastasis, reperfusion disorders, thrombosis, ulcer, wounds and osteoporosis.

WO 2005/012326 discloses a compound represented by the following structure:

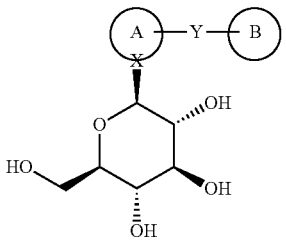

wherein Ring A and Ring B can be: Ring A is an optionally substituted benzene ring; and Ring B is an optionally substituted unsaturated monocyclic heterocyclic ring or an optionally substituted unsaturated fused heterobicyclic ring; X is a carbon atom or a nitrogen atom; Y is —$(CH_2)_n$—, wherein n is 1 or 2. The compound disclosed in this PCT application comprises a compound with the following structure:

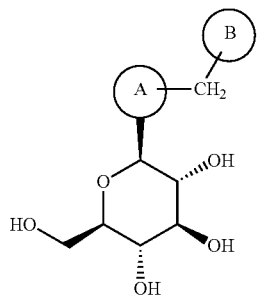

wherein Ring A is an optionally substituted benzene ring; and Ring B is an optionally substituted unsaturated monocyclic heterocyclic ring or an optionally substituted unsaturated fused heterobicyclic ring. It is said that the disclosed compound can be used as the SGLT-2 inhibitor. This application further discloses a SGLT-2 inhibiting compound, which has the following structure:

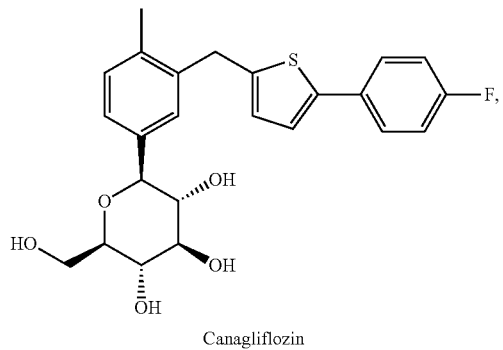 [SMILES: Cc1ccc([C@@H]2O[C@H](CO)[C@@H](O)[C@H](O)[C@H]2O)cc1Cc1ccc(-c2ccc(F)cc2)s1]

Canagliflozin and subsequently named as Canagliflozin. It is also reported that Canagliflozin has an $IC_{50}$ value on the human SGLT-2 of 2.2 nM and an $IC_{50}$ value on the human SGLT-1 of 910 nM (J. Med. Chem., 2010, 53, 6355-6360), and can remarkably increase the urine glucose level by inhibiting SGLT-2 so as to accomplish the treatment effect. Canagliflozin has a high oral bioavailability, and can effectively improve the glucose level in the patient and reduce the body weight. It is indicated by the research data that those diabetic patients, who got less therapeutic effect by treating with dimethyl biguanide (Metformin) alone, have got better therapeutic effect by treating with Canagliflozin and Metformin in combination, which is benefited from the action mechanism of the drug inhibiting SGLT-2.

WO 2008/042688 discloses a compound represented by the following structure:

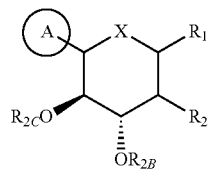

wherein A is optionally substituted aryl, cycloalkyl or heterocycle; X is O, S or $NR_3$; when X is O, $R_1$ is $OR_{1A}$, $SR_{1A}$, $SOR_{1A}$, $SO_2R_{1A}$ or $N(R_{1A})_2$; when X is S, $R_1$ is hydrogen, $OR_{1A}$, $SR_{1A}$, $SOR_{1A}$ or $SO_2R_{1A}$; when X is $NR_3$, $R_1$ is $OR_{1A}$, $SR_{1A}$, $SOR_{1A}$, $SO_2R_{1A}$, or $R_{1A}$; wherein each $R_{1A}$ is independently hydrogen or optionally substituted alkyl, aryl or heterocycle; $R_2$ is fluoro or $OR_{2A}$; each of $R_{2A}$, $R_{2B}$ and $R_{2C}$ is independently hydrogen, or optionally substituted alkyl, C(O)alkyl, C(O)aryl or aryl; $R_3$ is hydrogen, $C(O)R_{3A}$, $CO_2R_{3A}$, $CON(R_{3B})_2$, or optionally substituted alkyl, aryl or heterocycle; each $R_{3A}$ is independently optionally substituted alkyl or aryl; and each $R_{3B}$ is independently hydrogen or optionally substituted alkyl or aryl. The compound disclosed in this application comprises a compound with the following structure:

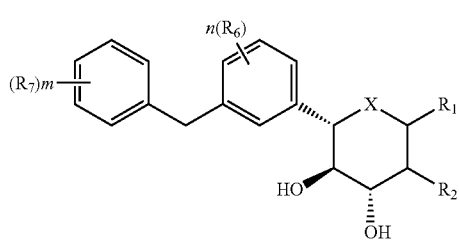

Wherein each of $R_6$ and $R_2$ is independently hydrogen, hydroxyl, halogen, amino, nitro, C $CR_{6A}$, $OR_{6A}$, $SR_{6A}$, $SOR_{6A}$, $SO_2R_{6A}$, $C(O)R_{6A}$, $CO_2R_{6A}$, $CO_2H$, $CON(R_{6A})(R_{6A})$, $CONH(R_{6A})$, $CONH_2$, $NHC(O)R_{6A}$, $NHSO_2R_{6A}$, or optionally substituted alkyl, aryl or heterocycle; wherein $R_{6A}$ is optionally substituted alkyl, aryl or heterocycle; m is 1-3; and n is 1-3. It is said that the disclosed compound can be used to treat diabetes mellitus and obesity.

In summary, it is a hotspot in the current anti-diabetic research to seek for a specific SGLT-2 inhibitor with a high efficiency and a low toxicity.

SUMMARY OF THE INVENTION

The present invention provides a compound represented by the following general formula (I):

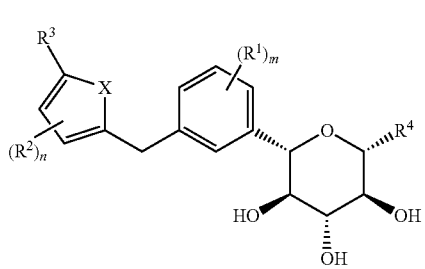

wherein:
X is O or S;
each of $R^1$ and $R^2$ is independently hydrogen, —OH, —SH, —NH$_2$, —NO$_2$, —CN, —COH, —COOH, —CONH$_2$, halogen, $C_1$-$C_4$alkyl, —O—$C_1$-$C_4$alkyl, —S—$C_1$-$C_4$alkyl, —SO—$C_1$-$C_4$alkyl, —SO$_2$—$C_1$-$C_4$alkyl, —CO—$C_1$-$C_4$alkyl, —CO$_2$—$C_1$-$C_4$alkyl, —CONH—$C_1$-$C_4$alkyl, —CC—$C_1$-$C_4$alkyl, —NHSO$_2$—$C_1$-$C_4$alkyl, —NHCO—$C_1$-$C_4$alkyl or —$C_3$-$C_6$cycloalkyl;
$R^3$ is hydrogen, —OH, —SH, —NH$_2$, —NO$_2$, —CN, —COH, —COOH, —CONH$_2$, halogen, —$C_1$-$C_4$alkyl, —O—$C_1$-$C_4$alkyl, —S—$C_1$-$C_4$alkyl, —CO—$C_1$-$C_4$alkyl, —CO$_2$—$C_1$-$C_4$alkyl, —CONH—$C_1$-$C_4$alkyl, an aryl having 1-3 substituents selected from the groups in Group A, a heteroaryl having 1-3 substituents selected from the groups in Group A, a $C_3$-$C_3$cycloalkyl having 1-3 substituents selected from the groups in Group A, a nitrogen-containing saturated heterocyclic group having 1-3 substituents selected from the groups in Group A or a nitrogen-containing partially unsaturated heterocyclic group having 1-3 substituents selected from the groups in Group A,
wherein, the group in Group A is selected from the group consisting of: hydrogen, halogen, —OH, —SH, —NH$_2$, —NO$_2$, —CN, —COH, —COOH, —CONH$_2$, $C_1$-$C_4$alkyl, —O—$C_1$-$C_4$alkyl, —NH—$C_1$-$C_4$alkyl, —S—$C_1$-$C_4$alkyl, —SO$_2$—$C_1$-$C_4$alkyl, —CO—$C_1$-$C_4$alkyl, —CO$_2$—$C_1$-$C_4$alkyl, —CONH—$C_1$-$C_4$alkyl, —CONH—$C_3$-$C_6$cycloalkyl, —$C_1$-$C_4$alkyl—OH, -aryl, —O-aryl, —NH-aryl, —S-aryl, —SO$_2$-aryl, —CO-aryl, —CO$_2$-aryl, —CONH-aryl, -cycloalkyl, heteroaryl, -a nitrogen-containing saturated heterocyclic group, —$C_1$-$C_4$alkyl-a nitrogen-containing saturated heterocyclic group and -a nitrogen-containing partially unsaturated heterocyclic group;
$R^4$ is —O—$R^5$, —S—$R^5$, —SO—$R^5$, —SO$_2$—$R^5$, $R^5$ is —$C_1$-$C_4$alkyl or —$C_3$-$C_8$cycloalkyl;
m is 1, 2 or 3; and
n is 1 or 2, or a pharmaceutically acceptable salt thereof.

The present invention further provides a pharmaceutical composition, which contains a compound of the general formula (I) or a pharmaceutically acceptable salt thereof, and a pharmaceutically acceptable carrier, vehicle or diluent.

The present invention further provides the use of a compound of the general formula (I) or a pharmaceutically acceptable salt thereof in the manufacture of a medicament for inhibiting the activity of the sodium-dependent glucose cotransporter 2 (SGLT-2) relevant to the intestinal or renal glucose reabsorption.

The present invention further provides the use of a compound of the general formula (I) or a pharmaceutically acceptable salt thereof in the manufacture of a medicament for treating diabetes mellitus.

The present invention further provides a method of treating diabetes mellitus in a mammal, which comprises administrating to a subject in need thereof a compound of the general formula (I) or a pharmaceutically acceptable salt thereof according to the present invention.

According to the present invention, by the term "aryl" is meant an aromatic cyclic hydrocarbon group, preferably an aryl having 6-14 carbon atoms, such as phenyl and naphthyl, more preferably phenyl.

According to the present invention, by the term "heteroaryl" is meant a 5-6 membered monocyclic heterocycle group containing 1-4 heteroatoms selected from the group consisting of N, S and O, or a bicyclic heterocycle group formed by fusing said 5-6 membered monocyclic heterocycle with a benzene ring. It is unsaturated. Herein, it is preferable for the monocyclic heterocycle group to be a 5-6 membered monocyclic heteroaryl, in particular, furyl, thienyl, pyrrolyl, imidazolyl, pyrazolyl, thiazolyl, isothiazolyl, oxazolyl, isooxazolyl, triazolyl, tetrazolyl, thiadiazolyl, pyridyl, pyrimidinyl, pyridazinyl, and pyrazinyl, more preferably imidazolyl, thiazolyl, triazolyl, pyridyl and pyrazinyl; it is preferable for the bicyclic heterocycle group to be benzofuryl, benzothienyl, benzothiadiazolyl, benzothiazolyl, benzoimidazolyl, indolyl, isoindolyl, indazolyl, quinolinyl, isoquinolinyl, and quinazolinyl.

According to the present invention, by the term "nitrogen-containing saturated heterocyclic group" is meant a 5-6 membered saturated nitrogen-containing heterocycle group that contains 1-4 heteroatoms selected from the group consisting of N, O and S, preferably a 5-6 membered monocyclic nitrogen-containing saturated heterocyclic group, more preferably pyrrolidinyl, pyrazolidinyl, piperidinyl, piperazinyl, morpholinyl, and triazolidinyl, and further more preferably pyrrolidinyl, piperazinyl, piperidinyl or morpholinyl.

According to the present invention, by the term "nitrogen-containing partially unsaturated heterocyclic group" is meant a 5-6 membered nitrogen-containing heterocycle group that contains 1-4 heteroatoms selected from the group consisting of N, O and S and is partially unsaturated. Herein, it is preferable for the nitrogen-containing partially unsaturated heterocyclic group to be a 5-6 membered monocyclic nitrogen-containing partially unsaturated heterocyclic group, preferably pyrrolinyl and pyrazolinyl, and more preferably pyrrolinyl.

According to the present invention, by the term "halogen" is meant fluoro, chloro, bromo or iodo, preferably chloro or fluoro.

According to the present invention, by the term "$C_1$-$C_4$alkyl" is meant an alkyl that contains 1-4 carbon atoms, including but not limited to, for example, methyl, ethyl, propyl, isopropyl, butyl, isobutyl, sec-butyl or tert-butyl; preferably methyl, ethyl, propyl, isopropyl or butyl.

According to the present invention, by the term "$C_3$-$C_6$cycloalkyl" and "$C_3$-$C_8$cycloalkyl" are respectively meant a cycloalkyl that contains 3-6 carbon atoms and a cycloalkyl that contains 3-8 carbon atoms, including, for example, cyclopropyl, cyclobutyl, cyclopentyl, cyclohexyl, cycloheptyl or cyclooctyl; preferably cyclopropyl, cyclobutyl or cyclohexyl.

In a preferable embodiment of the present invention, in the compound of the general formula (I), X is S, and $R^4$ is —S—$C_1$-$C_4$alkyl, —SO—$C_1$-$C_4$alkyl or —$SO_2$—$C_1$-$C_4$alkyl, in particular —S—$CH_3$ or —$SO_2$—$CH_3$.

In another preferable embodiment of the present invention, in the compound of the general formula (I), each of $R^1$ and $R^2$ is independently hydrogen, —OH, —$NH_2$, —$NO_2$, —CN, —COOH, halogen, —$C_1$-$C_4$alkyl, —O—$C_1$-$C_4$alkyl or —$C_3$-$C_6$cycloalkyl, both of m and n are 1, and the substituent $R^1$ may be located at the ortho position, the meta position or the para position, preferably the para position of the glycoside.

In a more preferable embodiment of the present invention, in the compound of the general formula (I), $R^1$ is hydrogen, halogen or —$C_1$-$C_4$alkyl, preferably chloro or methyl, m is 1; $R^2$ is hydrogen, halogen or —$C_1$-$C_4$alkyl, preferably hydrogen, and n is 1.

In a preferable embodiment of the present invention, in the compound of the general formula (I), $R^3$ is halogen, an aryl having 1-3 substituents selected from the groups in Group A, a heteroaryl having 1-3 substituents selected from the groups in Group A, a nitrogen-containing saturated heterocyclic group having 1-3 substituents selected from the groups in Group A or a nitrogen-containing partially unsaturated heterocyclic group having 1-3 substituents selected from the groups in Group A, wherein, the group in Group A is selected from the group consisting of: hydrogen, halogen, —OH, —SH, —$NH_2$, —$NO_2$, —COH, —COOH, —$C_1$-$C_4$alkyl, —O—$C_1$-$C_4$alkyl, —S—$C_1$-$C_4$alkyl, —CONH—$C_3$-$C_6$cycloalkyl, —$C_1$-$C_4$alkyl—OH, —$C_1$-$C_4$alkyl-a nitrogen-containing saturated heterocyclic group.

In a preferable embodiment of the present invention, in the compound of the general formula (I), $R^3$ is halogen, preferably fluoro or chloro.

In another preferable embodiment of the present invention, in the compound of the general formula (I), $R^3$ is a phenyl having 1-3 substituents selected from the groups in Group A, wherein, the group in Group A is selected from the group consisting of: hydrogen, halogen, —OH, —$NH_2$, —$NO_2$, —COH, —COOH, —$C_1$-$C_4$alkyl, —O—$C_1$-$C_4$alkyl, —S—$C_1$-$C_4$alkyl, —CONH—$C_3$-$C_6$cycloalkyl, —$C_1$-$C_4$alkyl—OH, —$C_1$-$C_4$alkyl-a nitrogen-containing saturated heterocyclic group.

In another preferable embodiment of the present invention, in the compound of the general formula (I), $R^3$ is a pyridyl having 1-3 substituents selected from the groups in Group A, wherein, the group in Group A is selected from the group consisting of: hydrogen, halogen, —OH, —$NH_2$, —$NO_2$, —COH, —COOH, —$C_1$-$C_4$alkyl, —O—$C_1$-$C_4$alkyl, —S—$C_1$-$C_4$alkyl, —CONH—$C_3$-$C_6$cycloalkyl, —$C_1$-$C_4$alkyl—OH, —$C_1$-$C_4$alkyl-a nitrogen-containing saturated heterocyclic group.

In another preferable embodiment of the present invention, in the compound of the general formula (I), X is S;

each of $R^1$ and $R^2$ is independently hydrogen, —OH, —$NH_2$, —$NO_2$, —CN, —COOH, halogen, —$C_1$-$C_4$alkyl, —O—$C_1$-$C_4$alkyl or —$C_3$-$C_6$cycloalkyl, both of m and n are 1;

$R^3$ is halogen, a phenyl having 1-3 substituents selected from the groups in Group A or a pyridyl having 1-3 substituents selected from the groups in Group A, wherein, the group in Group A is selected from the group consisting of: hydrogen; halogen; —OH; —$NH_2$; —$NO_2$; —COH; —COOH; —$C_1$-$C_4$alkyl; —O—$C_1$-$C_4$alkyl such as —O—$CH_3$, —O—$CH_2$—$CH_3$, —O—$CH_2$—$CH_2$—$CH_3$; —S—$C_1$-$C_4$alkyl such as —S—$CH_3$, —S—$CH_2$—$CH_3$, —S—$CH_2$—$CH_2$—$CH_3$; —CONH—$C_3$-$C_6$cycloalkyl such as —CONH-cyclopropyl, —CONH-cyclopentyl, —CONH-cyclohexyl; —$C_1$-$C_4$alkyl—OH such as —$CH_2$—OH, —$CH_2$—$CH_2$—OH, —$CH_2$—$CH_2$—$CH_2$—OH; and —$C_1$-$C_4$alkyl-a nitrogen-containing saturated heterocyclic group such as —$CH_2$-piperazinyl, —$CH_2$-morpholinyl, —$CH_2$-piperidinyl, —$CH_2$-pyrrolidinyl, —$CH_2$—$CH_2$-piperazinyl, —$CH_2$—$CH_2$-morpholinyl, —$CH_2$—$CH_2$-piperidinyl, —$CH_2$—$CH_2$-pyrrolidinyl; and $R^4$ is —S—$C_1$-$C_4$alkyl, —SO—$C_1$-$C_4$alkyl or —$SO_2$—$C_1$-$C_4$alkyl, in particular —S—$CH_3$ or —$SO_2$—$CH_3$.

According to the present invention, the preferable specific compounds of the general formula (I) are the following compounds and pharmaceutically acceptable salts thereof:

(2S,3R,4R,5S,6R)-2-[3-((5-(4-fluorophenyl)thienyl)-2-methylene)-4-chloro-phenyl)-6-methylthio-tetrahydropyran-3,4,5-triol;

(2S,3R,4R,5S,6R)-2-[3-((5-(4-fluorophenyl)thienyl)-2-methylene)-4-methylphenyl)-6-methylthio-tetrahydropyran-3,4,5-triol;

(2S,3R,4R,5S,6R)-2-[3-((5-(4-fluoropyridyl)thienyl)-2-methylene)-4-chloro-phenyl)-6-methylthio-tetrahydropyran-3,4,5-triol;

(2S,3R,4R,5S,6R)-2-[3-((5-(4-chloro)thienyl)-2-methylene)-4-chloro-phenyl)-6-methylthio-tetrahydropyran-3,4,5-triol;

(2S,3R,4R,5S,6R)-2-[3-((5-(4-bromo)thienyl)-2-methylene)-4-methyl-phenyl)-6-methylthio-tetrahydropyran-3,4,5-triol;

(2S,3R,4R,5S,6R)-2-[3-((5-(3,4,5-trifluorophenyl)thienyl)-2-methylene)-4-methylphenyl)-6-methylthio-tetrahydropyran-3,4,5-triol;

(2S,3R,4R,5S,6R)-2-[3-((5-(3,4-difluorophenyl)thienyl)-2-methylene)-4-methylphenyl)-6-methylthio-tetrahydropyran-3,4,5-triol;

(2S,3R,4R,5S,6R)-2-[3-((5-(4-methoxyphenyl)thienyl)-2-methylene)-4-methylphenyl)-6-methylthio-tetrahydropyran-3,4,5-triol;

(2S,3R,4R,5S,6R)-2-[3-((5-(3-cynaophenyl)thienyl)-2-methylene)-4-methylphenyl)-6-methylthio-tetrahydropyran-3,4,5-triol;

(2S,3R,4R,5S,6R)-2-[3-((5-(2-formylphenyl)thienyl)-2-methylene)-4-methylphenyl)-6-methylthio-tetrahydropyran-3,4,5-triol;

(2S,3R,4R,5S,6R)-2-[3-((5-(3-formylphenyl)thienyl)-2-methylene)-4-methylphenyl)-6-methylthio-tetrahydropyran-3,4,5-triol;

(2S,3R,4R,5S,6R)-2-[3-((5-((4-methylpiperazin-1-yl)methyl)phenyl)thienyl)-2-methylene)-4-methylphenyl)-6-methylthio-tetrahydropyran-3,4,5-triol;

(2S,3R,4R,5S,6R)-2-[3-((5-(3-(morpholinylmethyl)phenyl) thienyl)-2-methylene)-4-methylphenyl)-6-methylthio-tetrahydropyran-3,4,5-triol;

(2S,3R,4R,5S,6R)-2-[3-((5-(4-carboxylphenyl)thienyl)-2-methylene)-4-methylphenyl)-6-methylthio-tetrahydropyran-3,4,5-triol;

(2S,3R,4R,5S,6R)-2-[3-((5-(4-N-cyclopropylbenzamide) thienyl)-2-methylene)-4-methylphenyl)-6-methylthio-tetrahydropyran-3,4,5-triol;

(2S,3R,4R,5S,6R)-2-[3-((5-(4-methylthiophenyl)thienyl)-2-methylene)-4-methylphenyl)-6-methylthio-tetrahydropyran-3,4,5-triol;

(2S,3R,4R,5S,6R)-2-[3-((5-(2-furyl)thienyl)-2-methylene)-4-methylphenyl)-6-methylthio-tetrahydropyran-3,4,5-triol;

(2S,3R,4R,5S,6R)-2-[3-((5-(4-hydroxymethylphenyl)thienyl)-2-methylene)-4-methylphenyl)-6-methylthio-tetrahydropyran-3,4,5-triol;

(2S,3R,4R,5S,6R)-2-[3-((5-(3-aminophenyl)thienyl)-2-methylene)-4-methylphenyl)-6-methylthio-tetrahydropyran-3,4,5-triol;

(2S,3R,4R,5S,6R)-2-[3-((5-(4-fluorophenyl)thienyl)-2-methylene)-2-methoxy-4-methylphenyl)-6-methylthio-tetrahydropyran-3,4,5-triol; and (2S,3R,4R,5S,6R)-2-[3-((5-(4-fluorophenyl)thienyl)-2-methylene)-4-chloro-phenyl)-6-methylsulfonyl-tetrahydropyran-3,4,5-triol.

The present invention further provides a process for preparing a compound of the general formula (I), which comprises the steps of:

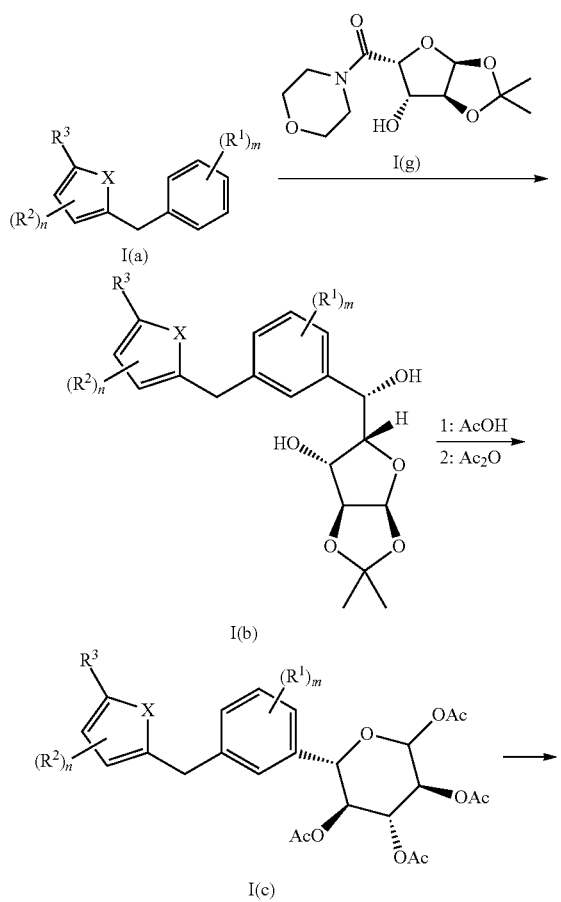

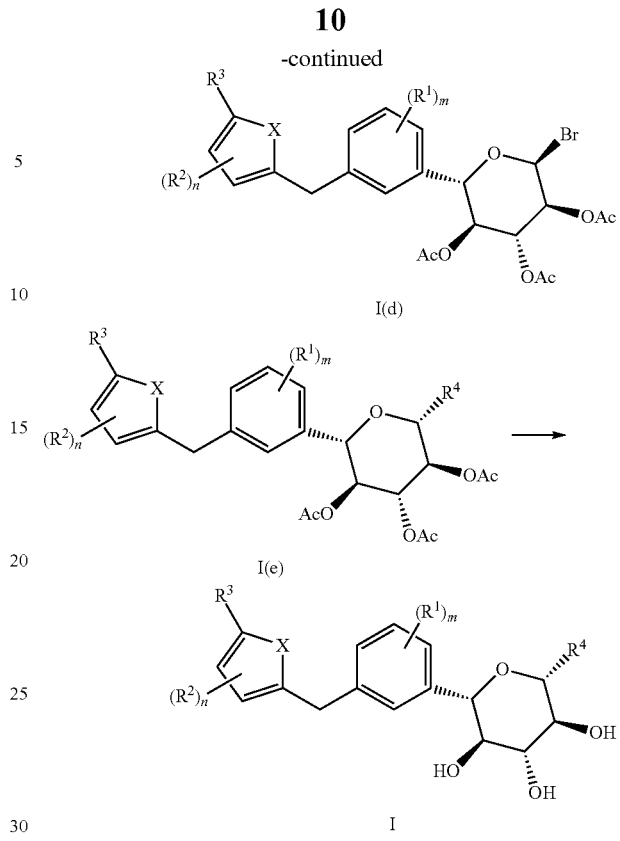

wherein, X, $R^1$, $R^2$, $R^3$, $R^4$, m and n are defined as above, (3aS,5R,6S,6aS)-[6-hydroxy-2,2-dimethyl-tetrahydrofuro [3,2-d][1,3]-dioxol-5-yl]-(morpholino)methan one I(g) (which is synthesized according to WO 2010/009197, starting from L-xylose, through bis-acetonide protection, selective acetonide deprotection, oxidation, amidation, and the like) is used as starting material, to which a halide e.g. iodide or bromide of formula I(a) is added, and then an alcohol I(b) is obtained; I(b) is treated with an alcohol and water in the presence of an acid such as acetic acid or sulfuric acid, and acetylizad with acetic anhydride in the presence of an organic base such as pyridine to obtain a compound I(c); I(c) is added to an acetic acid solution containing bromide hydrogen to conduct the reaction to obtain a compound I(d), which is reacted with a nucleophilic reagent such as alkoxide, mercaptide such as sodium alkoxide, sodium mercaptide or mercaptan without separation and purification to obtain a compound I(e) directly (if $R^4$=—O—$R^5$, —S—$R^5$) or after the oxidation (if $R^4$=—SO—$R^5$ or —$SO_2$—$R^5$); and the acetyl of the saccharide moiety in the compound I(e) is hydrolyzed according to any conventional method well known in the prior art to obtain the target compound I.

The compound of the present invention further comprises a pharmaceutically acceptable salt of the compound of the general formula (I). By the term "pharmaceutically acceptable salt" is meant a comparatively innoxious acid or base addition salt of the compound of the general formula (I) according to the present invention. The acid addition salt is a salt formed from the compound of formula (I) and a suitable inorganic or organic acid. The salt can be prepared during the final separation and purification of the compound, or prepared by the reaction of the purified compound in form of its free base and a suitable organic or inorganic acid, and the separation of the resulting salt. The representative acid addition salt includes but is not limited to hydrobromide, hydrochloride, sulfate, sulfite, acetate, oxalate, pentanoate, oleate, palmitate, stearate, laurate, borate, benzoate, lactate, phosphate, toluate, citrate, maleate, fumarate, succinate, tartrate, benzoate, mesylate, p-toluene sulfonate, gluconate, lactobionate, laurylsulfonate, and the like.

The base addition salt is a salt formed from the compound of formula (I) and a suitable inorganic or organic base, including, for example, a salt formed from an alkali metal, an alkaline earth metal or a quaternary ammonium cation, such as a sodium salt, a lithium salt, a potassium salt, a calcium salt, a magnesium salt, a tetramethyl quaternary ammonium salt, a tetraethyl quaternary ammonium salt and the like; an amine salt, including a salt formed from ammonia ($NH_3$), a primary amine, a secondary amine, or a tertiary amine, such as a methylamine salt, a dimethylamine salt, a trimethylamine salt, a triethylamine salt, an ethylamine salt, and the like.

The compound of the general formula (I) according to the present invention and a pharmaceutically acceptable salt thereof can administrated to a mammal, e.g. human orally, rectally, parenterally (intravenously, intramuscularly, subcutaneously), topically (e.g. in a dosage form such as pulvis, ointment and drop), and the like.

The compound of the general formula (I) according to the present invention and a pharmaceutically acceptable salt thereof can be formulated to a solid dosage form for the oral administration, including but not limited to, e.g. capsules, tablets, pills, powders and granules. In such solid dosage forms, the present compound or a pharmaceutically acceptable salt thereof can be mixed with at least one conventional inert vehicle (or carrier), such as sodium citrate or dicalcium phosphate and/or the following substances: (a) filler or bulking agent, such as starch, lactose, sucrose, glucose, mannitol and silicic acid; (b) binding agent, such as carboxymethyl cellulose, alginate, gelatin, polyvinyl pyrrolidone, sucrose, and arabic gum; (c) humectant, such as glycerol; (d) disintegrating agent, such as agar, calcium carbonate, potato or cassava starch, alginic acid, some complex silicates and sodium carbonate; (e) solution-blocking agent, such as paraffin wax; (f) absorption accelerator, such as quaternary ammonium compounds; (g) wetting agent, such as cetanol and glycerol monostearate; (h) adsorbent, such as kaolin; and (i) lubricant, such as talc, calcium stearate, magnesium stearate, solid polyethylene glycol, sodium dodecylsulfate and their mixtures. In the cases of capsules, tablets and pills, these dosage forms may also comprise a buffering agent.

The solid dosage forms such as tablets, dragees, capsules, pills and granules can be prepared with coating agents and shell materials such as enteric coating materials and other coating materials well-known in the field of medical preparations. These solid dosage forms can optionally comprise sun-screening agent, and their composition can allow they merely or preferentially release active ingredient at some sites of intestinal tract optionally in a delayed manner. Examples of embedding composition comprise high molecular materials and waxes. If appropriate, the present compound or a pharmaceutically acceptable salt thereof can be formulated to form of microcapsules with one or more aforementioned vehicles.

The compound of the general formula (I) according to the present invention and a pharmaceutically acceptable salt thereof can also be formulated to a liquid dosage form for oral administration, including pharmaceutically acceptable emulsion, solution, suspension, syrup and elixir. In addition to the compound of the general formula (I) according to the present invention or a pharmaceutically acceptable salt thereof as the active compound, the liquid formulation may comprise an inert diluent commonly used in the art such as, for example, water or other solvent, solubilizing agent and emulsifier (e.g., ethyl alcohol, isopropyl alcohol, ethyl carbonate, ethyl acetate, propylene glycol, 1,3-butylene glycol, dimethylformamide, oil (in particular, cottonseed, groundnut, corn germ, olive, castor or sesame oil), and mixtures thereof.)

Besides the inert diluent, these dosage forms may also comprise an adjuvant such as a wetting agent, an emulsifier, a suspending agent, a sweetener, a flavor and a perfume.

A suspension, in addition to the compound of the general formula (I) according to the present invention or a pharmaceutically acceptable salt thereof, may comprise a suspending agent (e.g., ethoxylated isostearyl alcohol, polyoxyethylene sorbitol and sorbitan ester, microcrystalline cellulose, aluminum metahydroxide, agar-agar, or mixtures thereof).

The compound of the general formula (I) according to the present invention and a pharmaceutically acceptable salt thereof can be formulated to a formulation suitable for parenteral injection, including but not limited to a physiologically acceptable sterile aqueous or oleaginous solution, dispersion, suspension or emulsion, and sterile powder which can be dissolved or dispersed in to prepare sterile injectable solution or dispersion. Examples of suitable aqueous or oleaginous carrier, diluent, solvent or vehicle include water, ethanol, polyol, and adequate mixtures thereof.

The compound of the general formula (I) according to the present invention and a pharmaceutically acceptable salt thereof can be formulated to a dosage form for topical administration, including ointment, powder, spray and inhalant. The compound of the general formula (I) according to the present invention or a pharmaceutically acceptable salt thereof can be mixed under sterile condition with physiologically acceptable carriers and any antiseptics, buffers, or required propellants, if necessary.

The present invention further provides a pharmaceutical composition, which comprises 0.01-50 mg of the compound of the general formula (I) according to the present invention or a pharmaceutically acceptable salt thereof as mentioned above, and a pharmaceutically acceptable carrier, vehicle or diluent.

The pharmaceutical composition of the present invention can be prepared by any conventional method, for example, by mixing the compound of the general formula (I) according to the present invention or a pharmaceutically acceptable salt thereof and a pharmaceutically acceptable carrier, vehicle or diluents.

The present invention further provides a method for treating a disease, which disease can be alleviated or treated by promoting the urine glucose excretion, such as type II diabetes mellitus, comprising the step of administering to a patient in need thereof the compound of formula (I) or a pharmaceutically acceptable salt thereof in a dose of 0.1-50 mg/kg body weight/day.

The present compound or a pharmaceutically acceptable salt thereof can be administered alone or in combination with other pharmaceutically acceptable therapeutic agents, in particular other anti-diabetic drugs. The therapeutic agent includes but is not limited to: biguanides, such as dimethyl biguanide; thiazolidinediones, such as troglitazone, rosiglitazone, pioglitazone; α-glucosidase inhibitors, such as acarbose, voglibose, migltol; sulfonylurea insulin secretagogues, such as glibenclamide, glipizide, glibornuride, gliclazide, glimepiride; postprandial glucose regulators such as repaglinide; PPARα/γ dual-agonists; DPP-IV inhibitors; PTP1B inhibitors and the like. The ingredients to be combined can be administered simultaneously or sequentially, and can be administered either in a unitary formulation or in separate formulations. Such combination includes not only the combination of the present compound with one other active agent but also the combination of the present compound with two or more other active agents.

It is proved by the assays that the present compounds can promote the urine glucose excretion and therefore can be useful for preparing the medicament for treating diabetes mellitus.

The drug effect of promoting the urine glucose excretion can be determined according to the conventional assay. One preferable evaluation assay is to detect the effect of the present compound on the urine glucose excretion of the normal rat. The assay can be conducted as follows. Thirty 7-week-old male SD rats (about 200 g) are used in the assay. The tested compound having a purity of 97.8% is formulated with 0.75% CMC-Na. The positive control drug (Dapagliflozin) having a purity of 98% is formulated with 0.75% CMC-Na. The SD rats are acclimatized for 7 days, and then placed in the metabolic cages. The rats are fasted overnight (18 hr) under the free access to water. The basic urine samples are collected, and then thirty rats are weighed and grouped randomly into five groups, six rats per group. The rats are administered with the tested compounds or the positive control drug at low dosage, medium dosage, or high dosage. Fifteen minutes after the administration, the rats are intragastrically administrated with 50% glucose solution (2 g/kg). For ensuring a complete collection of the 24-hour urine, the rats are immediately placed in the metabolic cage after the administration of the tested compounds or the positive control drug. One hour after the administration of the glucose solution, the feeds are supplied to the rats. The urines after the administration of the tested compounds or the positive control drug are collected for 24 hours, and then the urine volumes are calculated and the urine glucose concentrations are detected.

The data are analyzed with the software SPSS 12.0, and the quantized data are expressed in "average±standard deviation". Multiple sets of data are compared according to the analysis of variance (One-way ANOVA). P<0.05 represents statistical difference.

Figure 1:
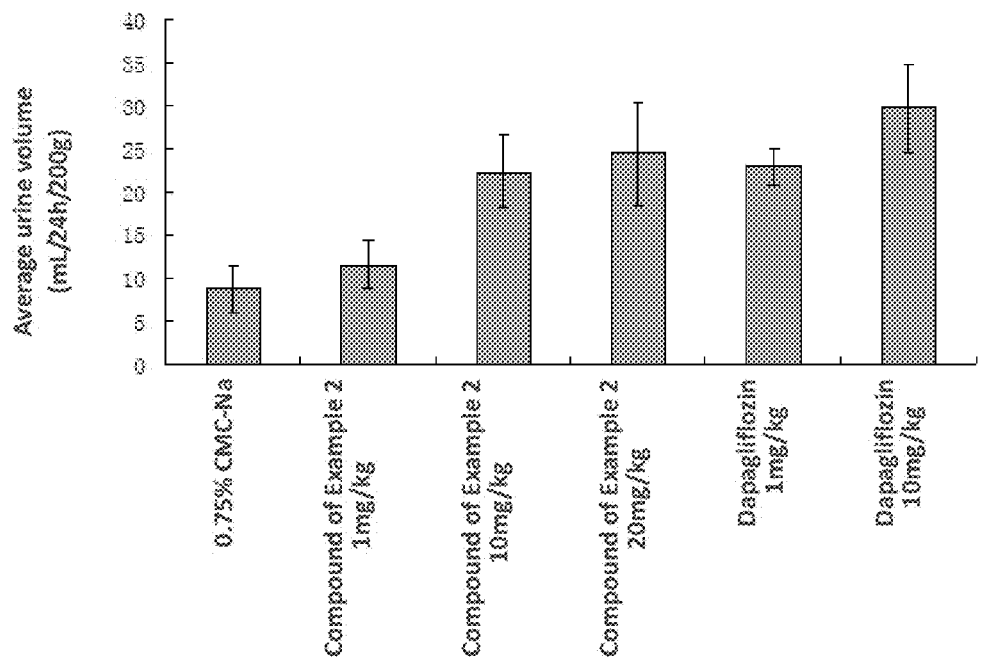
FIG. 1 shows the volumes of the urine excreted in 24 hours after the single intragastric oral administrations of the compound of Example 2 and the positive control drug (dapagliflozin) to normal rats.
Figure 2:
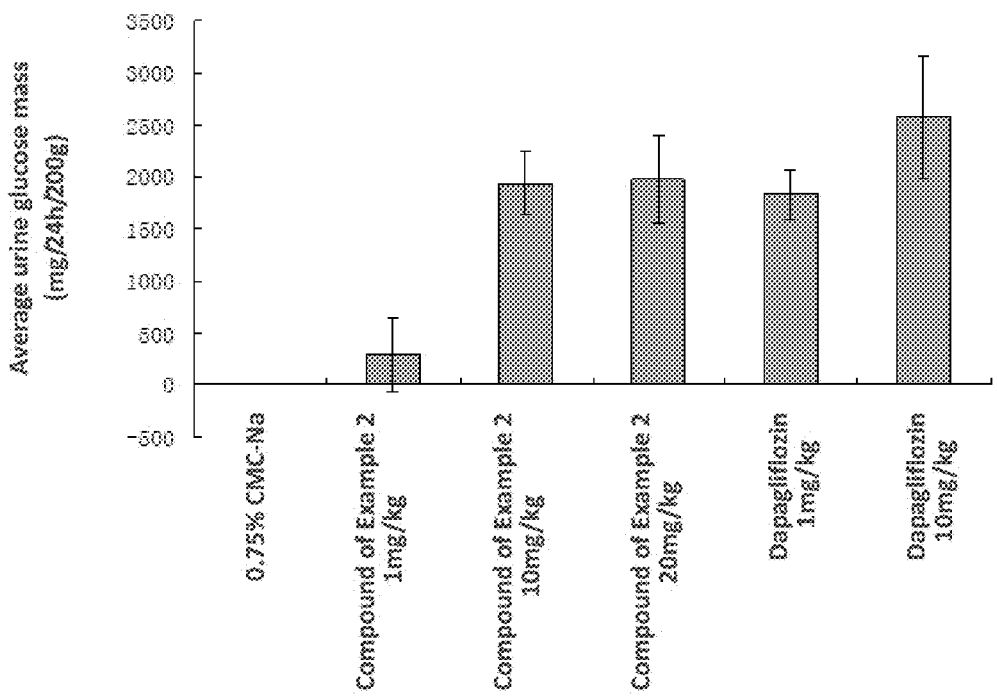
FIG. 2 shows the masses of the urine glucose excreted in 24 hours after the single intragastric oral administrations of the compound of Example 2 and the positive control drug (dapagliflozin) to normal rats.

The present invention will now be described in connection with certain embodiments which are not intended to limit its scope. It should be recognized thus that the following examples are for the purposes of illustration of the practice of the present invention only. The specific condition of the experimental methods used in the following examples, which was not set forth, is generally according to the conventional condition, or according to the condition suggested by the manufacturers. Unless otherwise indicated, the parts and percents are by weight.

The abbreviations used in Examples have the meanings well known in the field to which the present invention belongs. For example, i-PrMgCl represents isopropyl magnesium chloride; THF represents tetrahydrofuran; HOAc represents acetic acid; $Ac_2O$ represents acetic anhydride; Py represents pyridine; TEA represents triethylamine; $Et_3N$ represents triethylamine; and MeCN represents acetonitrile.

BEST MODES OF CARRYING OUT THE INVENTION

I. Preparation Examples of the Present Compounds

Example 1

Synthesis of (2S,3R,4R,5S,6R)-2-[3-((5-(4-fluorophenyl)thienyl)-2-methylene)-4-chloro-phenyl)-6-methylthio-tetrahydropyran-3,4,5-triol

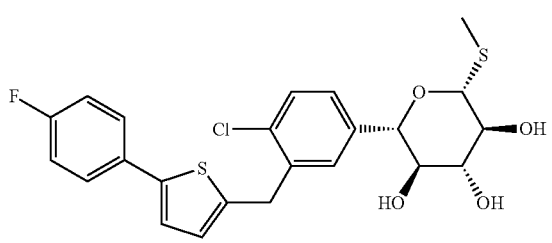

The title compound was prepared by the following steps:

1) Synthesis of Compound 1(b)

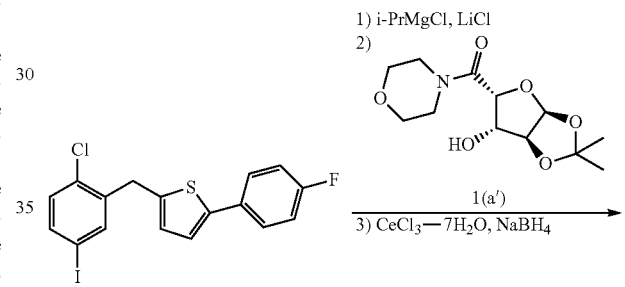

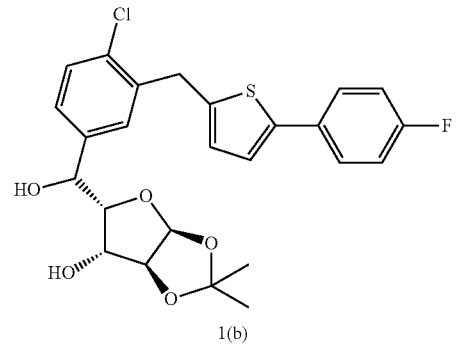

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system 1(a) (4.04 g, 9.46 mmol) was added in batch. Then the reaction system was kept at this temperature and stirred for 1 hr. Then to the reaction system, the solid 1(a') (2.3 g, 8.5 mmol) (which was synthesized according to WO 2010/009197, starting from L-xylose, through bis-acetonide protection, selective acetonide deprotection, oxidation, amidation, and the like) was added. The stirring was continued for 1 hr. Then the reaction was quenched with a saturated $NH_4Cl$ solution. The aqueous phase was removed and extracted with ethyl acetate. The organic phases were combined, washed with water and a saturated aqueous NaCl solution successively, dried with anhydrous Na$_2$SO$_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$ and concentrated to produce a crude pale yellow oily product 1(b).

$^1$H NMR (400 Hz, CDCl$_3$) δ1.24 (s, 6H), 4.33 (s, 2H), 4.59-4.61 (m, 2H), 5.27 (d, J=2 Hz, 1H), 6.08 (d, J=3.2 Hz, 1H), 6.82 (d, J=3.6 Hz, 1H), 7.03-7.09 (m, 3H), 7.50-7.54 (m, 3H), 7.91-8.00 (m, 2H).

2) Synthesis of Compound 1(c)

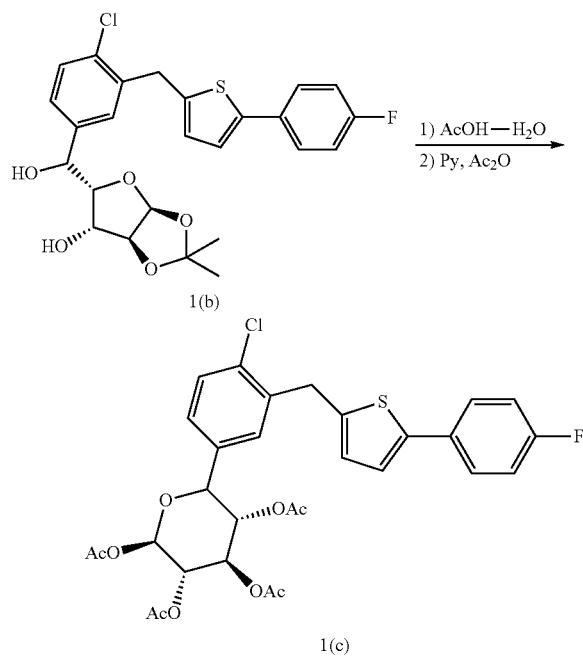

The crude Compound 1(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL). The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 1(c) (518 mg, 76%).

3) Synthesis of Compound 1(e)

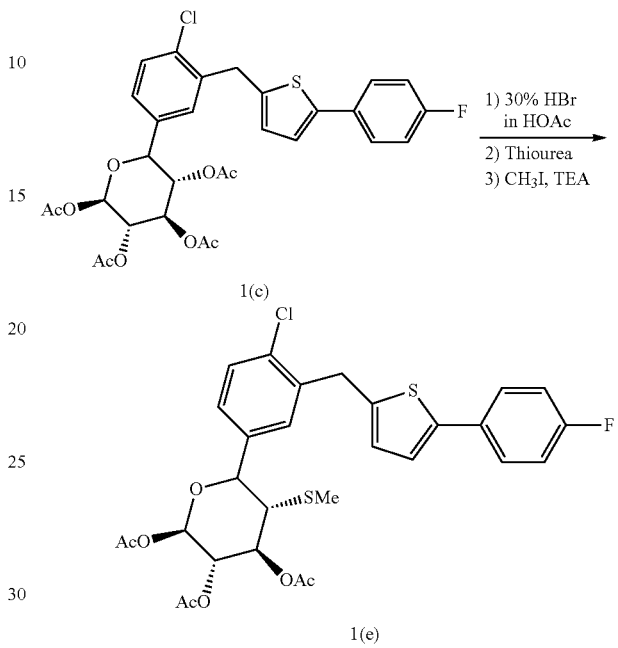

Under an ice-water bath, to a single-neck bottle containing Compound 1(c) (418 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, 8 mL MeCN and 154 mg S(NH$_2$)$_2$ were added to the above resulting pale yellow liquid. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 1(e) (251 mg, 60% (three steps)).

$^1$H NMR (400 Hz, CDCl$_3$) δ1.77 (s, 3H), 2.02 (s, 3H), 2.11 (s, 3H), 2.17 (s, 3H), 4.28 (2H), 4.43 (d, J=10 Hz, 1H), 4.53 (d, J=10 Hz, 1H), 5.08 (t, J=9.6 Hz, 1H), 5.22 (t, J=9.6 Hz, 1H), 5.32 (t, J=9.2 Hz, 1H), 6.76 (d, J=3.6 Hz, 1H), 7.03-7.08 (m, 3H), 7.23-7.25 (m, 2H), 7.39-7.41 (m, 2H), 7.49-7.53 (m, 3H).

4) Synthesis of Compound 1

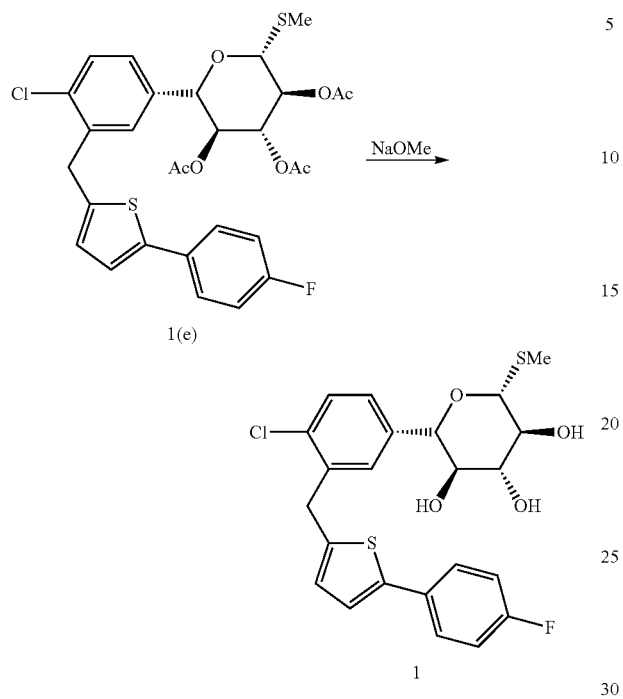

Compound 1(e) (251 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 1 (172 mg, 86%).

$^1$H NMR (400 Hz, CDCl$_3$) δ2.17 (d, J=2.8 Hz, 1H), 2.21 (s, 3H), 2.58 (d, J=2.0 Hz, 1H), 2.89 (d, J=2.0 Hz, 1H), 3.53-3.59 (m, 2H), 3.73 (t, J=4.6 Hz, 1H), 4.24-4.30 (m, 3H), 4.42 (d, J=9.6 Hz, 1H), 6.81 (d, J=3.2 Hz, 1H), 7.04-7.08 (m, 3H), 7.27-7.30 (m, 1H), 7.35-7.53 (m, 4H).

ESI(+)m/z: 480

Example 2

Synthesis of (2S,3R,4R,5S,6R)-2-[3-((5-(4-fluorophenyl)thienyl)-2-methylene)-4-methylphenyl)-6-methylthio-tetrahydropyran-3,4,5-triol

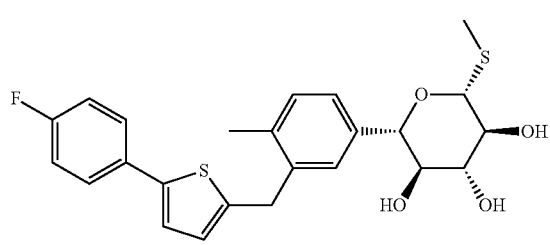

1) Synthesis of Compound 2(b)

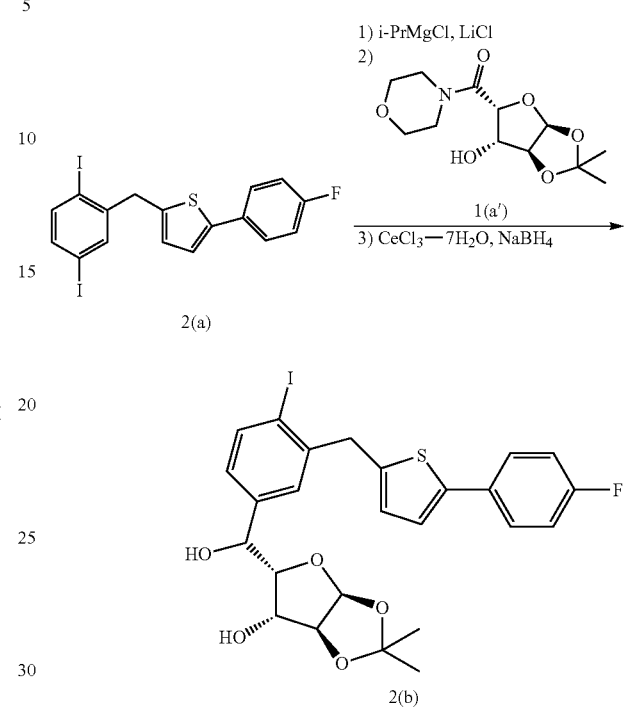

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 2(a) (3.9 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$ and concentrated to produce a crude pale yellow oily product 2(b).

2) Synthesis of Compound 2(c)

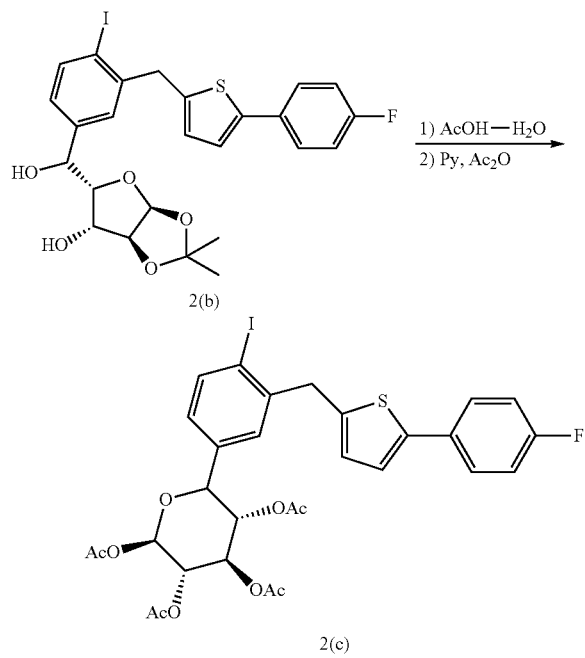

2(b)

2(c)

The crude Compound 2(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and $Ac_2O$ (0.5 mL) were added slowly under an ice-water bath cooling. After the completion of the addition, the mixture was stirred at room temperature for 2 hrs. A saturated aqueous $NaHCO_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous $Na_2SO_4$, and concentrated. The resulting residue was separated by a silica gel column chromatography (petroleum ether/ethyl acetate=2:1) to produce a pale yellow solid 2(c) (404 mg, 61%).

3) Synthesis of Compound 2(e)

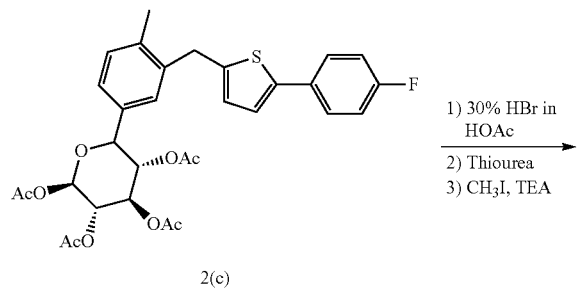

2(c)

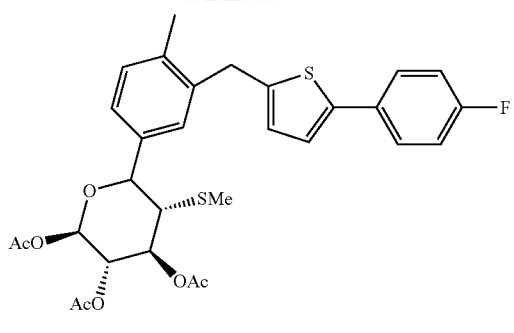

2(e)

Under an ice-water bath, to a single-neck bottle containing Compound 2(c) (404 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous $NaHCO_3$ solution. The organic phase was separated. The aqueous phase was extracted with dichloromethane (3×10 mL). The organic phases were combined, washed with water and a saturated aqueous NaCl solution successively, dried with anhydrous $Na_2SO_4$, and concentrated to produce a pale yellow liquid.

At room temperature, to the above resulting pale yellow liquid, 8 mL MeCN and 154 mg $S(NH_2)_2$ were added. The mixture was heated under reflux for 1 hr, and then cooled to room temperature. $Et_3N$ (4 eq) and $CH_3I$ (3 eq) were added. The mixture was stirred for 1 hr. The reaction was quenched with a saturated aqueous $NaHCO_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous $Na_2SO_4$, and concentrated. The resulting residue was purified by a silica gel column chromatography (petroleum ether/ethyl acetate=5:1) to produce a pale yellow solid 2(e) (242 mg, 61% (three steps)).

4) Synthesis of Compound 2

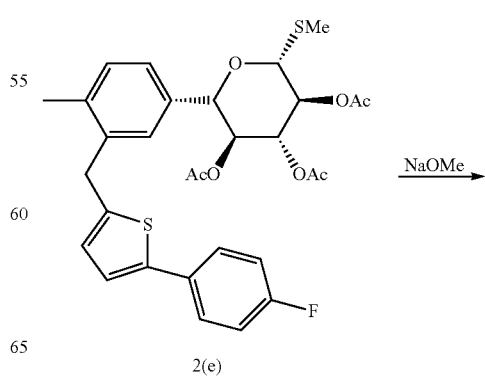

2(e)

21

-continued

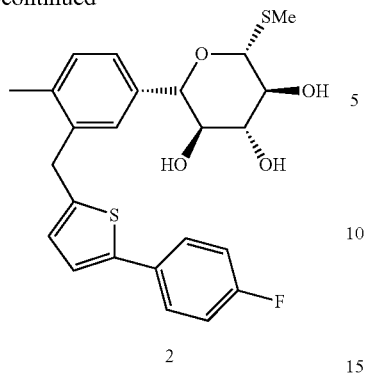

2

Compound 2(e) (242 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 2(92 mg, 48%).

1H NMR (400 MHz, CDCl$_3$) δ7.63 7.42 (m, 2H), 7.28 7.18 (m, 3H), 7.10 6.99 (m, 3H), 6.70 (d, J=3.6 Hz, 1H), 4.43 (d, J=9.6 Hz, 1H), 4.24 (d, J=9.4 Hz, 1H), 4.17 (s, 2H), 3.75 (t, J=8.8 Hz, 1H), 3.61 (t, J=9.1 Hz, 2H), 2.91 (s, 1H), 2.60 (s, 1H), 2.35 (s, 3H), 2.22 (s, 3H), 2.07 (s, 1H).

ESI(+)m/z: 460

Example 3

Synthesis of (2S,3R,4R,5S,6R)-2-[3-((5-(4-fluoropyridyl)thienyl)-2-methylene)-4-chloro-phenyl)-6-methylthio-tetrahydropyran-3,4,5-triol

3

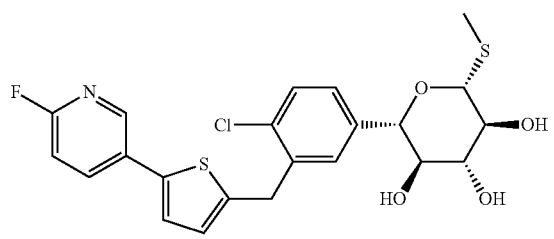

1) Synthesis of Compound 3(b)

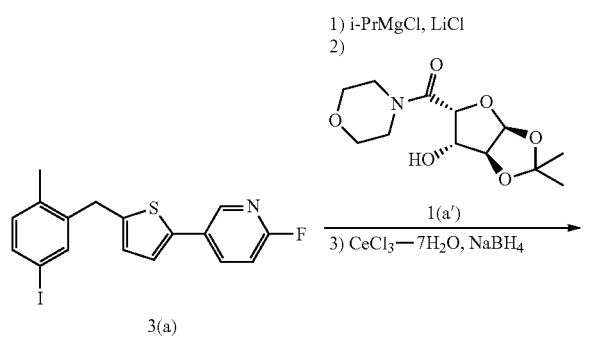

3(a)

22

-continued

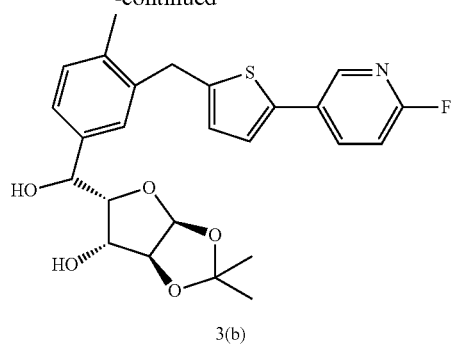

3(b)

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 3(a) (3.87 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$ and concentrated to produce a crude pale yellow oily product 3(b).

2) Synthesis of Compound 3(c)

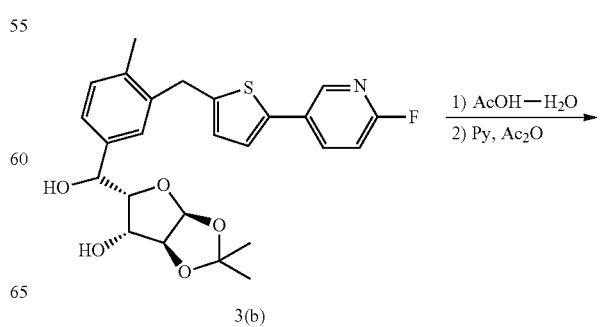

3(b)

23

-continued

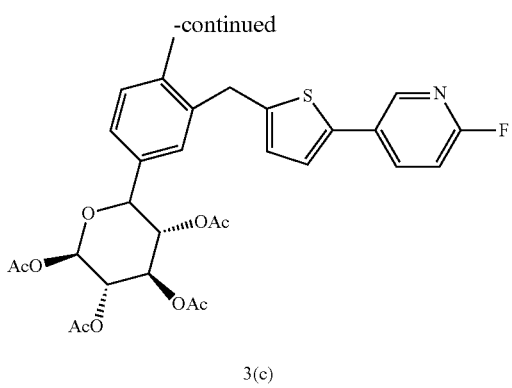

3(c)

The crude Compound 3(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 3(c) (522 mg, 79%).

3) Synthesis of Compound 3(e)

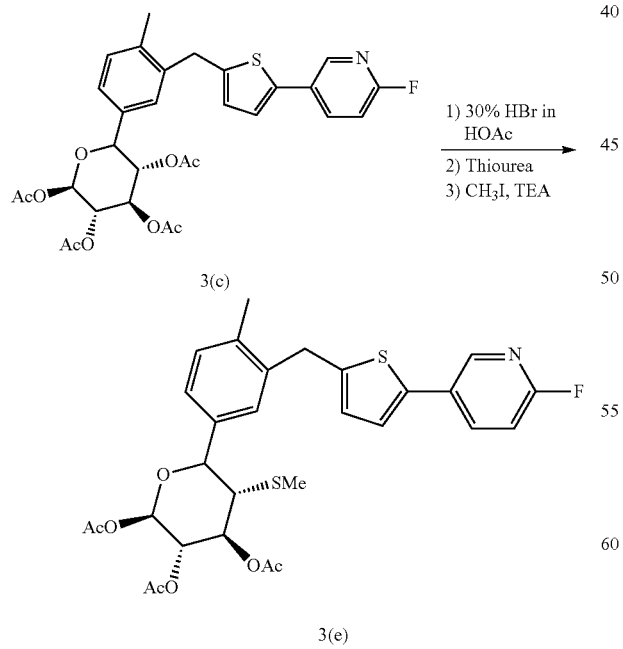

Under an ice-water bath, to a single-neck bottle containing Compound 3(c) (406 mg, 0.676 mmol), 30% HBr/HOAc

24 solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 3(e) (243 mg, 61% (three steps)).

4) Synthesis of Compound 3

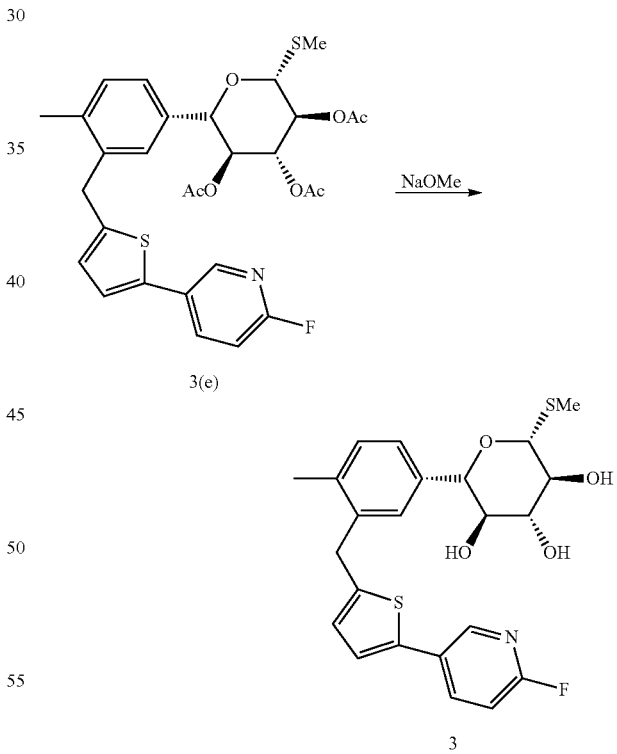

Compound 3(e) (243 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 3 (172 mg, 86%).

¹H NMR (400 Hz, CDCl₃) δ2.19 (d, J=2.8 Hz, 1H), 2.23 (s, 3H), 2.60 (d, J=2.0 Hz, 1H), 2.87 (d, J=2.0 Hz, 1H), 3.55-3.59 (m, 2H), 3.72 (t, J=4.6 Hz, 1H), 4.26-4.30 (m, 3H), 4.44 (d, J=9.6 Hz, 1H), 6.84 (d, J=3.2 Hz, 1H), 7.06-7.12 (m, 2H), 7.31-7.34 (m, 3H), 8.31-8.34 (m, 1H), 8.61 (d, J=1.8 Hz, 1H). ESI(+)m/z: 481

Example 4

Synthesis of (2S,3R,4R,5S,6R)-2-[3-((5-(4-chloro)thienyl)-2-methylene)-4-chloro-phenyl)-6-methylthio-tetrahydropyran-3,4,5-triol

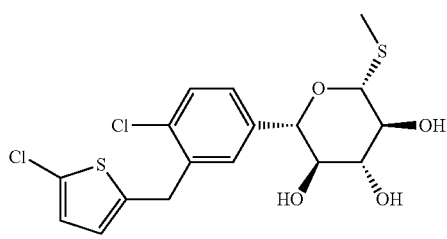

4

1) Synthesis of Compound 4(b)

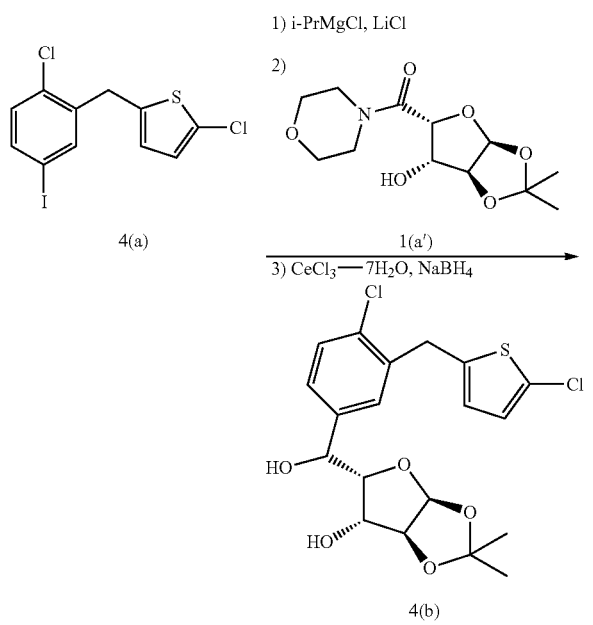

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 4(a) (3.5 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH₄Cl solution. The aqueous phase was removed and extracted with ethyl acetate. The organic phases were combined, washed with water and a saturated aqueous NaCl solution successively, dried with anhydrous Na₂SO₄ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl₃.7H₂O (490 mg, 1.32 mmol) was added at room temperature. The mixture was stirred for 20 mins until it completely dissolved, and cooled to -78° C. NaBH₄ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na₂SO₄ and concentrated to produce a crude pale yellow oily product 4(b).

2) Synthesis of Compound 4(c)

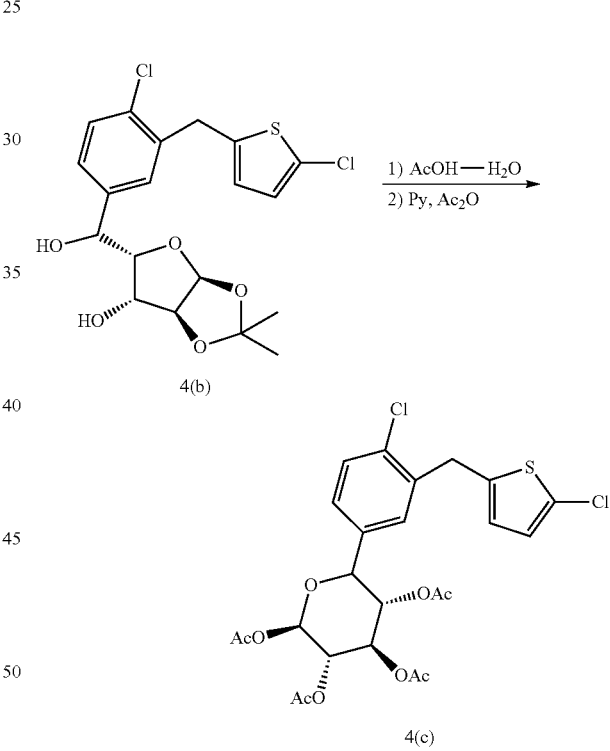

The crude Compound 4(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac₂O (0.5 mL) were added slowly under an ice-water bath cooling. After the completion of the addition, the mixture was stirred at room temperature for 2 hrs. A saturated aqueous NaHCO₃ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 4(c) (528 mg, 86%).

3) Synthesis of Compound 4(e)

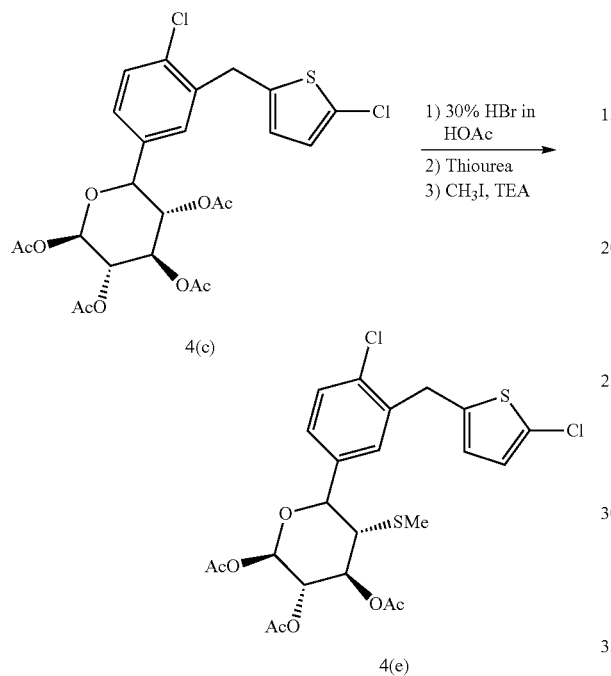

Under an ice-water bath, to a single-neck bottle containing Compound 4(c) (378 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 4(e) (278 mg, 75% (three steps)).

4) Synthesis of Compound 4

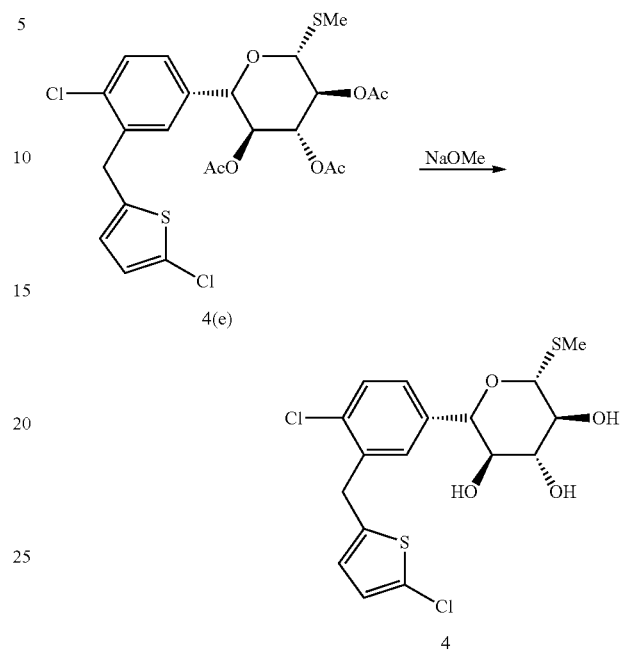

Compound 4(e) (226 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 4 (143 mg, 82%).

$^1$H NMR (400 Hz, CDCl$_3$) δ2.17 (d, J=2.8 Hz, 1H), 2.21 (s, 3H), 2.58 (d, J=2.0 Hz, 1H), 2.89 (d, J=2.0 Hz, 1H), 3.53-3.59 (m, 2H), 3.73 (t, J=4.6 Hz, 1H), 4.24-4.30 (m, 3H), 4.42 (d, J=9.6 Hz, 1H), 6.88 (d, J=3.2 Hz, 1H), 6.94 (d, J=3.2 Hz, 1H), 7.14-7.18 (m, 2H), 8.25-8.28 (m, 1H).

ESI(+)m/z: 420

Example 5

Synthesis of (2S,3R,4R,5S,6R)-2-[3-((5-(4-bromo)thienyl)-2-methylene)-4-methyl-phenyl)-6-methylthio-tetrahydropyran-3,4,5-triol

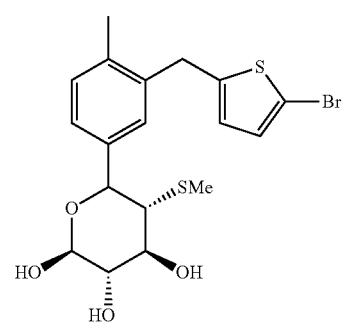 [SMILES: CS[C@H]1C(c2ccc(C)c(Cc3ccc(Br)s3)c2)O[C@H](O)[C@@H](O)[C@@H]1O]

1) Synthesis of Compound 5(b)

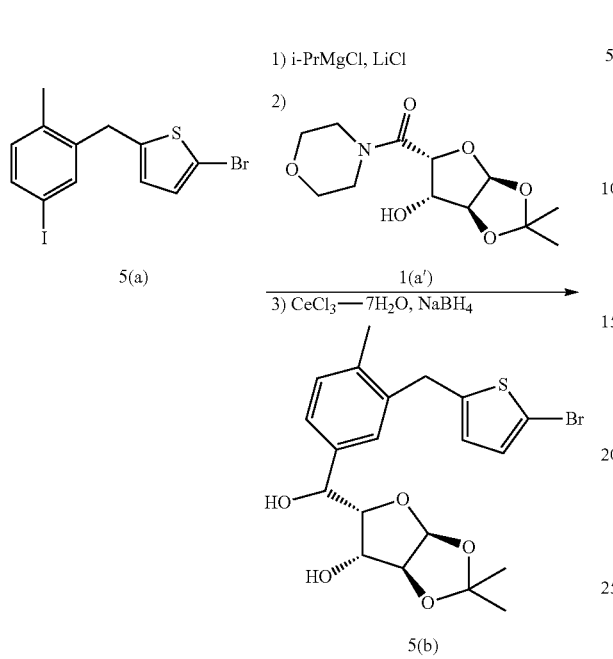

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 5(a) (3.7 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated $NH_4Cl$ solution. The aqueous phase was removed and extracted with ethyl acetate. The organic phases were combined, washed with water and a saturated aqueous NaCl solution successively, dried with anhydrous $Na_2SO_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). $CeCl_3 \cdot 7H_2O$ (490 mg, 1.32 mmol) was added at room temperature. The mixture was stirred for 20 mins until it completely dissolved, and cooled to −78° C. $NaBH_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous $Na_2SO_4$ and concentrated to produce a crude pale yellow oily product 5(b).

2) Synthesis of Compound 5(c)

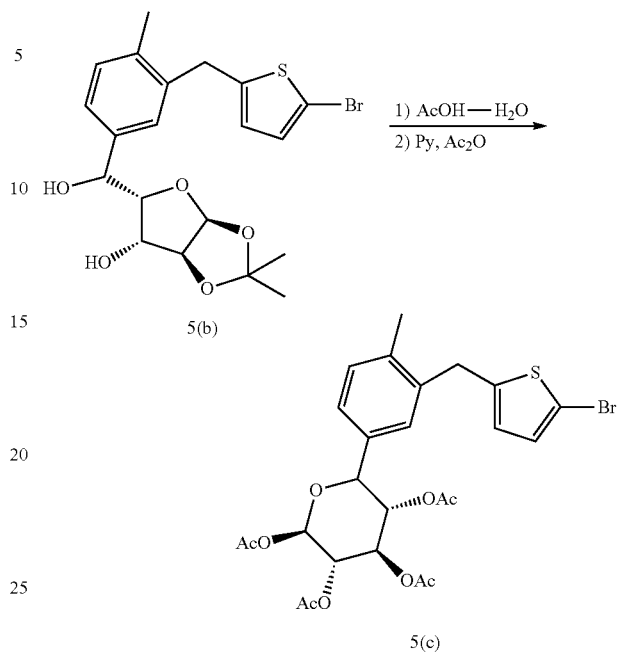

The crude Compound 5(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and $Ac_2O$ (0.5 mL) were added slowly under an ice-water bath cooling. After the completion of the addition, the mixture was stirred at room temperature for 2 hrs. A saturated aqueous $NaHCO_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous $Na_2SO_4$, and concentrated. The resulting residue was separated by a silica gel column chromatography (petroleum ether/ethyl acetate=2:1) to produce a pale yellow solid 5(c) (499 mg, 78%).

3) Synthesis of Compound 5(e)

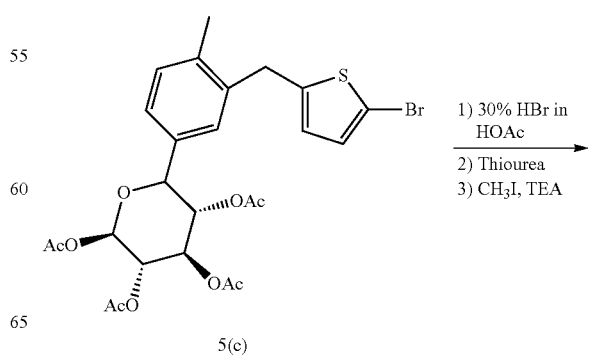

31

-continued

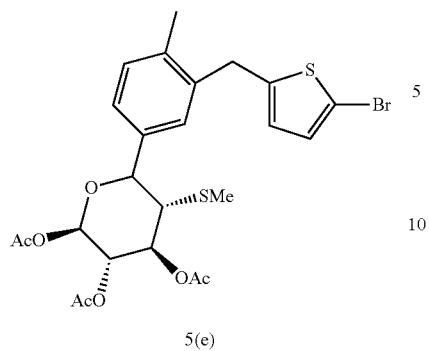

5(e)

Under an ice-water bath, to a single-neck bottle containing Compound 5(c) (394 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 5(e) (237 mg, 61% (three steps)).

$^1$H NMR (400 Hz, CDCl$_3$) δ1.80 (s, 3H), 2.03 (s, 3H), 2.12 (s, 3H), 2.20 (s, 3H), 2.28 (s, 3H), 4.04 (d, J=2 Hz, 2H), 4.42 (d, J=10 Hz, 1H), 4.54 (d, J=10 Hz, 1H), 5.13 (t, J=9.6 Hz, 1H), 5.23 (d, J=9.6 Hz, 1H), 5.36 (t, J=9.6 Hz, 1H), 6.44 (d, J=4 Hz, 1H), 6.86 (d, J=3.6 Hz, 1H), 7.12 (s, 1H), 7.16-7.20 (m, 2H).

4) Synthesis of Compound 5

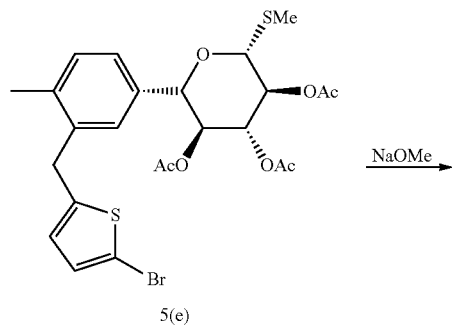

32

-continued

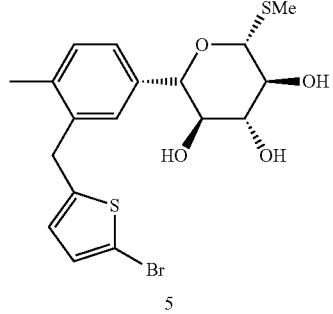

5

Compound 5(e) (237 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 5 (158 mg, 86%).

$^1$H NMR (400 Hz, CDCl$_3$) δ2.23 (s, 3H), 2.32 (s, 3H), 3.68-3.72 (m, 2H), 3.76-3.80 (m, 1H), 4.19 (s, 2H), 4.25 (d, J=8.4 Hz, 1H), 4.40 (d, J=9.2 Hz, 1H), 6.47 (d, J=4 Hz, 1H), 6.88 (d, J=3.6 Hz, 1H), 7.15 (s, 1H), 7.16-7.20 (m, 2H).

ESI(+)m/z: 446

Example 6

Synthesis of (2S,3R,4R,5S,6R)-2-[3-((5-(3,4,5-trifluorophenyl)thienyl)-2-methylene)-4-methylphenyl)-6-methylthio-tetrahydropyran-3,4,5-triol

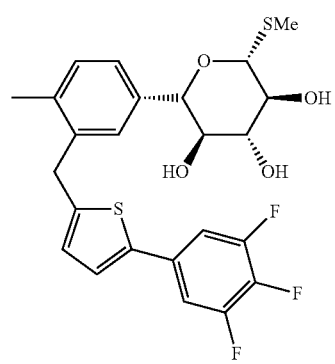

6

1) Synthesis of Compound 6(b)

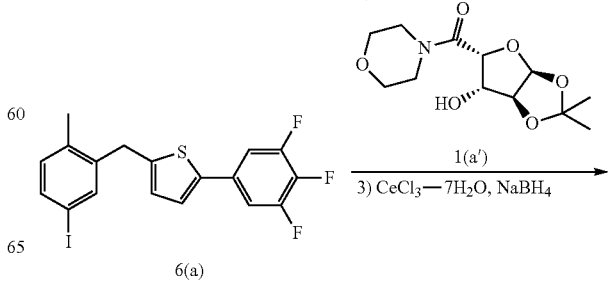

-continued

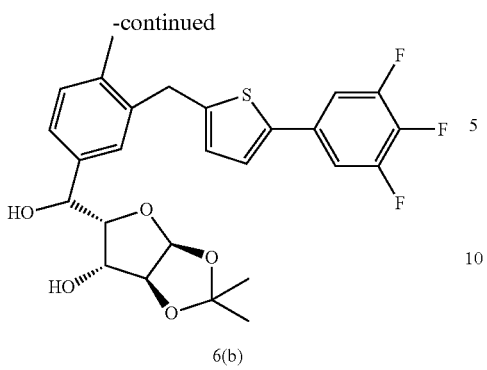

6(b)

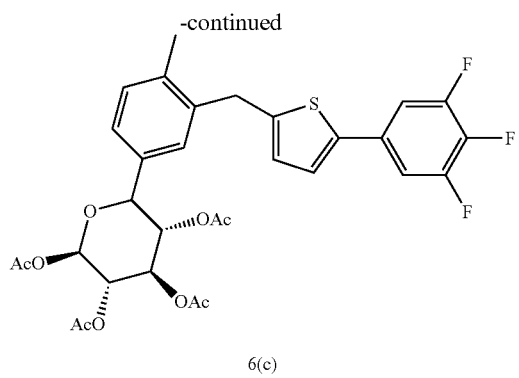

6(c)

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 6(a) (4.2 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated $NH_4Cl$ solution. The aqueous phase was removed and extracted with ethyl acetate. The organic phases were combined, washed with water and a saturated aqueous NaCl solution successively, dried with anhydrous $Na_2SO_4$, and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). $CeCl_3.7H_2O$ (490 mg, 1.32 mmol) was added at room temperature. The mixture was stirred for 20 mins until it completely dissolved, and cooled to −78° C. $NaBH_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous $Na_2SO_4$, and concentrated to produce a crude pale yellow oily product 6(b).

2) Synthesis of Compound 6(c)

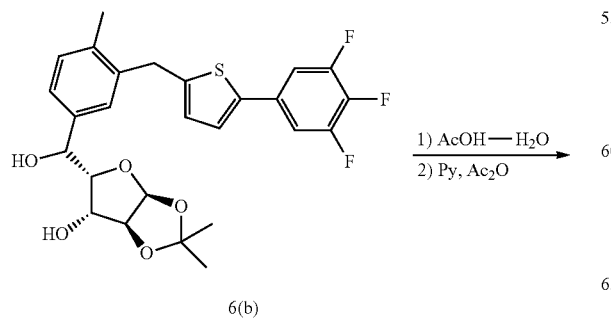

6(b)

1) AcOH—$H_2O$
2) Py, $Ac_2O$

The crude Compound 6(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and $Ac_2O$ (0.5 mL) were added slowly under an ice-water bath cooling. After the completion of the addition, the mixture was stirred at room temperature for 2 hrs. A saturated aqueous $NaHCO_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous $Na_2SO_4$, and concentrated. The resulting residue was separated by a silica gel column chromatography (petroleum ether/ethyl acetate=2:1) to produce a pale yellow solid 6(c) (520 mg, 74%).

3) Synthesis of Compound 6(e)

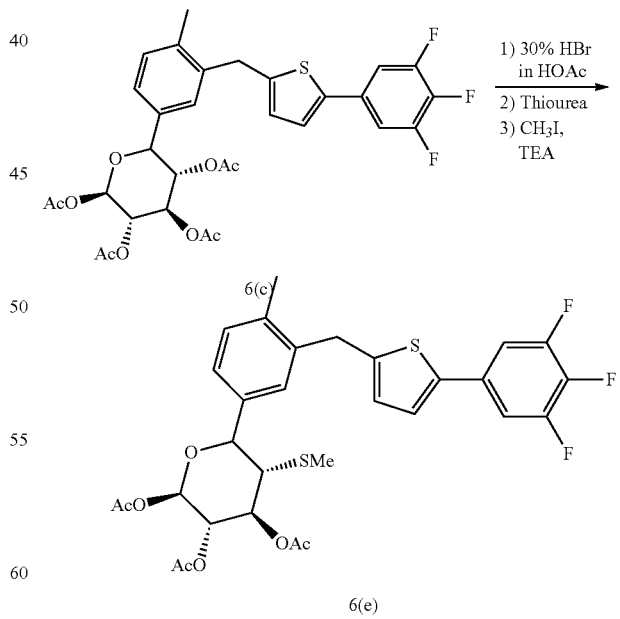

Under an ice-water bath, to a single-neck bottle containing Compound 6(c) (429 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 6(e) (269 mg, 64% (three steps)).

$^1$H NMR (400 Hz, CDCl$_3$) δ1.79 (s, 3H), 2.03 (s, 3H), 2.12 (s, 3H), 2.20 (s, 3H), 2.31 (s, 3H), 4.13 (s, 2H), 4.44 (d, J=9.6 Hz, 1H), 4.55 (d, J=9.6 Hz, 1H), 5.15 (t, J=9.6 Hz, 1H), 5.24 (d, J=9.6 Hz, 1H), 5.34 (t, J=9.6 Hz, 1H), 6.66 (d, J=3.6 Hz, 1H), 7.07 (d, J=3.6 Hz, 1H), 7.11-7.20 (m, 5H).

4) Synthesis of Compound 6

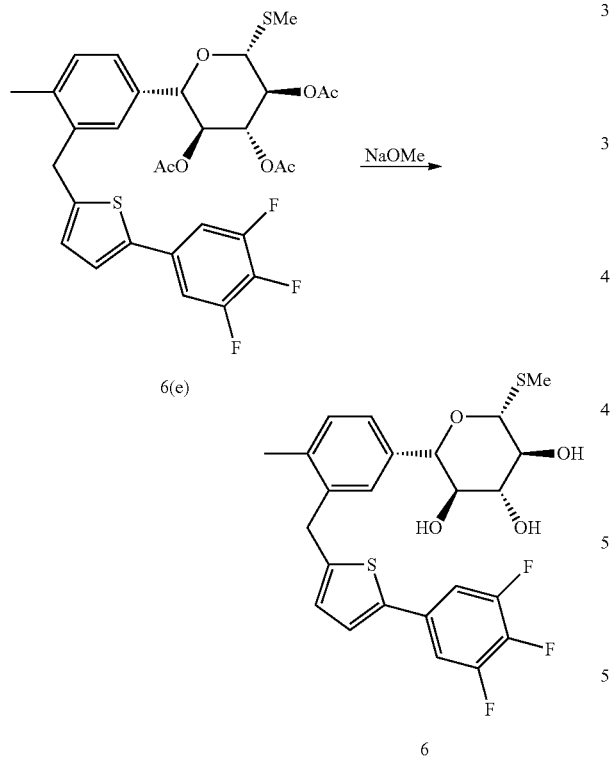

6

Compound 6(e) (258 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 6 (166 mg, 81%).

$^1$H NMR (400 Hz, CDCl$_3$) δ2.22 (s, 3H), 2.33 (s, 3H), 2.78 (s, 1H), 3.24 (s, 1H), 3.58-3.62 (m, 2H), 3.71-3.74 (m, 1H), 4.15 (s, 2H), 4.23 (d, J=8.4 Hz, 1H), 4.42 (d, J=9.2 Hz, 1H), 6.71 (s, 1H), 7.07-7.26 (m, 6H).

ESI(+)m/z: 496.1

Example 7

Synthesis of (2S,3R,4R,5S,6R)-2-[3-((5-(3,4-difluorophenyl)thienyl)-2-methylene)-4-methylphenyl)-6-methylthio-tetrahydropyran-3,4,5-triol

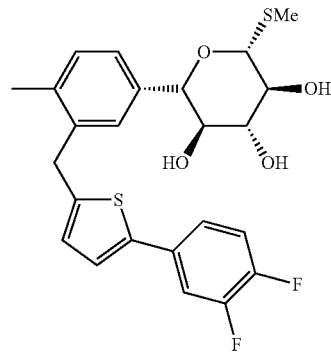

7

1) Synthesis of Compound 7(b)

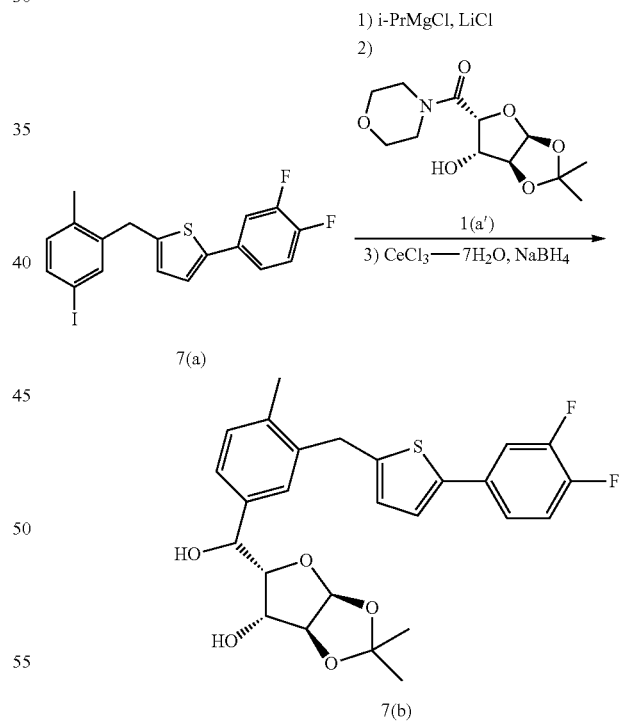

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 7(a) (4.4 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH₄Cl solution. The aqueous phase was removed and extracted with ethyl acetate. The organic phases were combined, washed with water and a saturated aqueous NaCl solution successively, dried with anhydrous Na₂SO₄ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl₃.7H₂O (490 mg, 1.32 mmol) was added at room temperature. The mixture was stirred for 20 mins until it completely dissolved, and cooled to −78° C. NaBH₄ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na₂SO₄, and concentrated to produce a crude pale yellow oily product 7(b).

2) Synthesis of Compound 7(c)

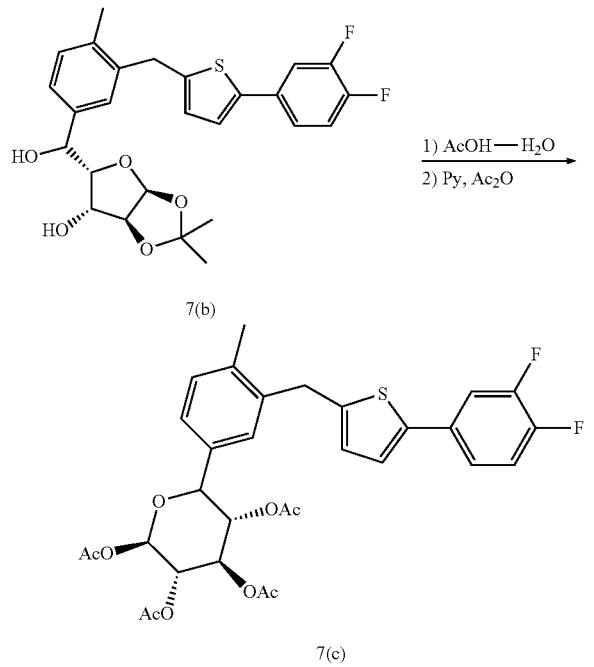

The crude Compound 7(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac₂O (0.5 mL) were added slowly under an ice-water bath cooling. After the completion of the addition, the mixture was stirred at room temperature for 2 hrs. A saturated aqueous NaHCO₃ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na₂SO₄, and concentrated. The resulting residue was separated by a silica gel column chromatography (petroleum ether/ethyl acetate=2:1) to produce a pale yellow solid 7(c) (515 mg, 76%).

3) Synthesis of Compound 7(e)

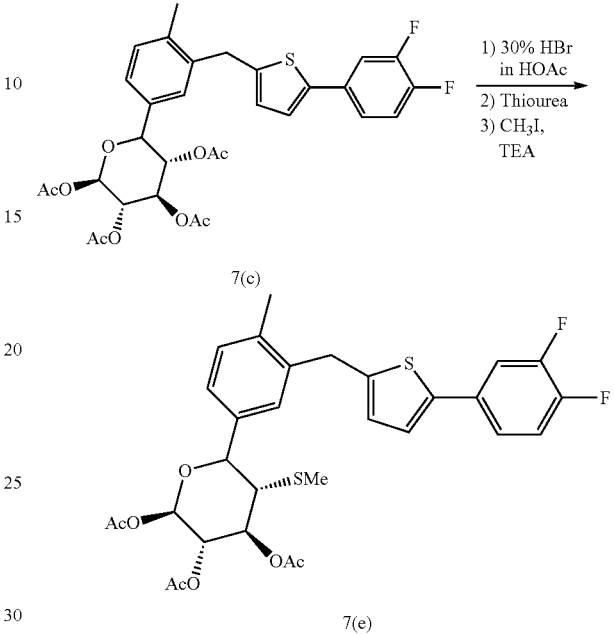

Under an ice-water bath, to a single-neck bottle containing Compound 7(c) (416 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO₃ solution. The organic phase was separated. The aqueous phase was extracted with dichloromethane (3×10 mL). The organic phases were combined, washed with water and a saturated aqueous NaCl solution successively, dried with anhydrous Na₂SO₄, and concentrated to produce a pale yellow liquid.

At room temperature, to the above resulting pale yellow liquid, 8 mL MeCN and 154 mg S(NH₂)₂ were added. The mixture was heated under reflux for 1 hr, and then cooled to room temperature. Et₃N (4 eq) and CH₃I (3 eq) were added. The mixture was stirred for 1 hr. The reaction was quenched with a saturated aqueous NaHCO₃ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na₂SO₄, and concentrated. The resulting residue was purified by a silica gel column chromatography (petroleum ether/ethyl acetate=5:1) to produce a pale yellow solid 7(e) (258 mg, 63% (three steps)).

¹H NMR (400 Hz, CDCl₃) δ1.79 (s, 3H), 2.03 (s, 3H), 2.12 (s, 3H), 2.19 (s, 3H), 2.31 (s, 3H), 4.12 (s, 2H), 4.43 (d, J=9.6 Hz, 1H), 4.54 (d, J=9.6 Hz, 1H), 5.14 (t, J=9.6 Hz, 1H), 5.23 (d, J=9.6 Hz, 1H), 5.36 (t, J=9.6 Hz, 1H), 6.65 (d, J=4 Hz, 1H), 7.07 (d, J=4 Hz, 1H), 7.13-7.36 (m, 6H).

4) Synthesis of Compound 7

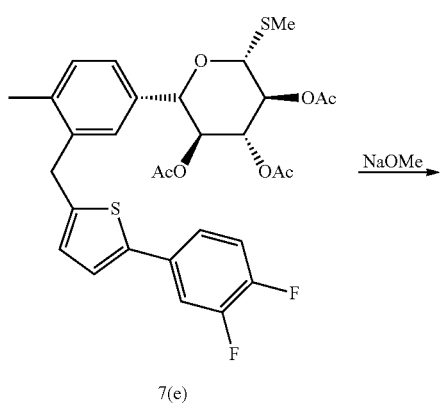

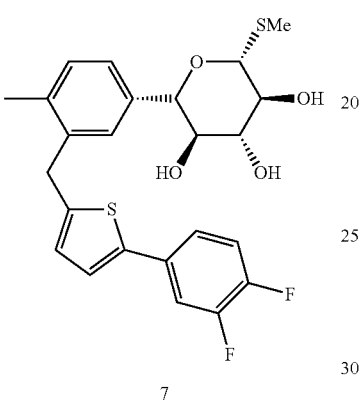

Compound 7(e) (250 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 7 (176 mg, 89%).

$^1$H NMR (400 Hz, CDCl$_3$) δ2.13 (s, 1H), 2.23 (s, 3H), 2.33 (s, 3H), 2.63 (s, 1H), 2.98 (s, 1H), 3.59-3.63 (m, 2H), 3.75 (t, J=8.4 Hz, 1H), 4.16 (s, 2H), 4.24 (d, J=9.2 Hz, 1H), 4.43 (d, J=10 Hz, 1H), 6.71 (d, J=3.6 Hz, 1H), 7.06 (d, J=3.6 Hz, 1H), 7.13-7.35 (m, 6H).

ESI(+)m/z: 478.1

Example 8

Synthesis of (2S,3R,4R,5S,6R)-2-[3-((5-(4-methoxyphenyl)thienyl)-2-methylene)-4-methylphenyl)-6-methylthio-tetrahydropyran-3,4,5-triol

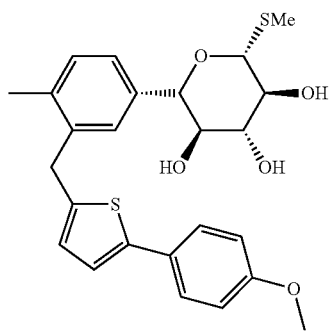

1) Synthesis of Compound 8(b)

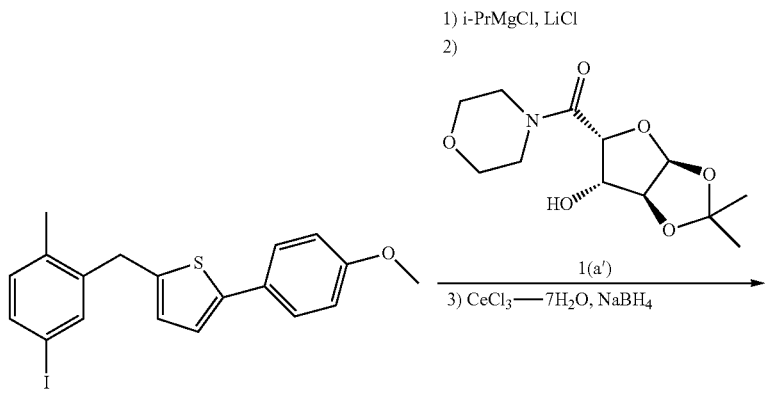

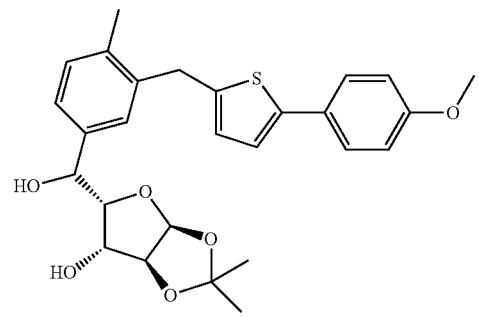

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 8(a) (3.9 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 8(b).

2) Synthesis of Compound 8(c)

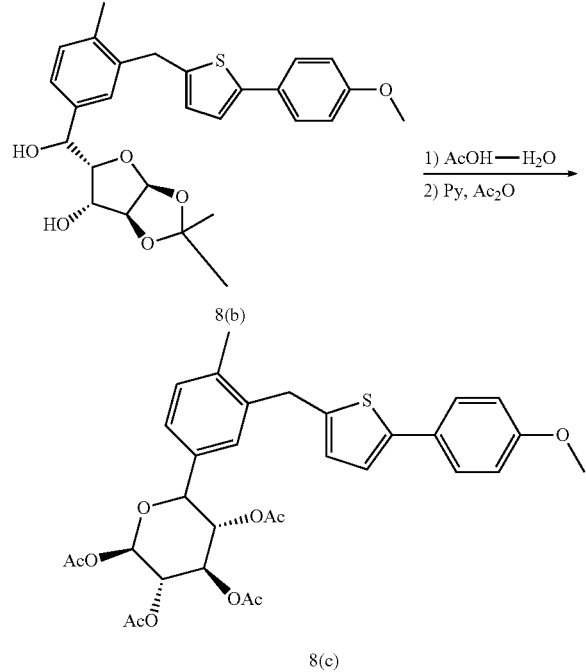

The crude Compound 8(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 8(c) (503 mg, 75%).

3) Synthesis of Compound 8(e)

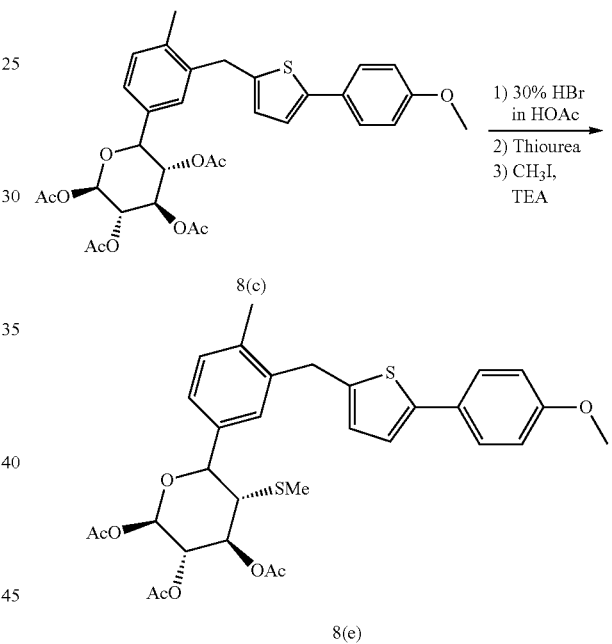

Under an ice-water bath, to a single-neck bottle containing Compound 8(c) (413 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na₂SO₄, and concentrated. The resulting residue was purified by a silica gel column chromatography (petroleum ether/ethyl acetate=5:1) to produce a pale yellow solid 8(e) (247 mg, 61% (three steps)).

¹H NMR (400 Hz, CDCl₃) δ1.78 (s, 3H), 2.03 (s, 3H), 2.12 (s, 3H), 2.19 (s, 3H), 2.32 (s, 3H), 3.85 (s, 3H), 4.12 (d, J=2.8 Hz, 2H), 4.44 (d, J=9.6 Hz, 1H), 4.55 (d, J=9.6 Hz, 1H), 5.14 (t, J=9.8 Hz, 1H), 5.24 (t, J=9.6 Hz, 1H), 5.36 (t, J=9.6 Hz, 1H), 6.64 (d, J=3.2 Hz, 1H), 6.80-6.82 ((m, 1H), 7.07-7.30 (m, 7H).

4) Synthesis of Compound 8

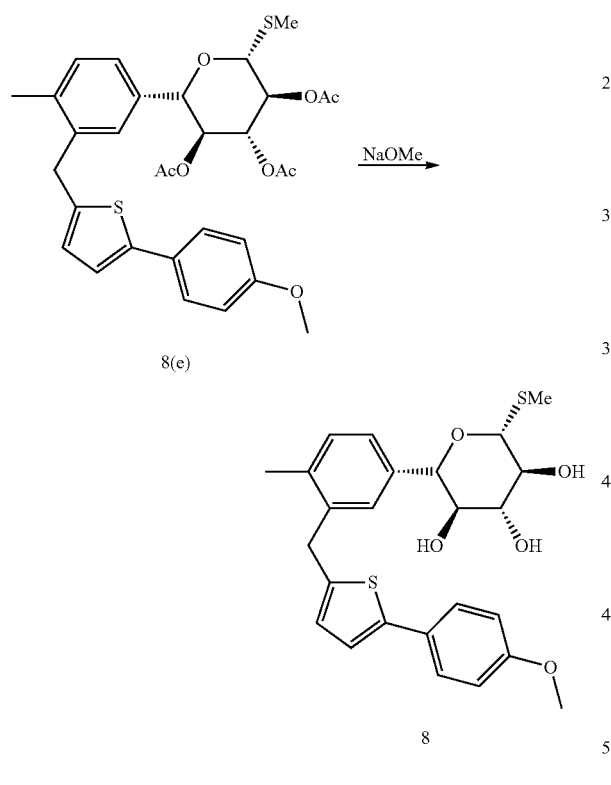

Compound 8(e) (248 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 8 (158 mg, 81%).

¹H NMR (400 Hz, CDCl₃) δ2.19 (s, 3H), 2.32 (s, 3H), 3.68-3.72 (m, 2H), 3.76-3.81 (m, 1H), 3.85 (s, 3H), 4.15 (s, 2H), 4.25 (d, J=8.6 Hz, 1H), 4.45 (d, J=9.6 Hz, 1H), 6.64 (d, J=3.2 Hz, 1H), 6.80-6.82 ((m, 1H), 7.07-7.30 (m, 7H).

ESI(+)m/z: 472.1

Example 9

Synthesis of (2S,3R,4R,5S,6R)-2-[3-((5-(3-cynaophenyl)thienyl)-2-methylene)-4-methylphenyl)-6-methylthio-tetrahydropyran-3,4,5-triol

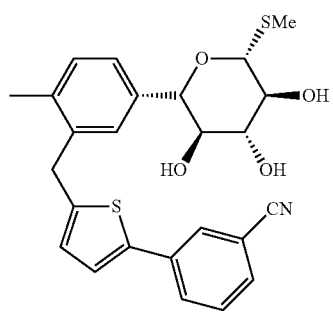

1) Synthesis of Compound 9(b)

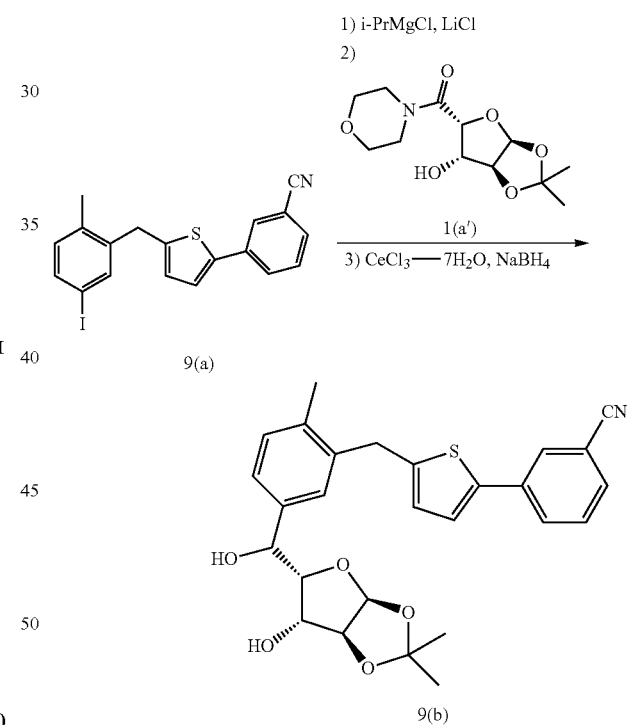

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 9(a) (3.9 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH₄Cl solution. The aqueous phase was removed and extracted with ethyl acetate. The organic phases were combined, washed with water and a saturated aqueous NaCl solution successively, dried with anhydrous $Na_2SO_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). $CeCl_3.7H_2O$ (490 mg, 1.32 mmol) was added at room temperature. The mixture was stirred for 20 mins until it completely dissolved, and cooled to −78° C. $NaBH_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous $Na_2SO_4$, and concentrated to produce a crude pale yellow oily product 9(b).

2) Synthesis of Compound 9(c)

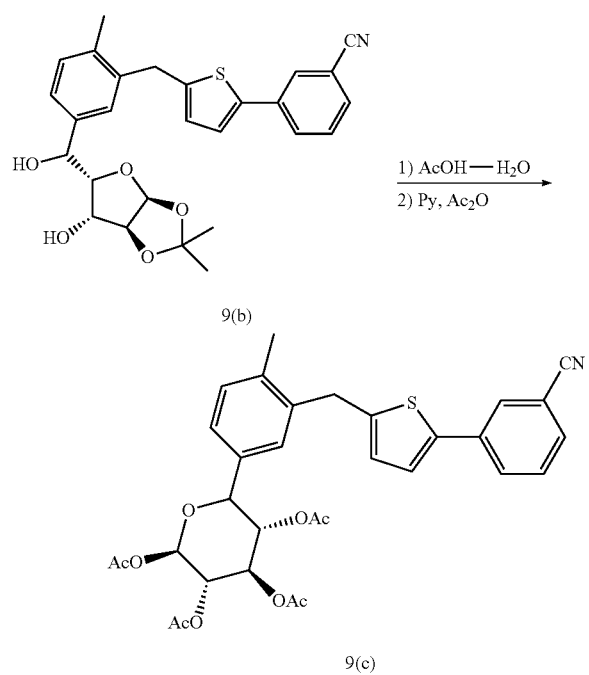

The crude Compound 9(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and $Ac_2O$ (0.5 mL) were added slowly under an ice-water bath cooling. After the completion of the addition, the mixture was stirred at room temperature for 2 hrs. A saturated aqueous $NaHCO_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous $Na_2SO_4$, and concentrated. The resulting residue was separated by a silica gel column chromatography (petroleum ether/ethyl acetate=2:1) to produce a pale yellow solid 9(c) (519 mg, 78%).

3) Synthesis of Compound 9(e)

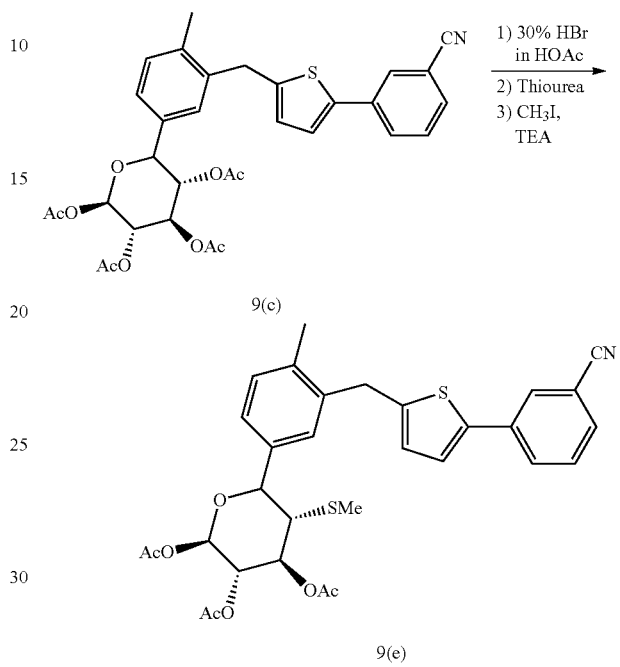

Under an ice-water bath, to a single-neck bottle containing Compound 9(c) (418 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous $NaHCO_3$ solution. The organic phase was separated. The aqueous phase was extracted with dichloromethane (3×10 mL). The organic phases were combined, washed with water and a saturated aqueous NaCl solution successively, dried with anhydrous $Na_2SO_4$, and concentrated to produce a pale yellow liquid.

At room temperature, to the above resulting pale yellow liquid, 8 mL MeCN and 154 mg $S(NH_2)_2$ were added. The mixture was heated under reflux for 1 hr, and then cooled to room temperature. $Et_3N$ (4 eq) and $CH_3I$ (3 eq) were added. The mixture was stirred for 1 hr. The reaction was quenched with a saturated aqueous $NaHCO_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous $Na_2SO_4$, and concentrated. The resulting residue was purified by a silica gel column chromatography (petroleum ether/ethyl acetate=5:1) to produce a pale yellow solid 9(e) (253 mg, 63% (three steps)).

$^1$H NMR (400 Hz, $CDCl_3$) δ1.80 (s, 3H), 2.03 (s, 3H), 2.12 (s, 3H), 2.20 (s, 3H), 2.32 (s, 3H), 4.15 (s, 2H), 4.44 (d, J=9.2 Hz, 1H), 4.55 (d, J=9.6 Hz, 1H), 5.15 (t, J=9.6 Hz, 1H), 5.24 (t, J=9.6 Hz, 1H), 5.36 (t, J=9.6 Hz, 1H), 6.70 (d, J=3.6 Hz, 1H), 7.17-7.20 (m, 4H), 7.44-7.53 (m, 2H), 7.75 (d, J=8 Hz, 1H), 7.81 (s, 1H).

4) Synthesis of Compound 9

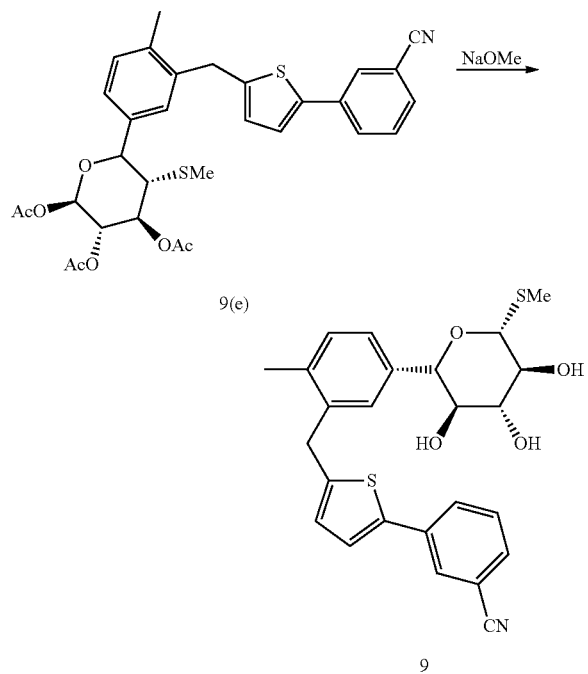

1) Synthesis of Compound 10(b)

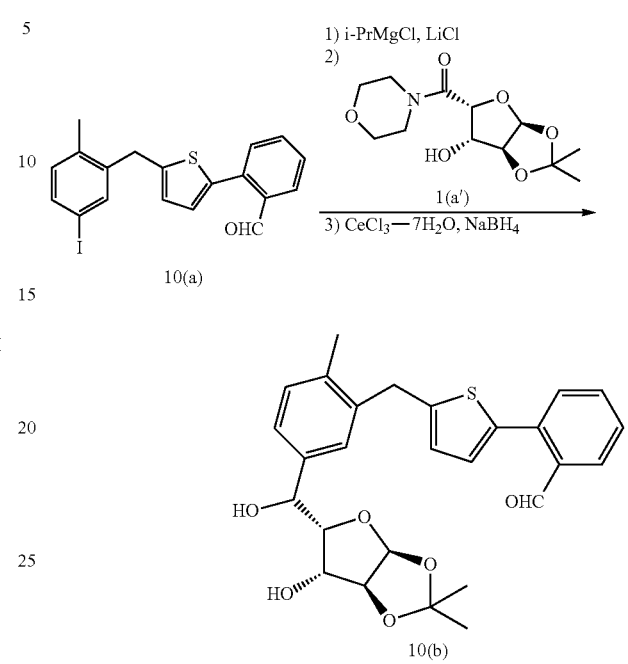

Compound 9(e) (245 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 9 (170 mg, 88%).

$^1$H NMR (400 Hz, CDCl$_3$) δ2.20 (s, 3H), 2.32 (s, 3H), 3.64-3.68 (m, 2H), 3.77-3.81 (m, 1H), 4.15 (s, 2H), 4.25 (d, J=8.6 Hz, 1H), 4.45 (d, J=9.6 Hz, 1H), 6.73 (d, J=3.8 Hz, 1H), 7.15-7.18 (m, 4H), 7.44-7.53 (m, 2H), 7.75 (d, J=8 Hz, 1H), 7.81 (s, 1H).

ESI(+)m/z: 467.1

Example 10

Synthesis of (2S,3R,4R,5S,6R)-2-[3-((5-(2-formylphenyl)thienyl)-2-methylene)-4-methylphenyl)-6-methylthio-tetrahydropyran-3,4,5-triol

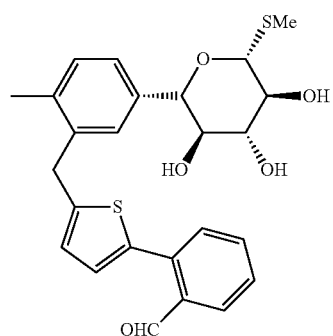

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 10(a) (3.3 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 10(b).

2) Synthesis of Compound 10(c)

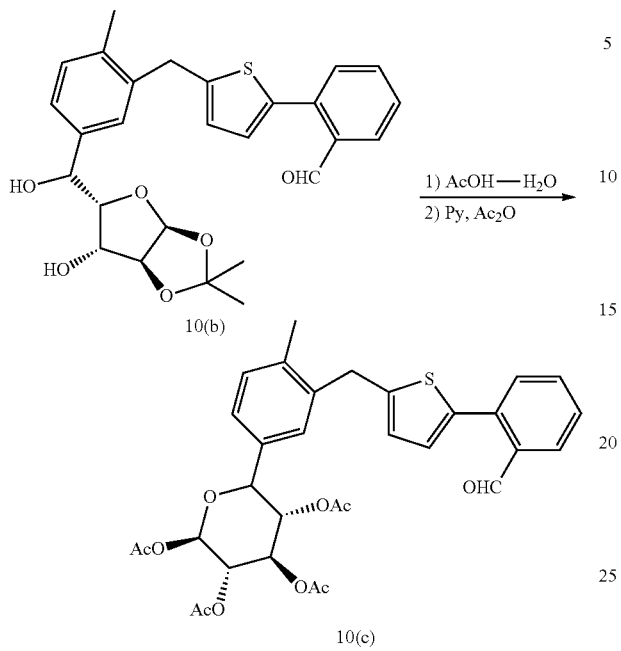

The crude Compound 10(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 10(c) (516 mg, 77%).

3) Synthesis of Compound 10(e)

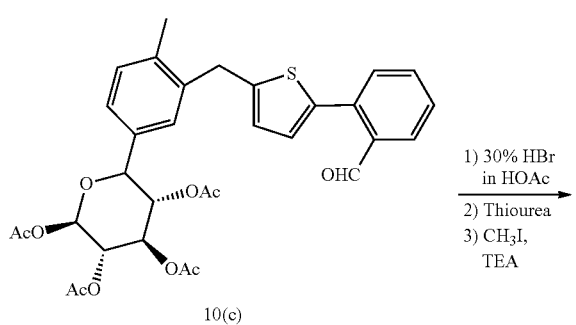

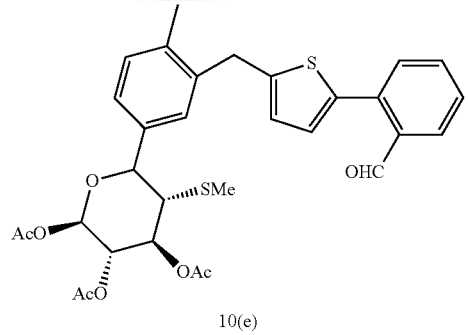

Under an ice-water bath, to a single-neck bottle containing Compound 10(c) (418 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 10(e) (266 mg, 66% (three steps)).

$^1$H NMR (400 Hz, CDCl$_3$) δ1.79 (s, 3H), 2.03 (s, 3H), 2.12 (s, 3H), 2.20 (s, 3H), 2.33 (s, 3H), 4.18 (s, 2H), 4.44 (d, J=9.6 Hz, 1H), 4.56 (d, J=10 Hz, 1H), 5.16 (t, J=9.8 Hz, 1H), 5.24 (t, J=9.8 Hz, 1H), 5.37 (t, J=9.4 Hz, 1H), 6.72 (d, J=3.6 Hz, 1H), 6.87 (d, J=3.6 Hz, 1H), 7.20-7.22 (m, 3H), 7.46-7.60 (m, 3H), 7.99 (dd, J=8 Hz, J=1.2 Hz 1H), 10.21 (s, 1H)

4) Synthesis of Compound 10

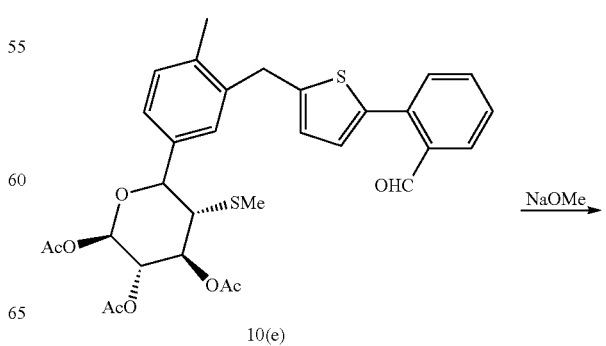

-continued

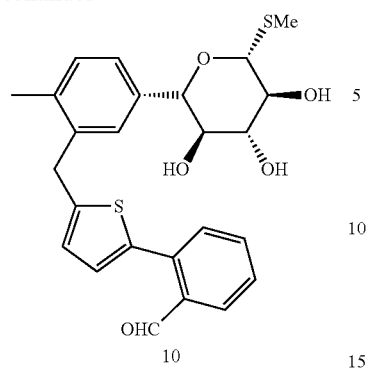

10

-continued

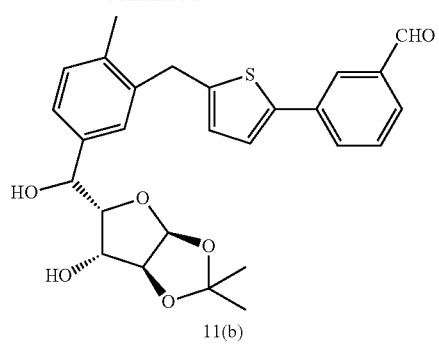

11(b)

Compound 10(e) (247 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 10 (160 mg, 82%).

Example 11

Synthesis of (2S,3R,4R,5S,6R)-2-[3-((5-(3-formylphenyl)thienyl)-2-methylene)-4-methylphenyl)-6-methylthio-tetrahydropyran-3,4,5-triol

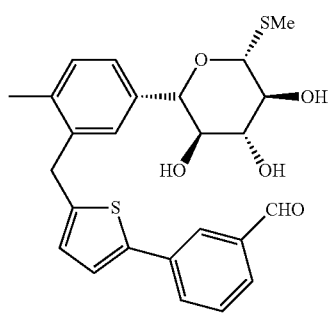

11

1) Synthesis of Compound 11(b)

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 11(a) (4.0 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated $NH_4Cl$ solution. The aqueous phase was removed and extracted with ethyl acetate. The organic phases were combined, washed with water and a saturated aqueous NaCl solution successively, dried with anhydrous $Na_2SO_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). $CeCl_3.7H_2O$ (490 mg, 1.32 mmol) was added at room temperature. The mixture was stirred for 20 mins until it completely dissolved, and cooled to −78° C. $NaBH_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous $Na_2SO_4$, and concentrated to produce a crude pale yellow oily product 11(b).

2) Synthesis of Compound 11(c)

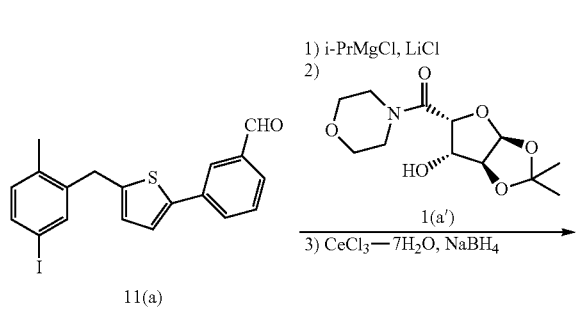

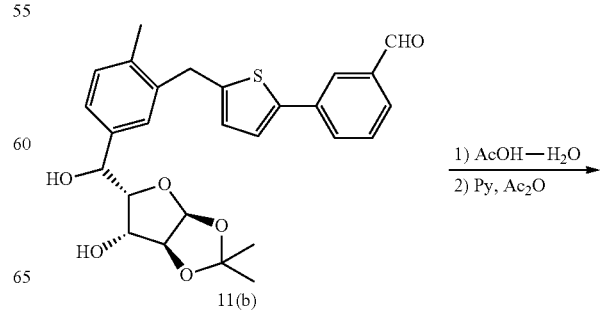

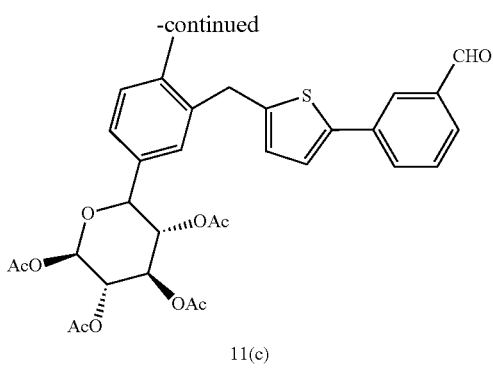

11(c)

The crude Compound 11(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 11(c) (516 mg, 77%).

3) Synthesis of Compound 11(e)

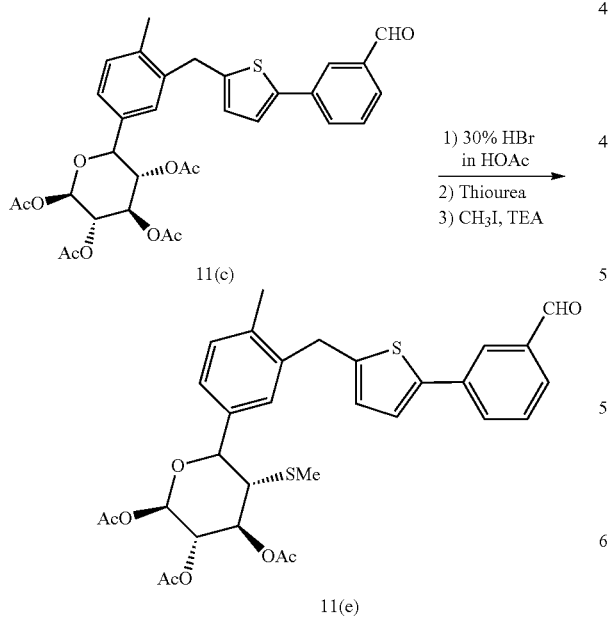

Under an ice-water bath, to a single-neck bottle containing Compound 11(c) (412 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 11(e) (266 mg, 66% (three steps)).

$^1$H NMR (400 Hz, CDCl$_3$) δ1.79 (s, 3H), 2.03 (s, 3H), 2.11 (s, 3H), 2.20 (s, 3H), 2.33 (s, 3H), 4.15 (s, 2H), 4.44 (d, J=9.6 Hz, 1H), 4.56 (d, J=10 Hz, 1H), 5.15 (t, J=9.8 Hz, 1H), 5.24 (t, J=9.8 Hz, 1H), 5.36 (t, J=9.4 Hz, 1H), 6.70 (d, J=3.6 Hz, 1H), 7.19-7.24 (m, 4H), 7.53 (t, J=7.8 Hz, 1H), 7.76 (d, J=7.6 Hz, 1H), 7.79 (d, J=8 Hz, 1H), 8.03 (s, 1H), 10.05 (s, 1H).

4) Synthesis of Compound 11

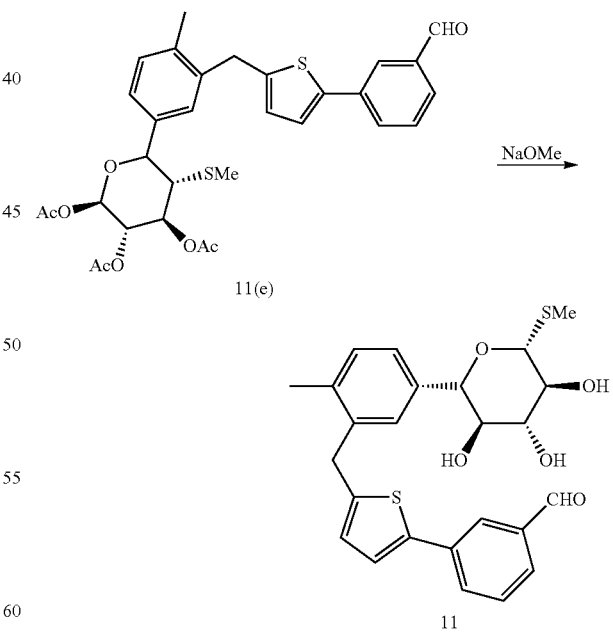

Compound 11(e) (247 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 11 (167 mg, 86%).

¹H NMR (400 Hz, CDCl₃) δ2.20 (s, 3H), 2.33 (s, 3H), 3.66-3.72 (m, 2H), 3.77-3.81 (m, 1H), 4.18 (s, 2H), 4.23 (d, J=8.4 Hz, 1H), 4.45 (d, J=9.2 Hz, 1H), 6.73 (d, J=3.6 Hz, 1H), 7.21-7.26 (m, 4H), 7.55 (t, J=7.8 Hz, 1H), 7.81 (d, J=7.6 Hz, 1H), 7.84 (d, J=8 Hz, 1H), 8.03 (s, 1H), 10.05 (s, 1H).

ESI(+)m/z: 470.1

Example 12

Synthesis of (2S,3R,4R,5S,6R)-2-[3-((5-((4-methylpiperazin-1-yl)methyl)phenyl)thienyl)-2-methylene)-4-methylphenyl)-6-methylthio-tetrahydropyran-3,4,5-triol

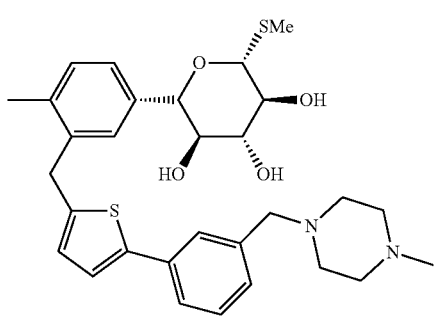

1) Synthesis of Compound 12(b)

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 12(a) (4.7 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH₄Cl solution. The aqueous phase was removed and extracted with ethyl acetate. The organic phases were combined, washed with water and a saturated aqueous NaCl solution successively, dried with anhydrous Na₂SO₄ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl₃.7H₂O (490 mg, 1.32 mmol) was added at room temperature. The mixture was stirred for 20 mins until it completely dissolved, and cooled to −78° C. NaBH₄ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na₂SO₄, and concentrated to produce a crude pale yellow oily product 12(b).

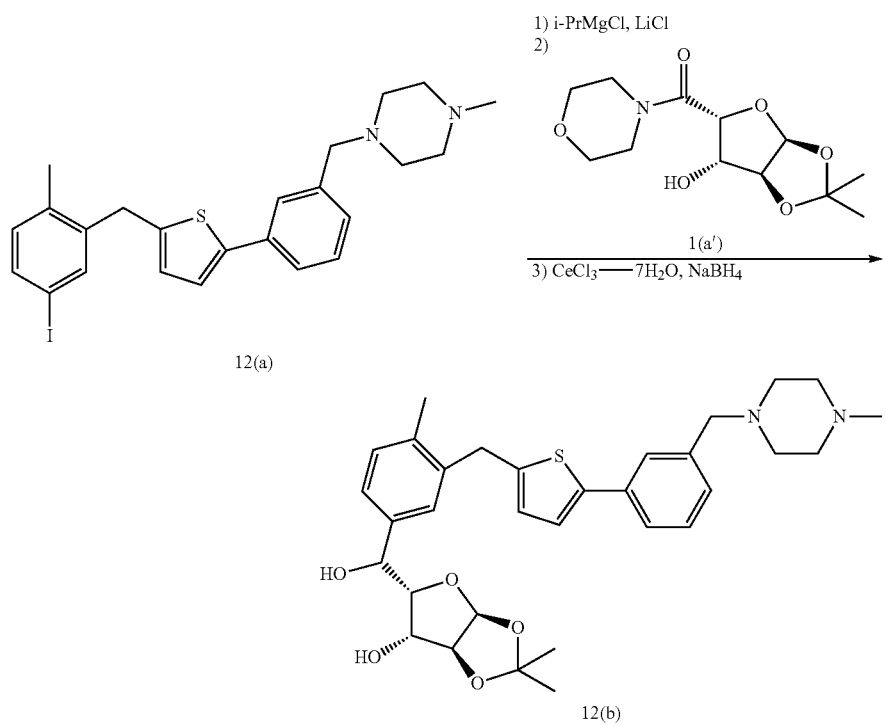

2) Synthesis of Compound 12(c)

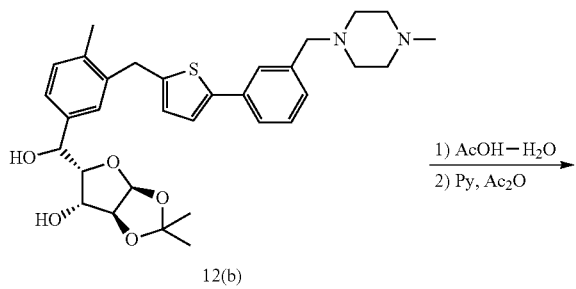

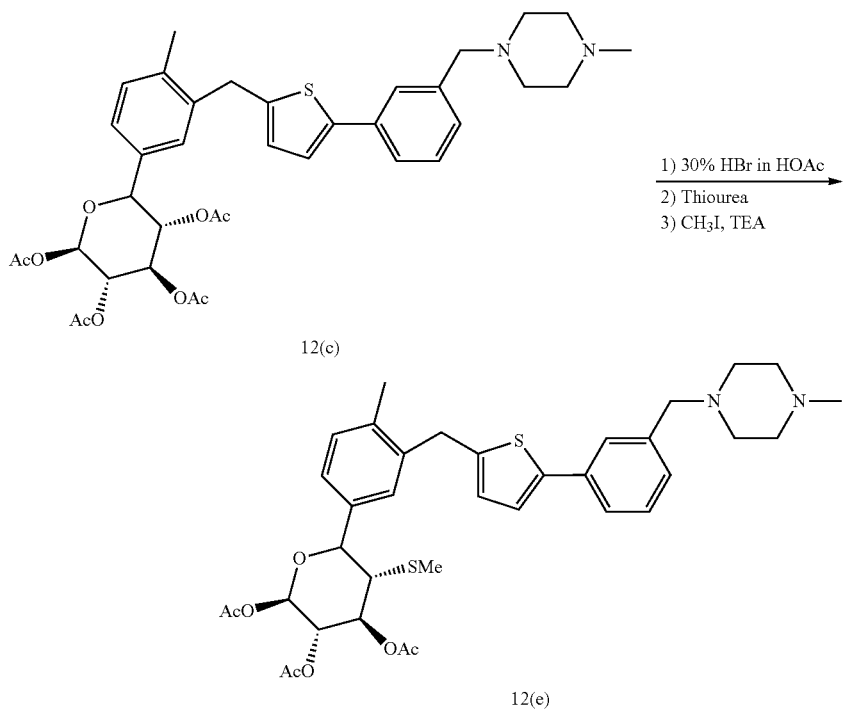

The crude Compound 12(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 12(c) (541 mg, 71%).

3) Synthesis of Compound 12(e)

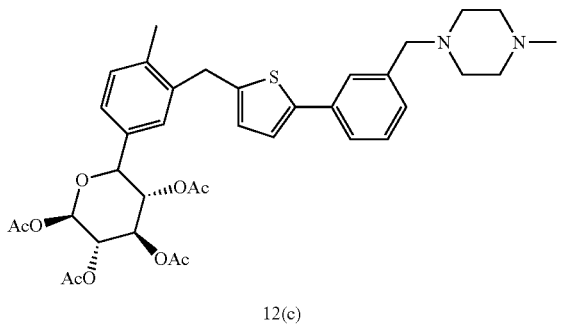

Under an ice-water bath, to a single-neck bottle containing Compound 12(c) (468 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous $Na_2SO_4$, and concentrated. The resulting residue was purified by a silica gel column chromatography (petroleum ether/ethyl acetate=5:1) to produce a pale yellow solid 12(e) (280 mg, 61% (three steps)).

$^1$H NMR (400 Hz, $CDCl_3$) δ1.79 (s, 3H), 2.02 (s, 3H), 2.11 (s, 3H), 2.18 (s, 3H), 2.31 (s, 3H), 2.61 (s, 3H), 2.77 (s, 4H), 2.92 (s, 4H), 3.56 (s, 2H), 4.12 (s, 2H), 4.43 (d, J=9.6 Hz, 1H), 4.54 (d, J=9.6 Hz, 1H), 5.13 (t, J=9.6 Hz, 1H), 5.23 (t, J=9.6 Hz, 1H), 5.35 (t, J=9.4 Hz, 1H), 6.65 (d, J=3.6 Hz, 1H), 7.14-7.21 (m, 5H), 7.31 (d, J=7.6 Hz, 1H), 7.44 (d, J=7.6 Hz, 1H), 7.48 (s, 1H).

4) Synthesis of Compound 12

Compound 12(e) (251 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 12 (202 mg, 88%).

Example 13

Synthesis of (2S,3R,4R,5S,6R)-2-[3-((5-(3-(morpholinylmethyl)phenyl)thienyl)-2-methylene)-4-methylphenyl)-6-methylthio-tetrahydropyran-3,4,5-triol

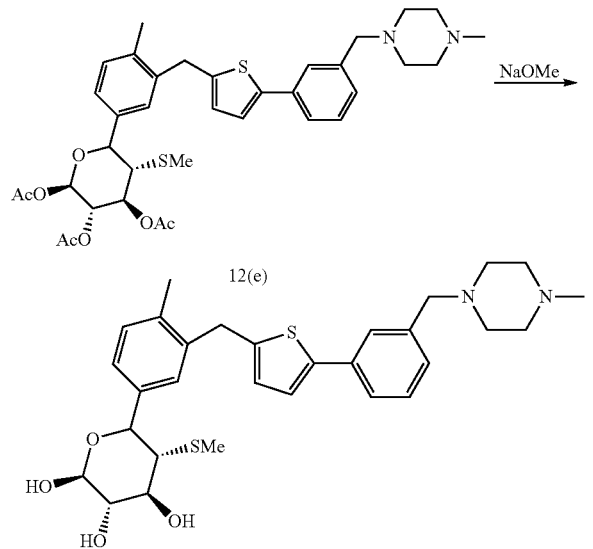

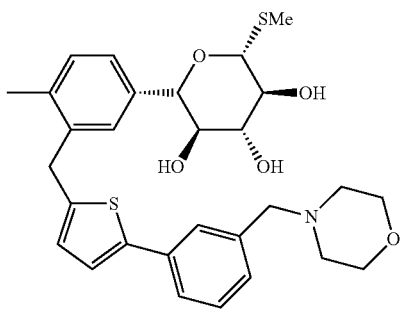

1) Synthesis of Compound 13(b)

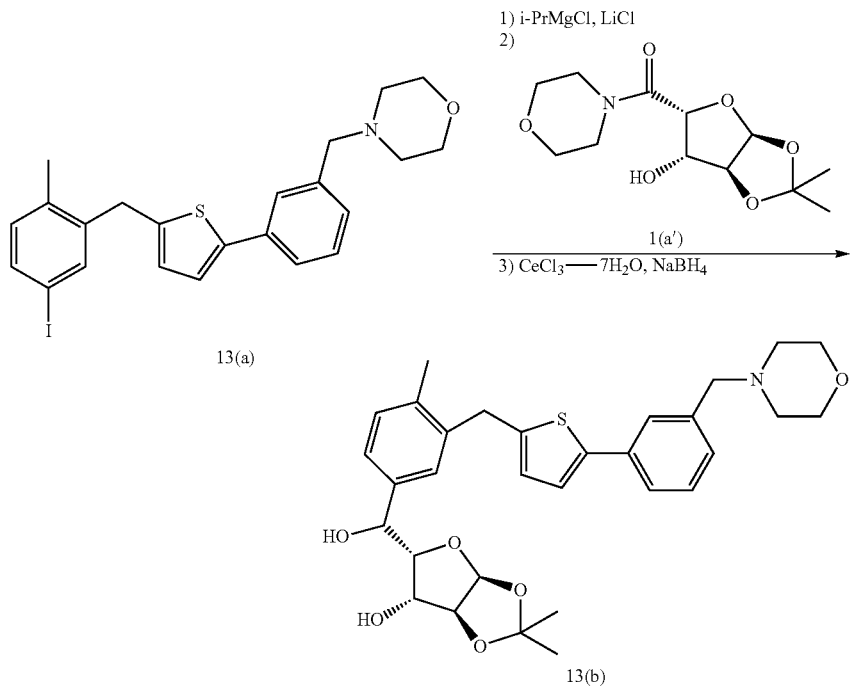

To a single-neck bottle containing LiCl (1.0 g, 23.66 mmol), THF (10 mL) was added, and then 2 mol/L i-PrMgCl/ tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 13(a) (4.6 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 13(b).

2) Synthesis of Compound 13(c)

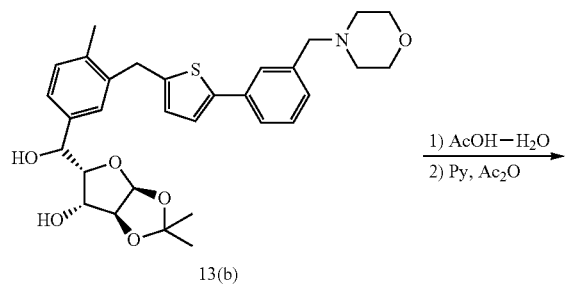

13(b)

1) AcOH—H$_2$O
2) Py, Ac$_2$O

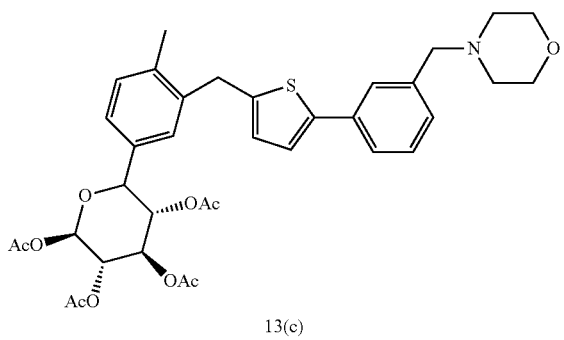

13(c)

The crude Compound 13(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 13(c) (576 mg, 77%).

3) Synthesis of Compound 13(e)

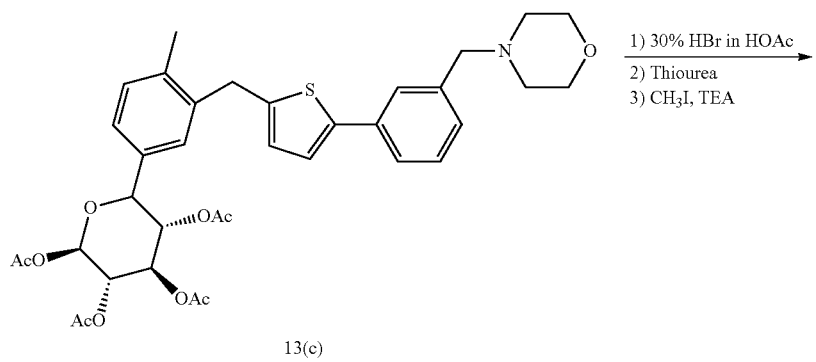

13(c)

1) 30% HBr in HOAc
2) Thiourea
3) CH$_3$I, TEA

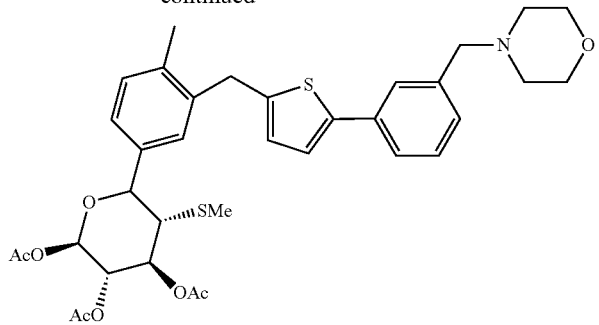

13(e)

Under an ice-water bath, to a single-neck bottle containing Compound 13(c) (460 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 13(e) (284 mg, 63% (three steps)).

$^1$H NMR (400 Hz, CDCl$_3$) δ1.79 (s, 3H), 2.03 (s, 3H), 2.12 (s, 3H), 2.19 (s, 3H), 2.32 (s, 3H), 2.48 (s, 4H), 3.52 (s, 2H), 3.72-3.75 (m, 4H), 4.13 (s, 2H), 4.44 (d, J=10 Hz, 1H), 4.54 (d, J=9.6 Hz, 1H), 5.14 (t, J=9.8 Hz, 1H), 5.24 (t, J=9.6 Hz, 1H), 5.36 (t, J=9.4 Hz, 1H), 6.65 (d, J=3.6 Hz, 1H), 7.14-7.24 (m, 5H), 7.32 (d, J=7.6 Hz, 1H), 7.44 (d, J=8 Hz, 1H), 7.50 (s, 1H).

4) Synthesis of Compound 13

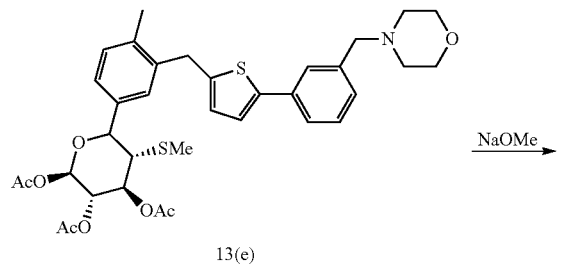

13(e)

NaOMe →

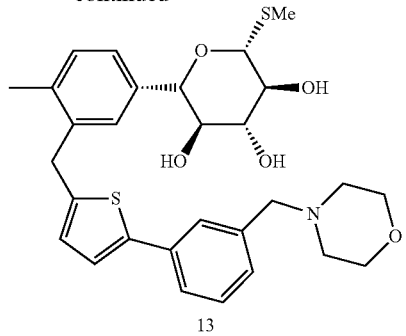

13

Compound 13(e) (277 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 13 (184 mg, 82%).

$^1$H NMR (400 Hz, CDCl$_3$) δ2.19 (s, 3H), 2.32 (s, 3H), 2.48 (s, 4H), 3.52 (s, 2H), 3.65-3.70 (m, 1H), 3.72-3.75 (m, 4H), 3.78-3.85 (m, 1H), 3.90-3.94 (m, 1H), 4.13 (s, 2H), 4.38 (d, J=9.6 Hz, 1H), 4.86 (m, 1H), 6.65 (d, J=3.6 Hz, 1H), 7.14-7.24 (m, 5H), 7.32 (d, J=7.6 Hz, 1H), 7.44 (d, J=8 Hz, 1H), 7.50 (s, 1H).

ESI(+)m/z: 541.7

Example 14

Synthesis of (2S,3R,4R,5S,6R)-2-[3-((5-(4-carboxylphenyl)thienyl)-2-methylene)-4-methylphenyl)-6-methylthio-tetrahydropyran-3,4,5-triol

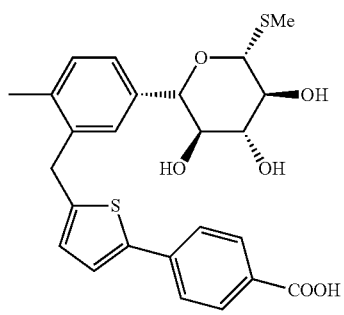

14

1) Synthesis of Compound 14(b)

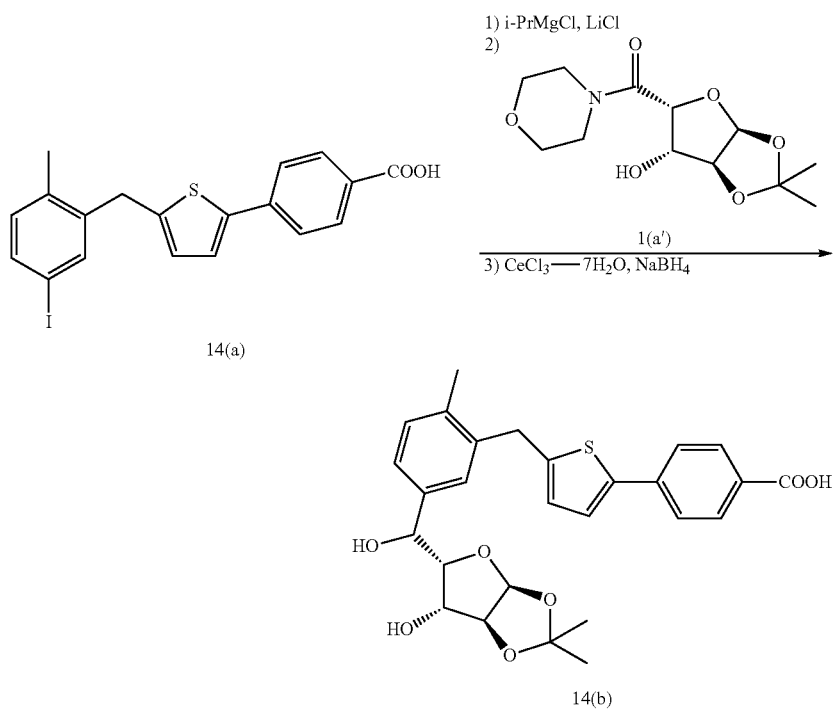

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 14(a) (4.1 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated $NH_4Cl$ solution. The aqueous phase was removed and extracted with ethyl acetate. The organic phases were combined, washed with water and a saturated aqueous NaCl solution successively, dried with anhydrous $Na_2SO_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). $CeCl_3 \cdot 7H_2O$ (490 mg, 1.32 mmol) was added at room temperature. The mixture was stirred for 20 mins until it completely dissolved, and cooled to −78° C. $NaBH_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous $Na_2SO_4$, and concentrated to produce a crude pale yellow oily product 14(b).

2) Synthesis of Compound 14(c)

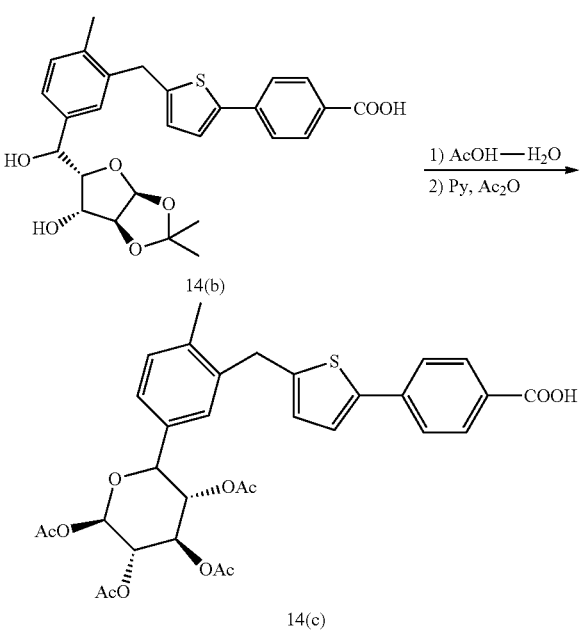

The crude Compound 14(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and $Ac_2O$ (0.5 mL) were added slowly under an ice-water bath cooling. After the completion of the addition, the mixture was stirred at room temperature for 2 hrs. A saturated aqueous NaHCO₃ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na₂SO₄, and concentrated. The resulting residue was separated by a silica gel column chromatography (petroleum ether/ethyl acetate=2:1) to produce a pale yellow solid 14(c) (488 mg, 71%).

3) Synthesis of Compound 14(e)

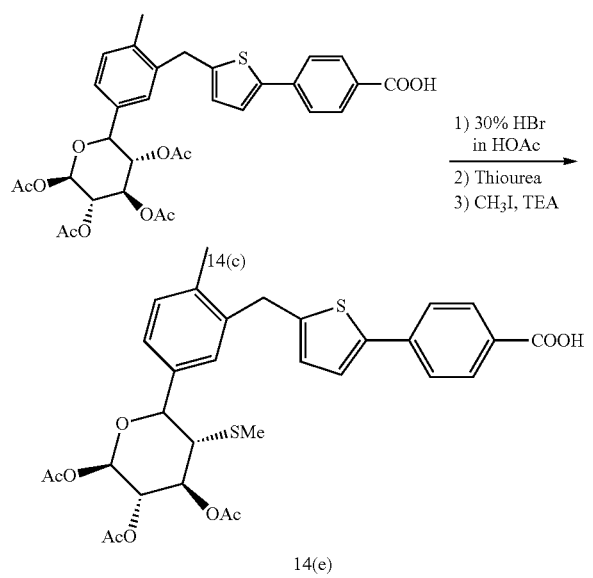

Under an ice cooling, to a single-neck bottle containing Compound 14(c) (423 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO₃ solution. The organic phase was separated. The aqueous phase was extracted with dichloromethane (3×10 mL). The organic phases were combined, washed with water and a saturated aqueous NaCl solution successively, dried with anhydrous Na₂SO₄, and concentrated to produce a pale yellow liquid.

At room temperature, to the above resulting pale yellow liquid, 8 mL MeCN and 154 mg S(NH₂)₂ were added. The mixture was heated under reflux for 1 hr, and then cooled to room temperature. Et₃N (4 eq) and CH₃I (3 eq) were added. The mixture was stirred for 1 hr. The reaction was quenched with a saturated aqueous NaHCO₃ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na₂SO₄, and concentrated. The resulting residue was purified by a silica gel column chromatography (petroleum ether/ethyl acetate=5:1) to produce a pale yellow solid 14(e) (261 mg, 61% (three steps)).

¹H NMR (400 Hz, CDCl₃) δ1.78 (s, 3H), 2.04 (s, 3H), 2.12 (s, 3H), 2.20 (s, 3H), 2.32 (s, 3H), 4.16 (s, 2H), 4.44 (d, J=9.6 Hz, 1H), 4.55 (d, J=9.6 Hz, 1H), 5.14 (t, J=9.8 Hz, 1H), 5.24 (t, J=9.6 Hz, 1H), 5.36 (t, J=9.4 Hz, 1H), 7.00 (s, 1H), 7.20-7.21 (m, 3H), 7.43 (s, 1H), 7.66 (d, J=7.6 Hz, 1H), 8.11 (d, J=8.4 Hz, 1H)

4) Synthesis of Compound 14

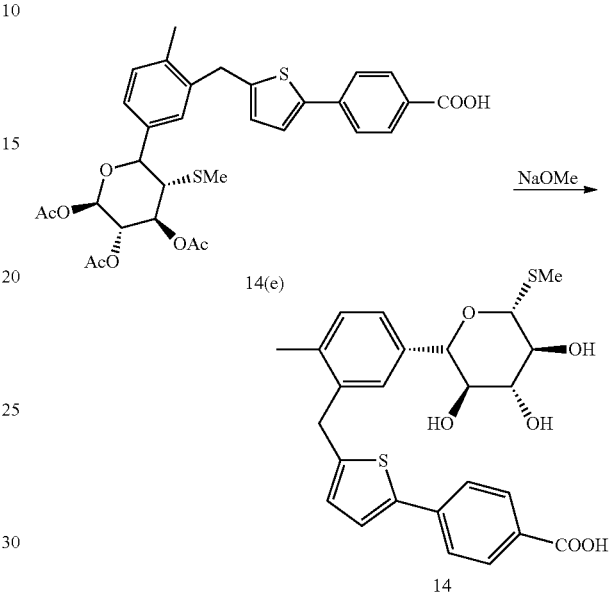

Compound 14(e) (254 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 14 (181 mg, 90%).

Example 15

Synthesis of (2S,3R,4R,5S,6R)-2-[3-((5-(4-N-cyclopropylbenzamide)thienyl)-2-methylene)-4-methylphenyl)-6-methylthio-tetrahydropyran-3,4,5-triol

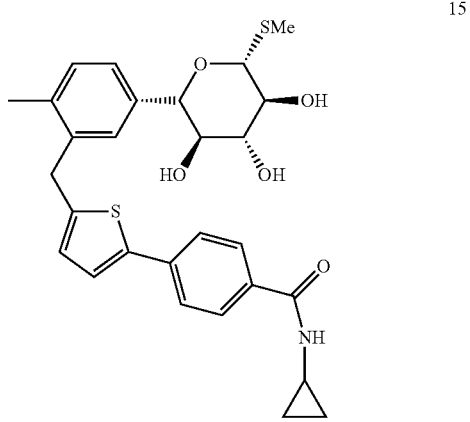

1) Synthesis of Compound 15(b)

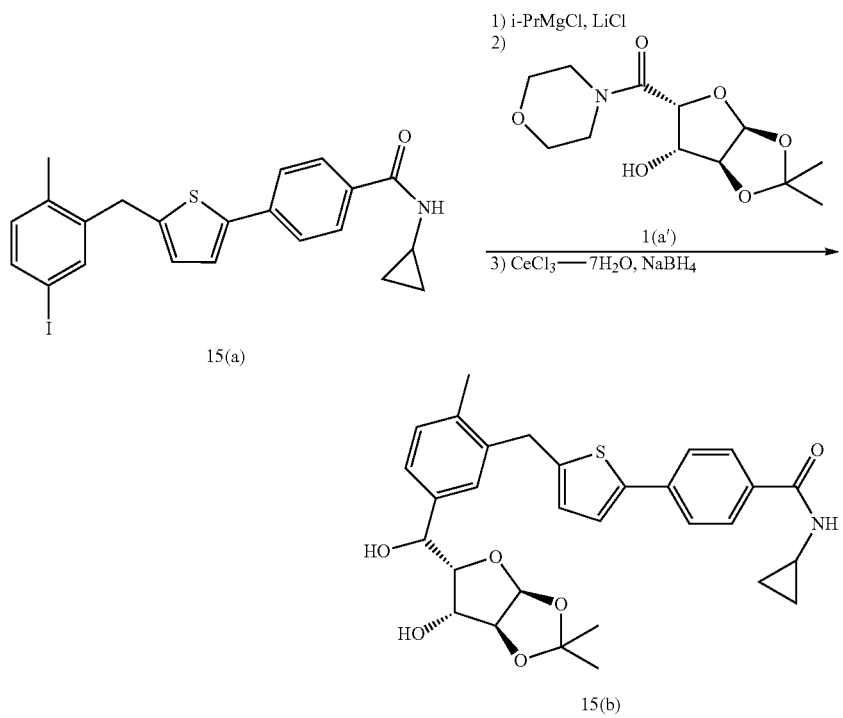

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 15(a) (4.5 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 15(b).

2) Synthesis of Compound 15(c)

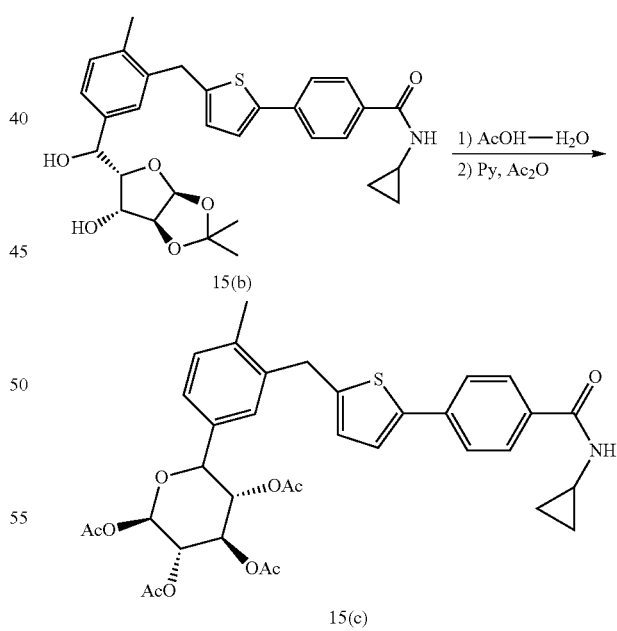

The crude Compound 15(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 15(c) (555 mg, 76%).

3) Synthesis of Compound 15(e)

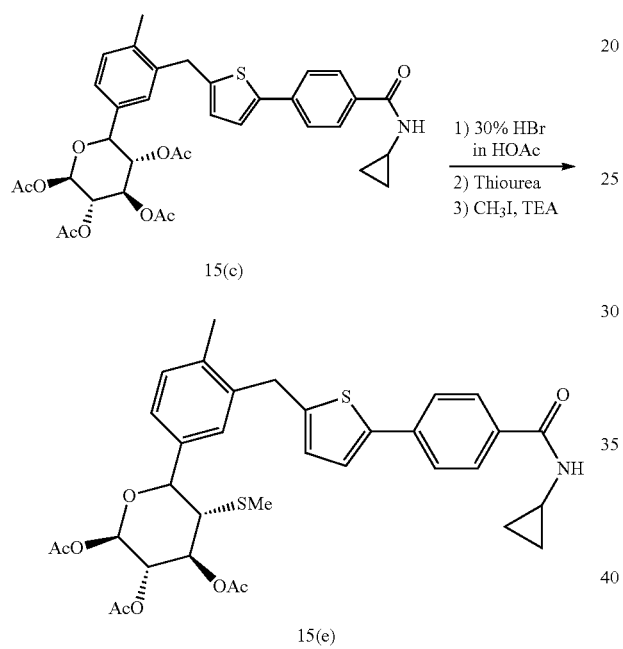

Under an ice-water bath, to a single-neck bottle containing Compound 15(c) (449 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 15(e) (278 mg, 63% (three steps)).

$^1$H NMR (400 Hz, CDCl$_3$) δ0.64 (d, J=8.4 Hz, 2H), 0.88 (d, J=10 Hz, 2H), 1.76 (s, 3H), 2.03 (s, 3H), 2.12 (s, 3H), 2.19 (s, 3H), 2.31 (s, 3H), 2.92-2.94 (m, 1H), 4.15 (s, 2H), 4.43 (d, J=9.6 Hz, 1H), 4.55 (d, J=9.6 Hz, 1H), 5.15 (t, J=9.6 Hz, 1H), 5.23 (t, J=9.8 Hz, 1H), 5.36 (t, J=9.4 Hz, 1H), 6.98 (s, 1H), 7.19-7.22 (m, 3H), 7.36 (s, 1H), 7.62-7.66 (m, 2H), 7.74-7.77 (m, 2H)

4) Synthesis of Compound 15

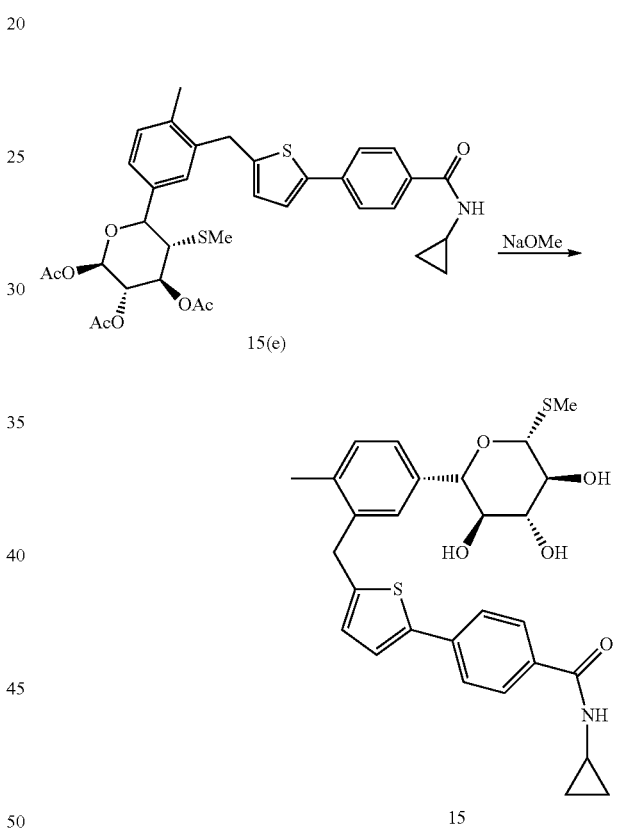

Compound 15(e) (270 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 15 (177 mg, 81%).

$^1$H NMR (400 Hz, CDCl$_3$) δ0.64 (d, J=8.4 Hz, 2H), 0.88 (d, J=10 Hz, 2H), 2.19 (s, 3H), 2.31 (s, 3H), 2.92-2.94 (m, 1H), 3.58-3.62 (m, 2H), 3.71-3.74 (m, 1H), 4.15 (s, 2H), 4.23 (d, J=8.4 Hz, 1H), 4.42 (d, J=9.2 Hz, 1H), 6.98 (s, 1H), 7.23-7.27 (m, 3H), 7.36 (s, 1H), 7.61-7.65 (m, 2H), 7.74-7.78 (m, 2H)

ESI(+)m/z: 526

Example 16

Synthesis of (2S,3R,4R,5S,6R)-2-[3-((5-(4-methylthiophenyl)thienyl)-2-methylene)-4-methylphenyl)-6-methylthio-tetrahydropyran-3,4,5-triol

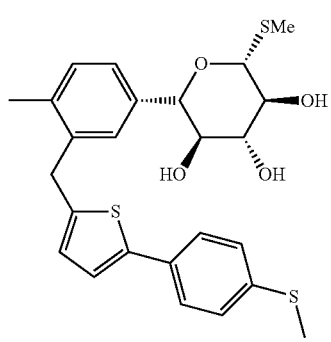

16

1) Synthesis of Compound 16(b)

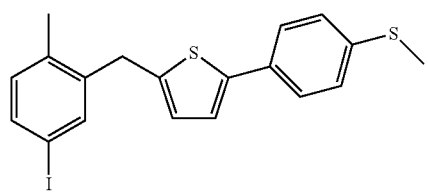

16(a)

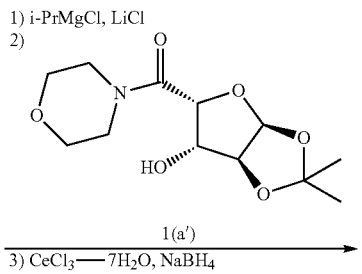

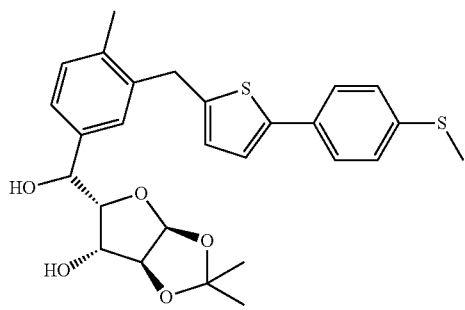

16(b)

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 16(a) (4.1 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 16(b).

2) Synthesis of Compound 16(c)

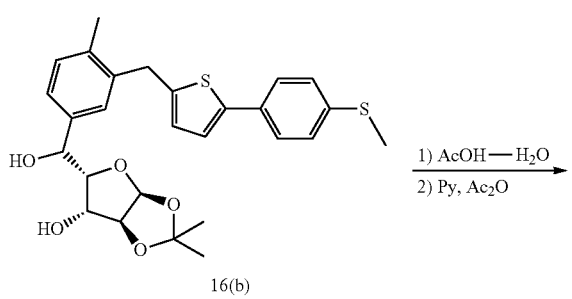

16(b)

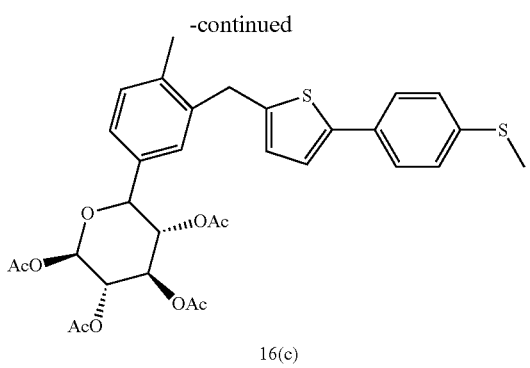

16(c)

The crude Compound 16(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 16(c) (538 mg, 78%).

3) Synthesis of Compound 16(e)

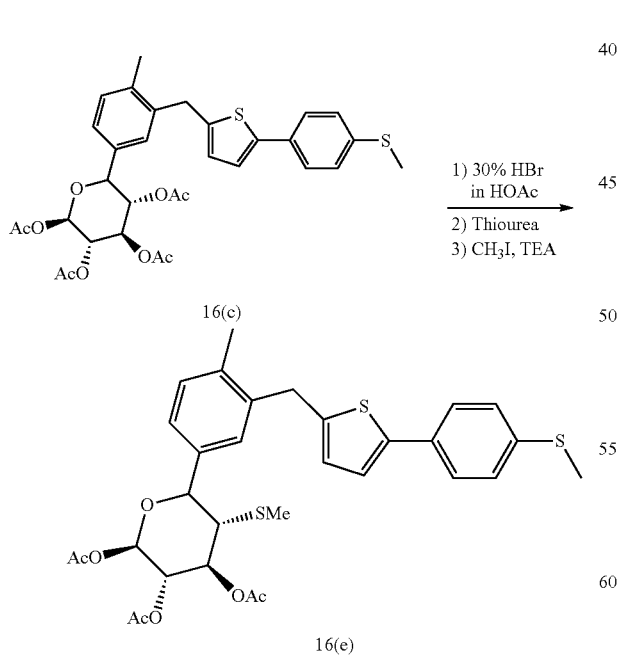

16(c)

16(e)

Under an ice-water bath, to a single-neck bottle containing Compound 16(c) (423 mg, 0.676 mmol), 30% HBr/HOAc solution (3 mL) was added. After the completion of the drop-wise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 16(e) (258 mg, 62% (three steps)).

$^1$H NMR (400 Hz, CDCl$_3$) δ1.78 (s, 3H), 2.03 (s, 3H), 2.12 (s, 3H), 2.19 (s, 3H), 2.32 (s, 3H), 2.51 (s, 3H), 4.12 (d, J=2.4 Hz, 2H), 4.43 (d, J=10 Hz, 1H), 4.54 (d, J=9.6 Hz, 1H), 5.14 (t, J=9.6 Hz, 1H), 5.24 (t, J=9.6 Hz, 1H), 5.36 (t, J=9.4 Hz, 1H), 6.64 (d, J=3.6 Hz, 1H), 7.09 (d, J=3.6 Hz, 1H), 7.17-7.20 (m, 3H), 7.23 (d, J=8.4 Hz, 2H), 7.45 (d, J=8.4 Hz, 2H)

4) Synthesis of Compound 16

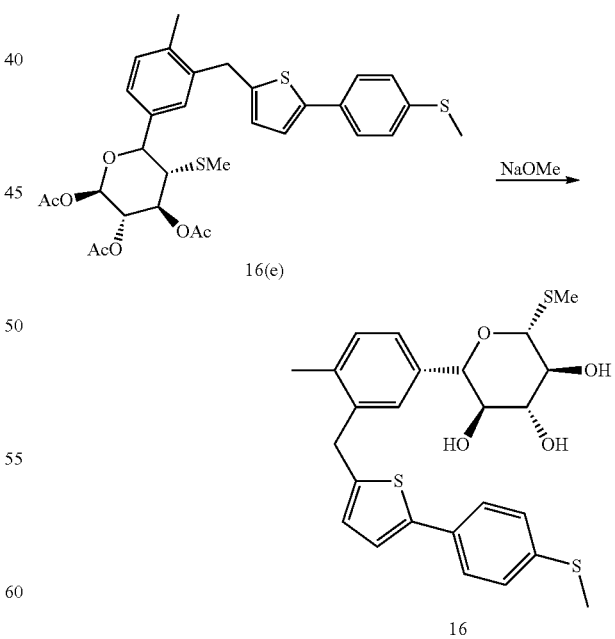

16

Compound 16(e) (255 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 16 (172 mg, 85%).

$^1$H NMR (400 Hz, CDCl$_3$) δ2.19 (s, 3H), 2.32 (s, 3H), 2.51 (s, 3H), 3.68-3.75 (m, 1H), 3.78-3.85 (m, 1H), 3.92-3.97 (m, 1H), 4.23 (s, 2H), 4.44 (d, J=9.6 Hz, 1H), 4.92 (m, 1H), 6.66 (d, J=3.6 Hz, 1H), 7.09 (d, J=3.6 Hz, 1H), 7.18-7.20 (m, 3H), 7.20 (d, J=8.4 Hz, 2H), 7.47 (d, J=8.4 Hz, 2H)

ESI(+)m/z: 489.1

Example 17

Synthesis of (2S,3R,4R,5S,6R)-2-[3-((5-(2-furyl)thienyl)-2-methylene)-4-methylphenyl)-6-methylthio-tetrahydropyran-3,4,5-triol

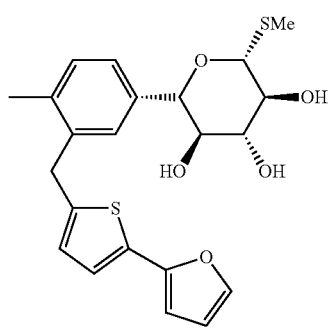

17

1) Synthesis of Compound 17(b)

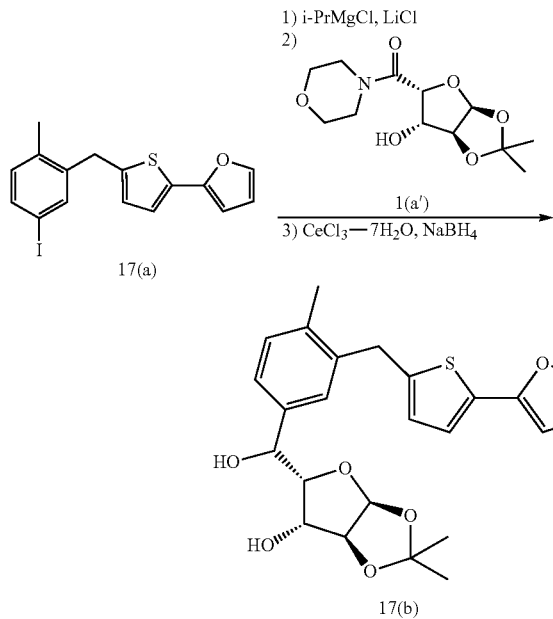

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 17(a) (3.6 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 17(b).

2) Synthesis of Compound 17(c)

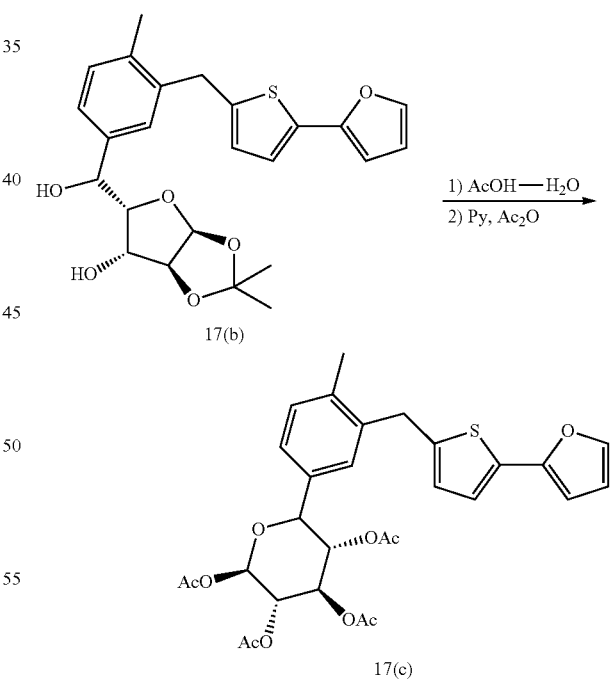

The crude Compound 17(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO₃ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na₂SO₄, and concentrated. The resulting residue was separated by a silica gel column chromatography (petroleum ether/ethyl acetate=2:1) to produce a pale yellow solid 17(c) (465 mg, 74%).

3) Synthesis of Compound 17(e)

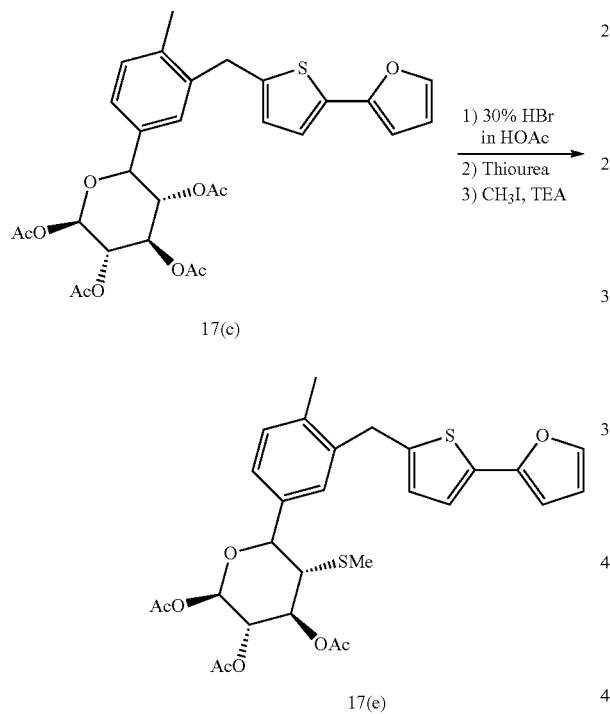

Under an ice-water bath, to a single-neck bottle containing Compound 17(c) (386 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO₃ solution. The organic phase was separated. The aqueous phase was extracted with dichloromethane (3×10 mL). The organic phases were combined, washed with water and a saturated aqueous NaCl solution successively, dried with anhydrous Na₂SO₄, and concentrated to produce a pale yellow liquid.

At room temperature, to the above resulting pale yellow liquid, 8 mL MeCN and 154 mg S(NH₂)₂ were added. The mixture was heated under reflux for 1 hr, and then cooled to room temperature. Et₃N (4 eq) and CH₃I (3 eq) were added. The mixture was stirred for 1 hr. The reaction was quenched with a saturated aqueous NaHCO₃ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na₂SO₄, and concentrated. The resulting residue was purified by a silica gel column chromatography (petroleum ether/ethyl acetate=5:1) to produce a pale yellow solid 17(e) (231 mg, 61% (three steps)).

¹H NMR (400 Hz, CDCl₃) δ1.80 (s, 3H), 2.03 (s, 3H), 2.12 (s, 3H), 2.19 (s, 3H), 2.30 (s, 3H), 4.11 (d, J=4 Hz, 2H), 4.43 (d, J=9.6 Hz, 1H), 4.54 (d, J=10 Hz, 1H), 5.14 (t, J=9.6 Hz, 1H), 5.24 (t, J=9.4 Hz, 1H), 5.36 (t, J=9.4 Hz, 1H), 6.40-6.43 (m, 2H), 6.61 (d, J=4 Hz, 1H), 7.06 (d, J=3.6 Hz, 1H), 7.15-7.21 (m, 2H), 7.36-7.37 (m, 1H).

4) Synthesis of Compound 17

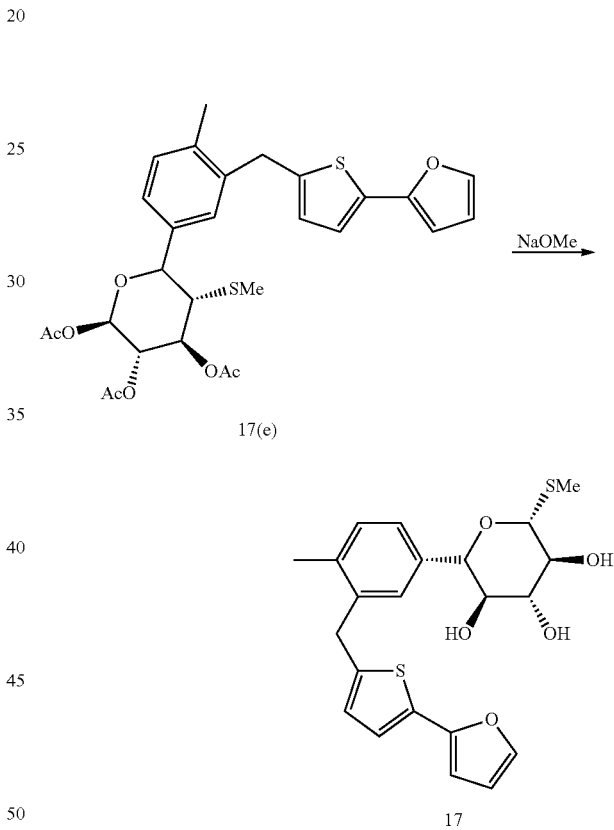

Compound 17(e) (231 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 17 (147 mg, 82%).

¹H NMR (400 Hz, CDCl₃) δ2.19 (s, 3H), 2.30 (s, 3H), 3.60-3.65 (m, 1H), 3.78-3.85 (m, 1H), 3.90-3.94 (m, 1H), 4.18 (s, 2H), 4.38 (d, J=9.6 Hz, 1H), 4.86 (m, 1H), 6.40-6.43 (m, 2H), 6.61 (d, J=4 Hz, 1H), 7.08 (d, J=3.6 Hz, 1H), 7.18-7.24 (m, 2H), 7.33-7.36 (m, 1H).

ESI(+)m/z: 433.1

Example 18

Synthesis of (2S,3R,4R,5S,6R)-2-[3-((5-(4-hydroxymethylphenyl)thienyl)-2-methylene)-4-methylphenyl)-6-methylthio-tetrahydropyran-3,4,5-triol

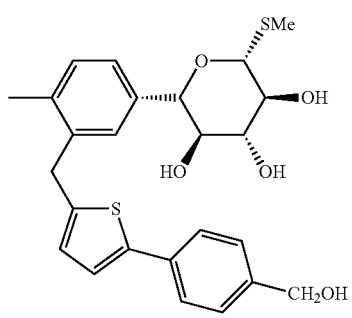

1) Synthesis of Compound 18(b)

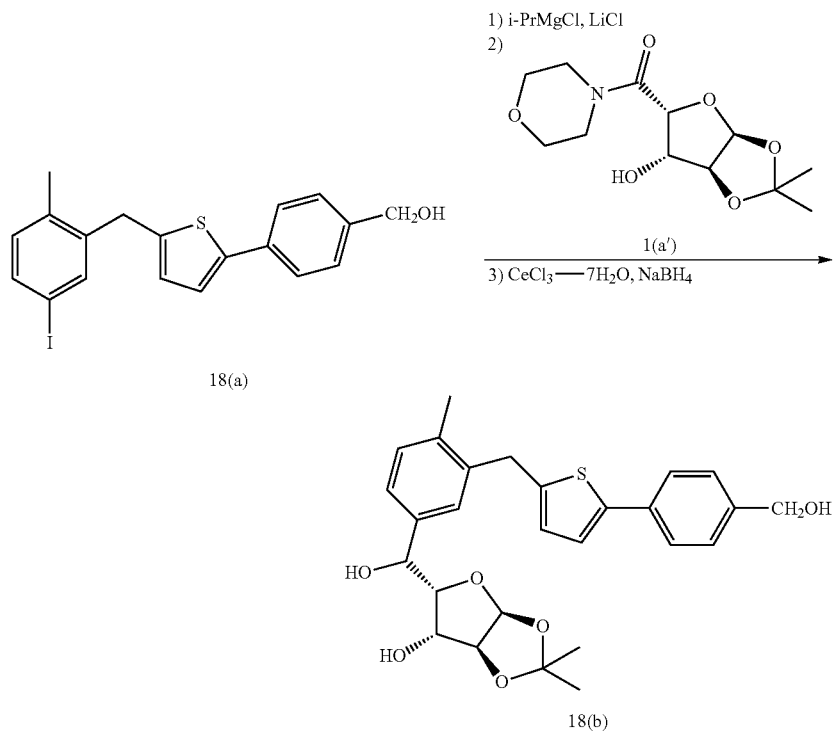

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 18(a) (3.8 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 18(b).

2) Synthesis of Compound 18(c)

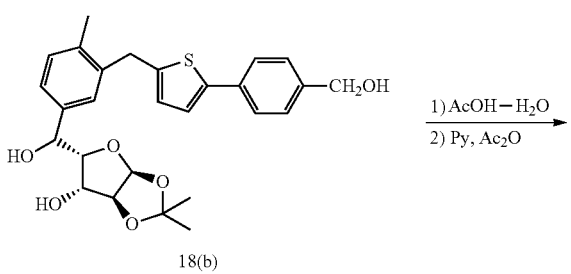

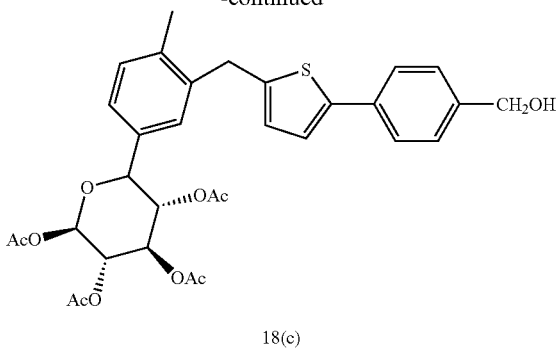

18(c)

The crude Compound 18(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 18(c) (477 mg, 71%).

3) Synthesis of Compound 18(e)

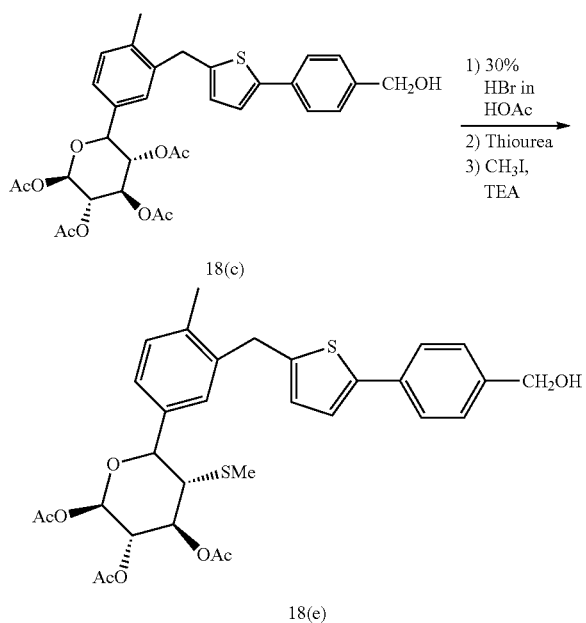

Under an ice-water bath, to a single-neck bottle containing Compound 18(c) (413 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 18(e) (251 mg, 62% (three steps)).

4) Synthesis of Compound 18

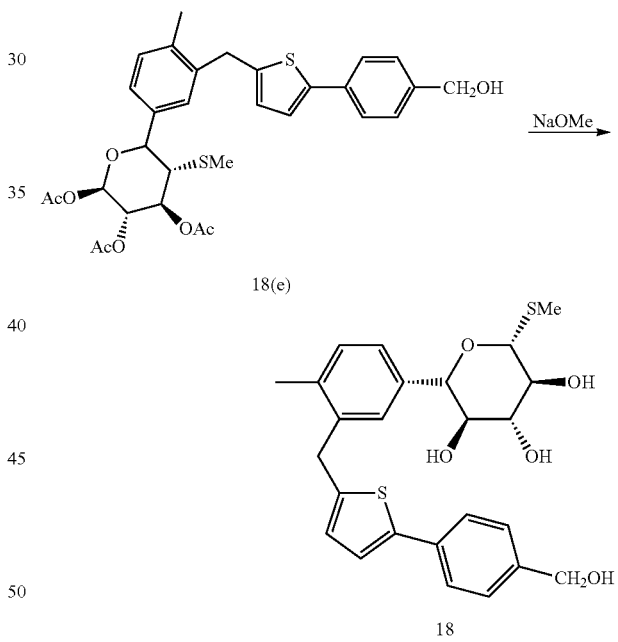

Compound 18(e) (248 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 18 (172 mg, 88%).

$^1$H NMR (400 Hz, CDCl$_3$) δ2.18 (s, 3H), 2.30 (s, 3H), 3.72-3.75 (m, 1H), 3.78-3.85 (m, 1H), 3.88-3.92 (m, 1H), 4.23 (s, 2H), 4.43 (d, J=9.6 Hz, 1H), 4.90 (m, 1H), 6.68 (d, J=3.6 Hz, 1H), 7.20 (d, J=3.6 Hz, 1H), 7.23-7.27 (m, 3H), 7.36 (d, J=8.4 Hz, 2H), 7.58 (d, J=8.4 Hz, 2H).

ESI(+)m/z: 473.1

Example 19

Synthesis of (2S,3R,4R,5S,6R)-2-[3-((5-(3-aminophenyl)thienyl)-2-methylene)-4-methylphenyl)-6-methylthio-tetrahydropyran-3,4,5-triol

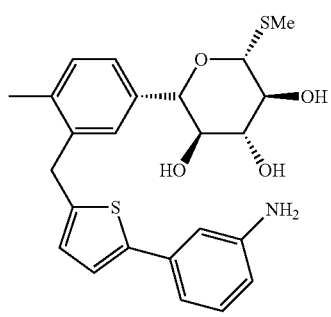

1) Synthesis of Compound 19(b)

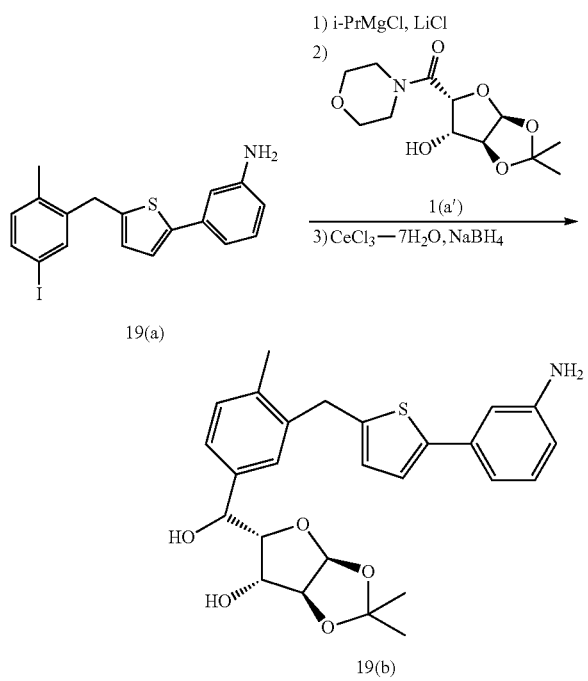

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 19(a) (3.8 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated NH$_4$Cl solution. The aqueous phase was removed and extracted with ethyl acetate. The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). CeCl$_3$.7H$_2$O (490 mg, 1.32 mmol) was added at room temperature. The mixture was stirred for 20 mins until it completely dissolved, and cooled to −78° C. NaBH$_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous Na$_2$SO$_4$, and concentrated to produce a crude pale yellow oily product 19(b).

2) Synthesis of Compound 19(c)

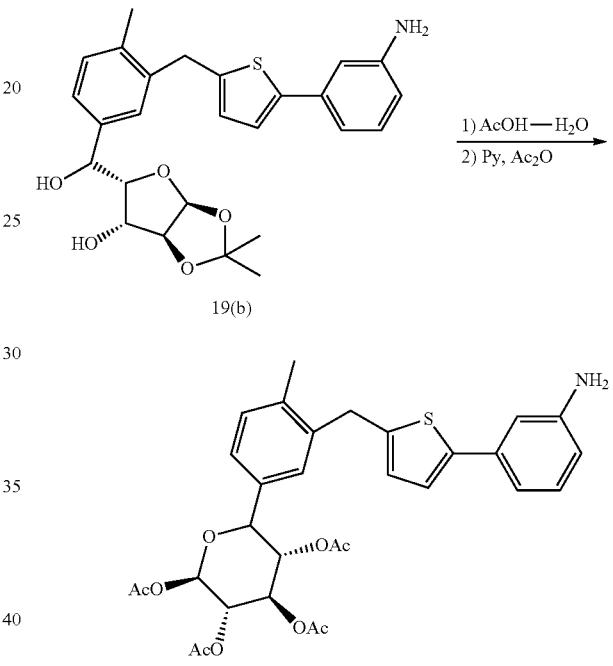

The crude Compound 19(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 19(c) (504 mg, 77%).

3) Synthesis of Compound 19(e)

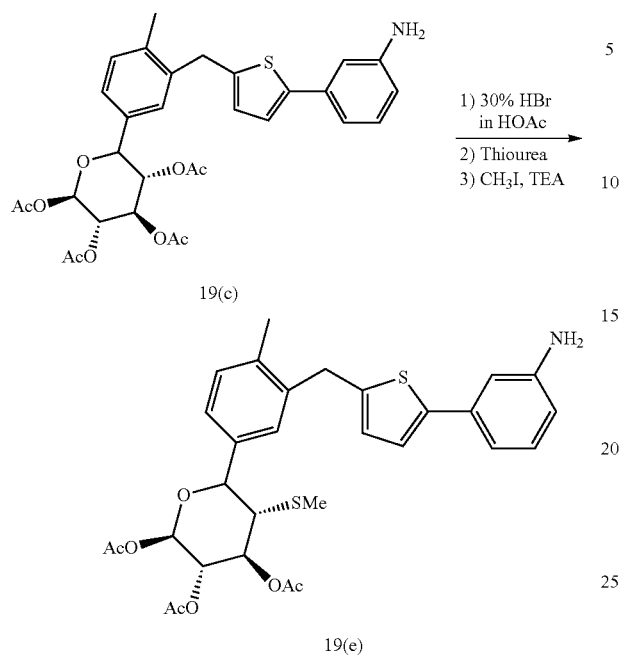

19(c)

19(e)

Under an ice-water bath, to a single-neck bottle containing Compound 19(c) (403 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous $NaHCO_3$ solution. The organic phase was separated. The aqueous phase was extracted with dichloromethane (3×10 mL). The organic phases were combined, washed with water and a saturated aqueous NaCl solution successively, dried with anhydrous $Na_2SO_4$, and concentrated to produce a pale yellow liquid.

At room temperature, to the above resulting pale yellow liquid, 8 mL MeCN and 154 mg $S(NH_2)_2$ were added. The mixture was heated under reflux for 1 hr, and then cooled to room temperature. $Et_3N$ (4 eq) and $CH_3I$ (3 eq) were added. The mixture was stirred for 1 hr. The reaction was quenched with a saturated aqueous $NaHCO_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous $Na_2SO_4$, and concentrated. The resulting residue was purified by a silica gel column chromatography (petroleum ether/ethyl acetate=5:1) to produce a pale yellow solid 19(e) (268 mg, 68% (three steps)).

$^1$H NMR (400 Hz, $CDCl_3$) δ1.78 (s, 3H), 2.03 (s, 3H), 2.12 (s, 3H), 2.19 (s, 3H), 2.32 (s, 3H), 4.11 (d, J=3.2 Hz, 2H), 4.43 (d, J=9.6 Hz, 1H), 4.54 (d, J=9.6 Hz, 1H), 5.14 (t, J=9.8 Hz, 1H), 5.24 (t, J=9.6 Hz, 1H), 5.34 (t, J=9.2 Hz, 1H), 6.58-6.63 (m, 2H), 6.87-6.88 (m, 1H), 6.96 (d, J=7.6 Hz, 1H), 7.09 (d, J=3.6 Hz, 1H), 7.12-7.20 (m, 4H).

4) Synthesis of Compound 19

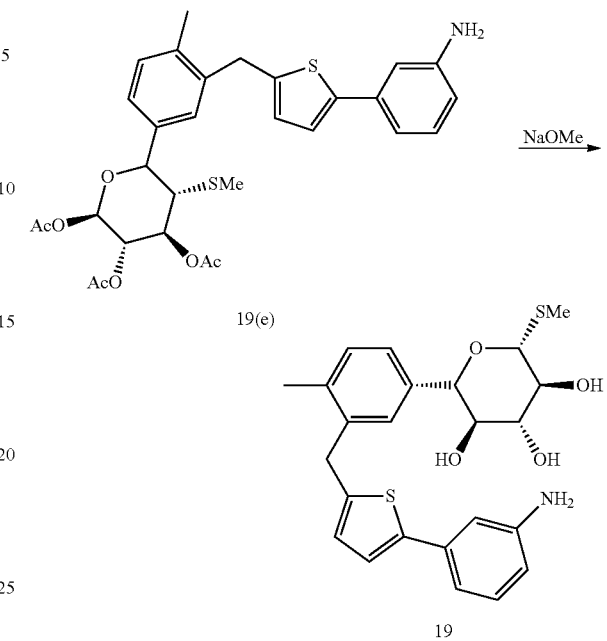

19(e)

19

Compound 19(e) (242 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 19 (167 mg, 88%).

$^1$H NMR (400 Hz, $CDCl_3$) δ2.19 (s, 3H), 2.32 (s, 3H), 3.68-3.72 (m, 1H), 3.68-3.72 (m, 1H), 3.91-3.96 (m, 1H), 4.17 (s, 2H), 4.43 (d, J=9.4 Hz, 1H), 4.90 (m, 1H), 6.58-6.63 (m, 2H), 6.87-6.90 (m, 1H), 6.96 (d, J=7.6 Hz, 1H), 7.09 (d, J=3.6 Hz, 1H), 7.12-7.20 (m, 4H).

ESI(+)m/z: 458.2

Example 20

Synthesis of (2S,3R,4R,5S,6R)-2-[3-((5-(4-fluorophenyl)thienyl)-2-methylene)-2-methoxy-4-methylphenyl)-6-methylthio-tetrahydropyran-3,4,5-triol

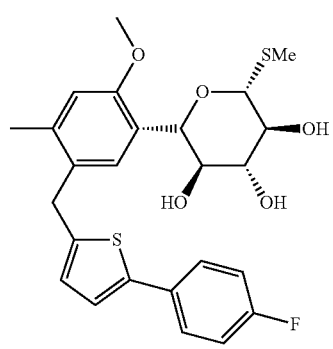

20

1) Synthesis of Compound 20(b)

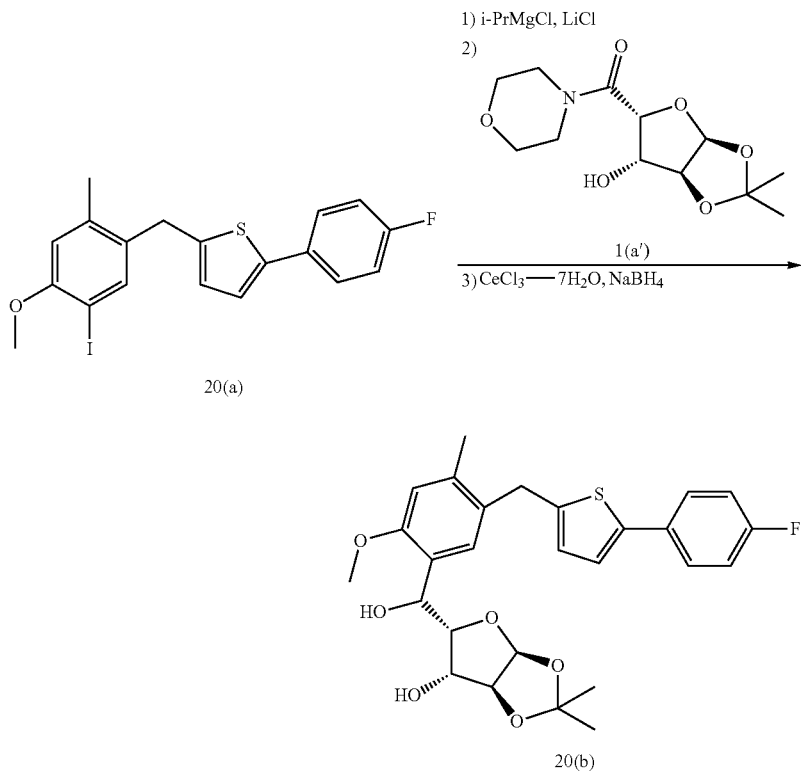

To a single-neck bottle containing LiCl (1.0 g, 23.66 mmol), THF (10 mL) was added, and then 2 mol/L i-PrMgCl/tetrahydrofuran solution (23.66 mmol, 11.83 mL) was added slowly. After the completion of the dropwise addition, the mixture was stirred at room temperature for 2 hrs. Then this reaction system was placed in an ice-water bath, and diluted with THF (10 mL). To the reaction system, 20(a) (4.1 g, 9.46 mmol) was added in batch. Then the reaction system was kept at this temperature and stirred for 1 hr. Then to the reaction system, the solid 1(a') (2.3 g, 8.5 mmol) was added. The stirring was continued for 1 hr. Then the reaction was quenched with a saturated $NH_4Cl$ solution. The aqueous phase was removed and extracted with ethyl acetate. The organic phases were combined, washed with water and a saturated aqueous NaCl solution successively, dried with anhydrous $Na_2SO_4$ and concentrated. The resulting residue was purified by a silica gel column chromatography (petroleum ether/ethyl acetate=2:1) to produce a pale yellow solid (2.1 g). This compound (535 mg, 1.1 mmol) was dissolved in methanol (9 mL). $CeCl_3 \cdot 7H_2O$ (490 mg, 1.32 mmol) was added at room temperature. The mixture was stirred for 20 mins until it completely dissolved, and cooled to −78° C. $NaBH_4$ (50 mg, 1.32 mmol) was added in batch. One hour later, the starting material consumed completely. Water (5 mL) was added to quench the reaction. The reaction system was warmed to room temperature and subjected to the rotary-evaporation to remove the solvent. The resulting aqueous phase was extracted with dichloromethane (3×10 mL). The organic phases were combined, washed with water and a saturated aqueous NaCl solution successively, dried with anhydrous $Na_2SO_4$, and concentrated to produce a crude pale yellow oily product 20(b).

2) Synthesis of Compound 20(c)

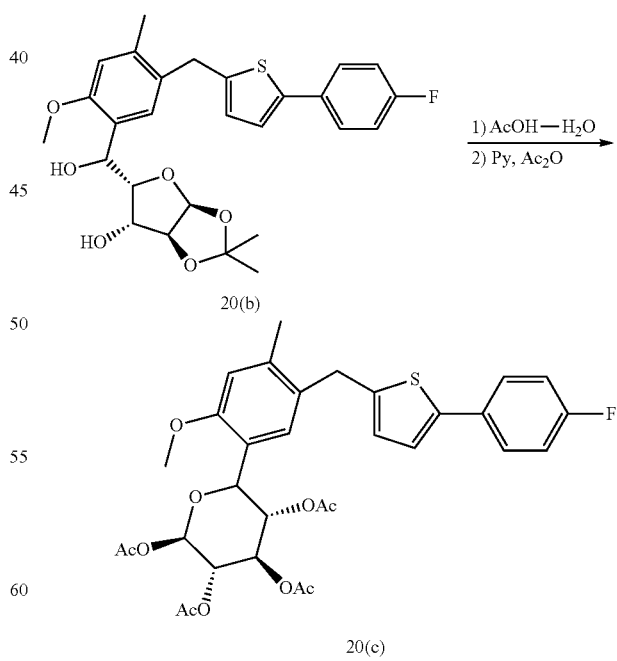

The crude Compound 20(b) was dissolved in acetic acid (12 mL) and water (8 mL). The mixture was heated at 100° C. for 15 hrs, cooled to room temperature, and rotary-evaporated to remove the solvent. Toluene was used to remove water from the reaction system to produce an oily solid.

The resulting solid was dissolved in dichloromethane (10 mL). Pyridine (1 mL) and Ac$_2$O (0.5 mL) were added slowly under an ice-water bath cooling. After the completion of the addition, the mixture was stirred at room temperature for 2 hrs. A saturated aqueous NaHCO$_3$ solution was added to the reaction system to quench the reaction. The organic phase was separated. The aqueous phase was extracted with dichloromethane (3×5 mL).

The organic phases were combined, washed with water and a saturated aqueous NaCl solution successively, dried with anhydrous Na$_2$SO$_4$, and concentrated. The resulting residue was separated by a silica gel column chromatography (petroleum ether/ethyl acetate=2:1) to produce a pale yellow solid 20(c) (512 mg, 74%).

3) Synthesis of Compound 20(e)

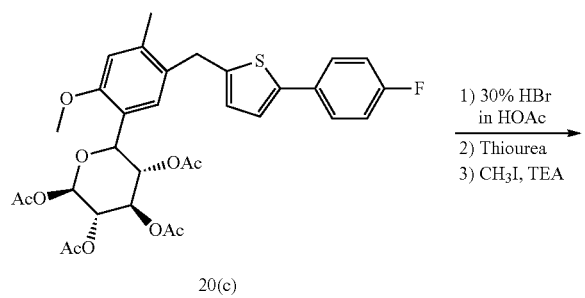

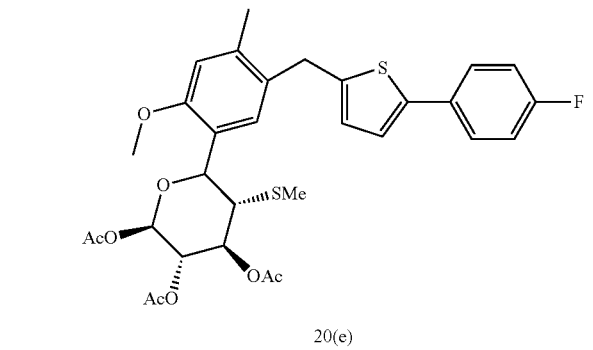

Under an ice-water bath, to a single-neck bottle containing Compound 20(c) (425 mg, 0.676 mmol), 30% HBr/HOAc solution (3 mL) was added. After the completion of the dropwise addition, the mixture was stirred at room temperature for 1 hr. Then dichloromethane (5 mL) was added to dilute the mixture. After stirring for 0.5 hr, more dichloromethane was added. The reaction was quenched with a saturated aqueous NaHCO$_3$ solution. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated to produce a pale yellow liquid.

At room temperature, to the above resulting pale yellow liquid, 8 mL MeCN and 154 mg S(NH$_2$)$_2$ were added. The mixture was heated under reflux for 1 hr, and then cooled to room temperature. Et$_3$N (4 eq) and CH$_3$I (3 eq) were added. The mixture was stirred for 1 hr. The reaction was quenched with a saturated aqueous NaHCO$_3$ solution and subjected to the rotary-evaporation to remove the organic solvent. Dichloromethane (10 mL) was added. The organic phase was separated. The aqueous phase was extracted with dichloromethane (3×10 mL). The organic phases were combined, washed with water and a saturated aqueous NaCl solution successively, dried with anhydrous Na$_2$SO$_4$, and concentrated. The resulting residue was purified by a silica gel column chromatography (petroleum ether/ethyl acetate=5:1) to produce a pale yellow solid 20(e) (254 mg, 61% (three steps)).

$^1$H NMR (400 Hz, CDCl$_3$) δ1.80 (s, 3H), 2.05 (s, 3H), 2.12 (s, 3H), 2.18 (s, 3H), 2.30 (s, 3H), 3.82 (s, 3H), 4.14 (s, 2H), 4.38 (d, J=9.6 Hz, 1H), 4.92 (m, 1H), 5.27 (m, 1H), 5.34 (m, 2H), 6.78-6.85 (m, 1H), 6.92 (s, 1H), 7.03-7.06 (m, 3H), 7.28 (s, 1H), 7.45-7.51 (m, 2H).

4) Synthesis of Compound 20

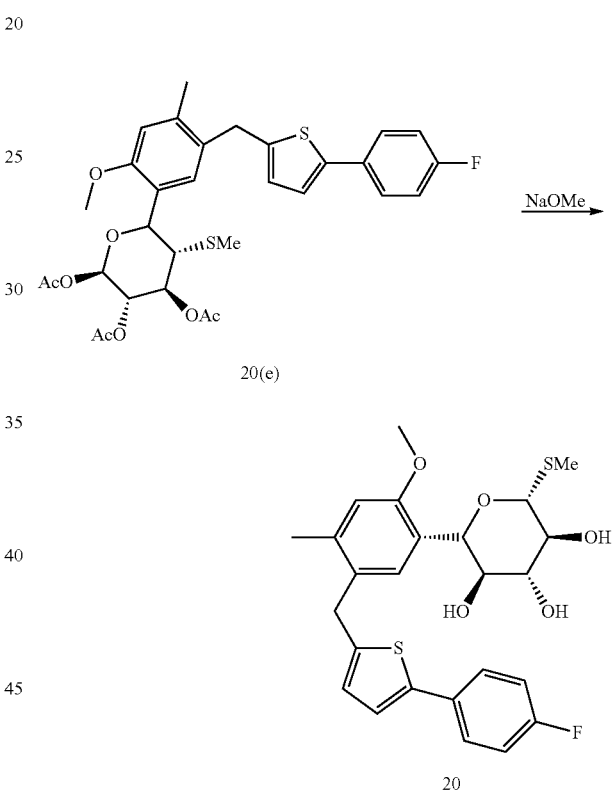

Compound 20(e) (255 mg, 0.414 mmol) was placed in a 50 mL single-neck bottle. After adding 15 mL methanol to form a suspension, sodium methoxide (50 mg, 0.455 mmol) was added. After the reaction liquid became clear, TLC indicated that the reaction was completed (1.5 hrs). Water was added dropwise until the white solid separated out. After filtering, the filtered caked was dried to produce Compound 20 (163 mg, 80%).

$^1$H NMR (400 Hz, CDCl$_3$) δ2.18 (s, 3H), 2.30 (s, 3H), 3.68-3.72 (m, 1H), 3.78-3.84 (m, 1H), 3.87 (s, 3H), 3.91-3.96 (m, 1H), 4.14 (s, 2H), 4.40 (d, J=9.6 Hz, 1H), 4.90 (m, 1H), 6.78-6.85 (s, 1H), 6.87 (s, 1H), 7.08-7.12 (m, 3H), 7.25 (s, 1H), 7.45-7.51 (m, 2H).

ESI(+)m/z: 491.1

Example 21

Synthesis of (2S,3R,4R,5S,6R)-2-[3-((5-(4-fluorophenyl)thienyl)-2-methylene)-4-chloro-phenyl)-6-methylsulfonyl-tetrahydropyran-3,4,5-triol

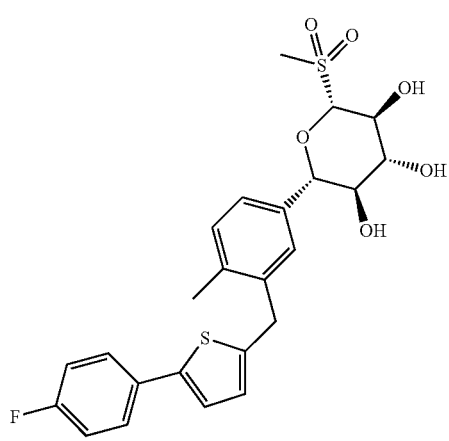

The title compound was prepared by the following steps:

1) Synthesis of Compound 21(a)

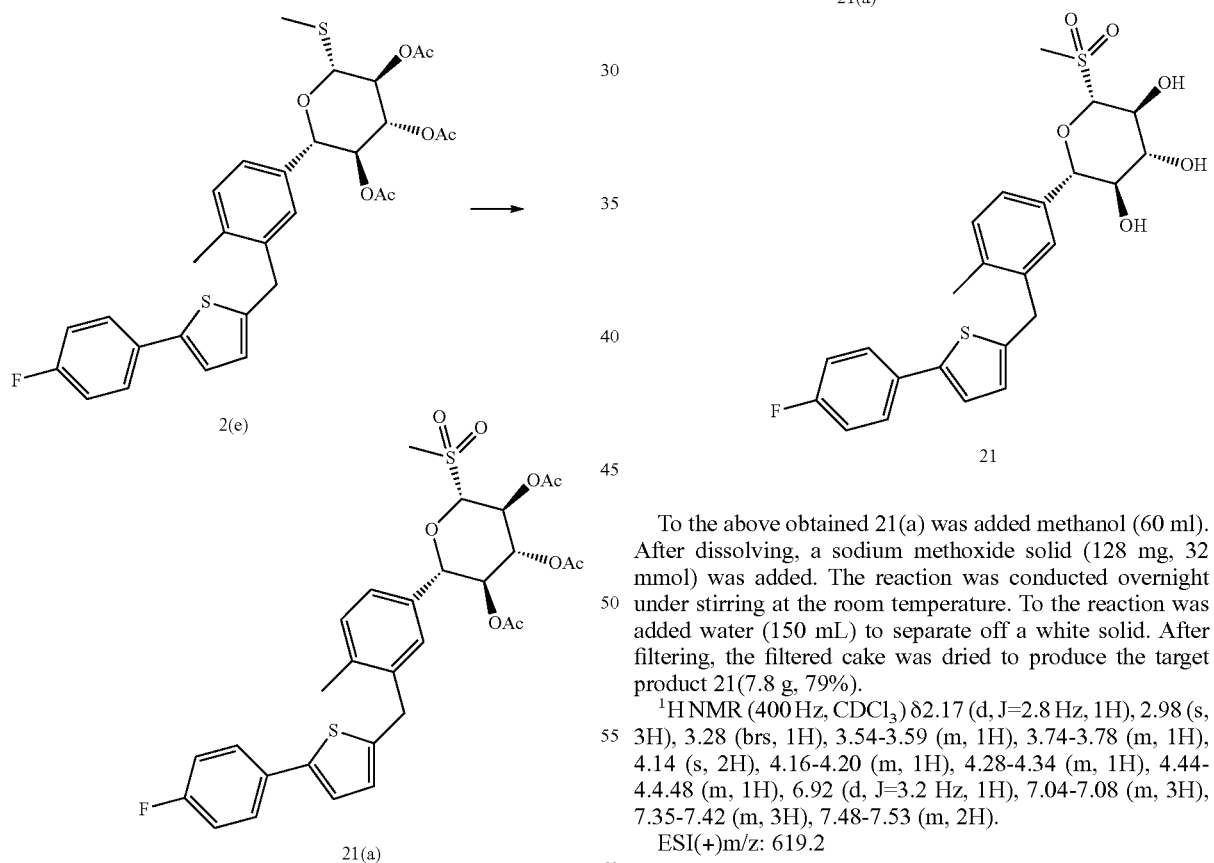

To a mixed solution of acetonitrile (72 ml) and methanol (18 ml) was added hydrogen peroxide-urea (9.223 g). The resulting mixture was stirred at room temperature until it became a clear solution. To this solution was added dropwise a solution of 2(e) (9.37 g, 0.016 mol) in acetonitrile (54 ml) at room temperature. After the completion of the dropwise addition, the reaction was conducted overnight under stirring at the room temperature. To the reaction was added ethyl acetate (90 mL). The reaction was washed with saturated $NaHCO_3$ (90 mL) and water (50 mL) successively, dried with $Na_2SO_4$, and concentrated to produce 21(a).

2) Synthesis of Compound 21

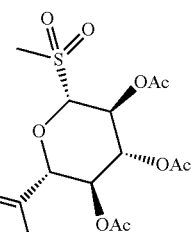

To the above obtained 21(a) was added methanol (60 ml). After dissolving, a sodium methoxide solid (128 mg, 32 mmol) was added. The reaction was conducted overnight under stirring at the room temperature. To the reaction was added water (150 mL) to separate off a white solid. After filtering, the filtered cake was dried to produce the target product 21(7.8 g, 79%).

$^1$H NMR (400 Hz, $CDCl_3$) δ2.17 (d, J=2.8 Hz, 1H), 2.98 (s, 3H), 3.28 (brs, 1H), 3.54-3.59 (m, 1H), 3.74-3.78 (m, 1H), 4.14 (s, 2H), 4.16-4.20 (m, 1H), 4.28-4.34 (m, 1H), 4.44-4.4.48 (m, 1H), 6.92 (d, J=3.2 Hz, 1H), 7.04-7.08 (m, 3H), 7.35-7.42 (m, 3H), 7.48-7.53 (m, 2H).

ESI(+)m/z: 619.2

II. Assays for the Activities of the Present Invention

Assay 1: Effect of the Present Compound on the Urine Glucose Excretion of the Normal Rat Method:

Thirty 7-week-old male SD rats (about 200 g) were used. The compound of Example 2 having a purity of 97.8% was chose as the present compound and formulated with 0.75%

CMC-Na. The positive control drug (SGLT-2 inhibitor, Dapagliflozin, synthesized according to Wei Meng et al., J. Med. Chem., Vol 51, 2008, pages 1145-1149) having a purity of 98% was formulated with 0.75% CMC-Na. The SD rats were acclimatized for 7 days, and then placed in the metabolic cages. The rats were fasted overnight (18 hr) under the free access to water. The basic urine samples were collected, and then thirty rats were weighed and grouped randomly into five groups, six rats per group. The grouping and the administration were shown in the following table.

| Group (n) | | Administration |
|---|---|---|
| Control group (6) | | 0.75% CMC-Na |
| Compound of Example 2 | low dosage (6) | 1 mg/kg |
| | medium dosage (6) | 10 mg/kg |
| | high dosage(6) | 20 mg/kg |
| Dapagliflozin | low dosage(6) | 1 mg/kg |
| | high dosage(6) | 10 mg/kg |

Fifteen minutes after the administration, the rats were intragastrically administrated with 50% glucose solution (2 g/kg). For ensuring a complete collection of the 24-hour urine, the rats were immediately placed in the metabolic cage after the administration of the tested compounds or the positive control drug. One hour after the administration of the glucose solution, the feeds were supplied to the rats. The urines after the administration of the tested compounds or the positive control drug were collected for 24 hours, and then the urine volumes were calculated and the urine glucose concentrations were detected.

The data were analyzed with the software SPSS 12.0, and the quantized data were expressed in "average±standard deviation". Multiple sets of data were compared according to the analysis of variance (One-way ANOVA). $P<0.05$ represented statistical difference.

In comparison with the blank control, after the single intragastric oral administrations of the compound of Example 2 or the SGLT-2 inhibitor Dapagliflozin to normal rats, the 24-hour urine volumes and the 24-hour urine glucose masses remarkably increased ($P<0.01$), and showed the dosage-dependencies. The urine volume and the excreted urine glucose mass in each of groups were respectively shown in Tables 1 and 2.

The results of the assays showed that the present compound of example 2 could promote the urine glucose excretion.

Assay 2: The Inhibitory Effect of the Present Invention on Human SGLT-2

0.2% gelatin was plated on a 24-well plate, and the plate was kept overnight. The plate was washed with PBS once before use. The NIH3T3 cells expressing human SGLT-2 by transfection were inoculated into the 24-well plate in 100,000 cells per well and 1 mL culture medium per well. On the third day, the culture medium was changed once, and simultaneously sodium butyrate was added thereto with a final concentration of 2 mM. The cells were washed with KRH-Na$^+$ (500 μL) twice, and then incubated with KRH-Na$^+$ (500 μL) for 30 minutes. The cells were then treated with 200 μL of KRH-Na$^+$ containing the compound of Example 2, and 50 μL of an uptake buffer (KRH-Na$^+$ plus methyl-a-D-[U-14C] glucopyranoside and 1 mM methyl-a-D-glucopyranoside). The cells were washed with 500 μL wash buffer thrice with the operation on ice, and baked overnight. The cells were lysed with 200 μL of 0.25N NaOH at 4° C. for 1 hr. The lysate was removed into an EPPENDORF tube, and centrifuged at 4° C. under 12000 g for 5 mins. 1504 of supernatant was placed in a 2 mL EPPENDORF tube, and 1.7 mL of scintillation cocktail was added thereto. The mixture was shaked vigorously, and then counted. The inhibition rate of the compound of Example 2 at each of concentrations on the transporting activity was calculated.

$IC_{50}$ value could be determined by nonlinear curve fitting of sample activities vs. sample concentrations. The fitting calculation was done with the software Graphpad Prism 4, and the model used in the fitting was the sigmoidal dose-response (variable slope).

Result: The compound of Example 2 had an $IC_{50}$ value for inhibiting the human SGLT-2 of 0.172 nM.

Assay 3: The Inhibitory Effect of the Present Invention on Human SGLT-1

0.2% gelatin was plated on a 24-well plate, and the plate was kept overnight. The plate was washed with PBS once before use. The NIH3T3 cells expressing human SGLT-1 by transfection were inoculated into the 24-well plate in 100,000 cells per well and 1 mL culture medium per well. On the third day, the culture medium was changed once, and simultaneously sodium butyrate was added thereto with a final concentration of 2 mM. The cells were washed with KRH-Na$^+$ (500 μL) twice, and then incubated with KRH-Na$^+$ (500 μL) for 30 minutes. The cells were then treated with 200 μL of KRH-Na$^+$ containing the compound of Example 2, and 50 μL of an uptake buffer (KRH-Na$^+$ plus methyl-a-D-[U-14C] glucopyranoside and 1 mM methyl-a-D-glucopyranoside). The cells were washed with 500 μL wash buffer thrice with the operation on ice, and baked overnight. The cells were lysed with 200 μL of 0.25N NaOH at 4° C. for 1 hr. The lysate was removed into an EPPENDORF tube, and centrifuged at 4° C. under 12000 g for 5 mins. 1504 of supernatant was placed in a 2 mL EPPENDORF tube, and 1.7 mL of scintillation cocktail was added thereto. The mixture was shaked vigorously, and then counted. The inhibition rate of the compound of Example 2 at each of concentrations on the transporting activity was calculated.

$IC_{50}$ value could be determined by nonlinear curve fitting of sample activities vs. sample concentrations. The fitting calculation was done with the software Graphpad Prism 4, and the model used in the fitting was the sigmoidal dose-response (variable slope).

Result: The compound of Example 2 had an $IC_{50}$ value for inhibiting the human SGLT-1 of 28.70 μM.

The results in the above assays 2 and 3 showed that the present compound had a strong inhibition effect on the human SGLT-2, while had a weak inhibition effect on the human SGLT-1; and therefore it would be a high selective SGLT-2 inhibitor.

While only selected embodiments have been chosen to illustrate the present invention, it will be apparent to those skilled in the art from this disclosure that various change and modification can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

The invention claimed is:

1. A compound represented by the following general formula (I):

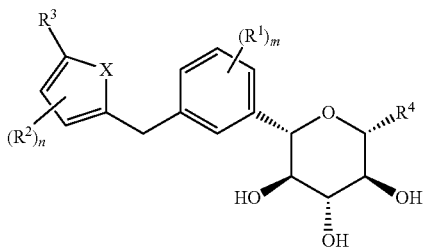

(I)

wherein:

X is O or S;

each of R¹ and R² is independently hydrogen, —OH, —SH, —NH₂, —NO₂, —CN, —COH, —COOH, —CONH₂, halogen, $C_1$-$C_4$alkyl, —O—$C_1$-$C_4$alkyl, —S—$C_1$-$C_4$alkyl, —SO—$C_1$-$C_4$alkyl, —SO₂—$C_1$-$C_4$alkyl, —CO—$C_1$-$C_4$alkyl, —CO₂—$C_1$-$C_4$alkyl, —CONH—$C_1$-$C_4$alkyl, —C≡C—$C_1$-$C_4$alkyl, —NHSO₂—$C_1$-$C_4$alkyl, —NHCO—$C_1$-$C_4$alkyl or —$C_3$-$C_6$cycloalkyl;

R³ is hydrogen, —OH, —SH, —NH₂, —NO₂, —CN, —COH, —COOH, —CONH₂, halogen, —$C_1$-$C_4$alkyl, —O—$C_1$-$C_4$alkyl, —S—$C_1$-$C_4$alkyl, —CO—$C_1$-$C_4$alkyl, —CO₂—$C_1$-$C_4$alkyl, —CONH—$C_1$-$C_4$alkyl, an aryl having 1-3 substituents selected from the groups in Group A, a heteroaryl having 1-3 substituents selected from the groups in Group A, a C3-C8cycloalkyl having 1-3 substituents selected from the groups in Group A, a nitrogen-containing saturated heterocyclic group having 1-3 substituents selected from the groups in Group A or a nitrogen-containing partially unsaturated heterocyclic group having 1-3 substituents selected from the groups in Group A, wherein, the group in Group A is selected from the group consisting of: hydrogen, halogen, —OH, —SH, —NH₂, —NO₂, —CN, —COH, —COOH, —CONH₂, $C_1$-$C_4$alkyl, —O—$C_1$-$C_4$alkyl, —NH—$C_1$-$C_4$alkyl, —S—$C_1$-$C_4$alkyl, —SO₂—$C_1$-$C_4$alkyl, —CO—$C_1$-$C_4$alkyl, —CO₂—$C_1$-$C_4$alkyl, —CONH—$C_1$-$C_4$alkyl, —CONH—$C_3$-$C_6$cycloalkyl, —$C_1$-$C_4$alkyl-OH, -aryl, —O-aryl, —NH-aryl, —S-aryl, —SO₂-aryl, —CO-aryl, —CO₂-aryl, —CONH-aryl, -cycloalkyl, -heteroaryl, -a nitrogen-containing saturated heterocyclic group, —$C_1$-$C_4$alkyl-a nitrogen-containing saturated heterocyclic group and -a nitrogen-containing partially unsaturated heterocyclic group;

R⁴ is —O—R⁵, —S—R⁵, —SO—R⁵, —SO₂—R⁵, R⁵ is —$C_1$-$C_4$alkyl or —$C_3$-$C_8$cycloalkyl;

m is 1, 2 or 3; and n is 1 or 2, or a pharmaceutically acceptable salt thereof.

2. The compound of claim 1, or a pharmaceutically acceptable salt thereof, wherein said X is S, R⁴ is —S—CH₃ or —SO₂—CH₃.

3. The compound of claim 1, or a pharmaceutically acceptable salt thereof, wherein each of said R¹ and R² is independently hydrogen, —OH, —NH₂, —NO₂, —CN, —COOH, halogen, —$C_1$-$C_4$alkyl, —O—$C_1$-$C_4$alkyl or —$C_3$-$C_6$cycloalkyl, both m and n are 1.

4. The compound of claim 3, or a pharmaceutically acceptable salt thereof, wherein each of said R¹ and R² is independently hydrogen, halogen or —$C_1$-$C_4$alkyl.

5. The compound of claim 4, or a pharmaceutically acceptable salt thereof, wherein said R¹ is chloro or methyl, R² is hydrogen.

6. The compound of claim 1, or a pharmaceutically acceptable salt thereof, wherein R³ is halogen, an aryl having 1-3 substituents selected from the groups in Group A, a heteroaryl having 1-3 substituents selected from the groups in Group A, a nitrogen-containing saturated heterocyclic group having 1-3 substituents selected from the groups in Group A or a nitrogen-containing partially unsaturated heterocyclic group having 1-3 substituents selected from the groups in Group A, wherein, the group in Group A is selected from the group consisting of: hydrogen, halogen, —OH, —NH₂, —NO₂, —COH, —COOH, $C_1$-$C_4$alkyl, —O—$C_1$-$C_4$alkyl, —S—$C_1$-$C_4$alkyl, —CONH—$C_3$-$C_6$cycloalkyl, —$C_1$-$C_4$alkyl-OH and —$C_1$-$C_4$alkyl-a nitrogen-containing saturated heterocyclic group.

7. The compound of claim 6, or a pharmaceutically acceptable salt thereof, wherein said R³ is halogen.

8. The compound of claim 6, or a pharmaceutically acceptable salt thereof, wherein said R³ is a phenyl having 1-3 substituents selected from the groups in Group A, wherein, the group in Group A is selected from the group consisting of: hydrogen, halogen, —OH, —NH₂, —NO₂, —COH, —COOH, —$C_1$-$C_4$alkyl, —O—$C_1$-$C_4$alkyl, —S—$C_1$-$C_4$alkyl, —CONH—$C_3$-$C_6$cycloalkyl, —$C_1$-$C_4$alkyl-OH and —$C_1$-$C_4$alkyl-a nitrogen-containing saturated heterocyclic group.

9. The compound of claim 6, or a pharmaceutically acceptable salt thereof, wherein said R³ is a pyridyl having 1-3 substituents selected from the groups in Group A, wherein, the group in Group A is selected from the group consisting of: hydrogen, halogen, —OH, —NH₂, —NO₂, —COH, —COOH, —$C_1$-$C_4$alkyl, —O—$C_1$-$C_4$alkyl, —S—$C_1$-$C_4$alkyl, —CONH—$C_3$-$C_6$cycloalkyl, —$C_1$-$C_4$alkyl-OH and —$C_1$-$C_4$alkyl-a nitrogen-containing saturated heterocyclic group.

10. The compound of claim 1, selected from the group of the following compounds:

(2S,3R,4R,5S,6R)-2-[3-((5-(4-fluorophenyl)thienyl)-2-methylene)-4-chloro-phenyl)-6-methylthio-tetrahydropyran-3,4,5-triol;

(2S,3R,4R,5S,6R)-2-[3-((5-(4-fluorophenyl)thienyl)-2-methylene)-4-methylphenyl)-6-methylthio-tetrahydropyran-3,4,5-triol;

(2S,3R,4R,5S,6R)-2-[3-((5-(4-fluoropyridyl)thienyl)-2-methylene)-4-chloro-phenyl)-6-methylthio-tetrahydropyran-3,4,5-triol;

(2S,3R,4R,5S,6R)-2-[3-((5-(4-chloro)thienyl)-2-methylene)-4-chloro-phenyl)-6-methylthio-tetrahydropyran-3,4,5-triol, (2S,3R,4R,5S,6R)-2-[3-((5-(4-bromo)thienyl)-2-methylene)-4-methyl-phenyl)-6-methylthio-tetrahydropyran-3,4,5-triol;

(2S,3R,4R,5S,6R)-2-[3-((5-(3,4,5-trifluorophenyl)thienyl)-2-methylene)-4-methylphenyl)-6-methylthio-tetrahydropyran-3,4,5-triol;

(2S,3R,4R,5S,6R)-2-[3-((5-(3,4-difluorophenyl)thienyl)-2-methylene)-4-methylphenyl)-6-methylthio-tetrahydropyran-3,4,5-triol;

(2S,3R,4R,5S,6R)-2-[3-((5-(4-methoxyphenyl)thienyl)-2-methylene)-4-methylphenyl)-6-methylthio-tetrahydropyran-3,4,5-triol;

(2S,3R,4R,5S,6R)-2-[3-((5-(3-cynaophenyl)thienyl)-2-methylene)-4-methylphenyl)-6-methylthio-tetrahydropyran-3,4,5-triol;

(2S,3R,4R,5S,6R)-2-[3-((5-(2-formylphenyl)thienyl)-2-methylene)-4-methylphenyl)-6-methylthio-tetrahydropyran-3,4,5-triol;

(2S,3R,4R,5S,6R)-2-[3-((5-(3-formylphenyl)thienyl)-2-methylene)-4-methylphenyl)-6-methylthio-tetrahydropyran-3,4,5-triol;

(2S,3R,4R,5S,6R)-2-[3-((5-((4-methylpiperazin-1-yl)methyl)phenyl)thienyl)-2-methylene)-4-methylphenyl)-6-methylthio-tetrahydropyran-3,4,5-triol;

(2S,3R,4R,5S,6R)-2-[3-((5-3-(morpholinylmethyl)phenyl)thienyl)-2-methylene)-4-methylphenyl)-6-methylthio-tetrahydropyran-3,4,5-triol;

(2S,3R,4R,5S,6R)-2-[3-((5-(4-carboxylphenyl)thienyl)-2-methylene)-4-methylphenyl)-6-methylthio-tetrahydropyran-3,4,5-triol;

(2S,3R,4R,5S,6R)-2-[3-((5-(4-N-cyclopropylbenzamide)thienyl)-2-methylene)-4-methylphenyl)-6-methylthio-tetrahydropyran-3,4,5-triol;

(2S,3R,4R,5S,6R)-2-[3-((5-(4-methylthiophenyl)thienyl)-2-methylene)-4-methylphenyl)-6-methylthio-tetrahydropyran-3,4,5-triol;

(2S,3R,4R,5S,6R)-2-[3-((5-(2-furyl)thienyl)-2-methylene)-4-methylphenyl)-6-methylthio-tetrahydropyran-3,4,5-triol;

(2S,3R,4R,5S,6R)-2-[3-((5-(4-hydroxymethylphenyl)thienyl)-2-methylene)-4-methylphenyl)-6-methylthio-tetrahydropyran-3,4,5-triol;

(2S,3R,4R,5S,6R)-2-[3-((5-(3-aminophenyl)thienyl)-2-methylene)-4-methylphenyl)-6-methylthio-tetrahydropyran-3,4,5-triol;

(2S,3R,4R,5S,6R)-2-[3-((5-(4-fluorophenyl)thienyl)-2-methylene)-2-methoxy-4-methylphenyl)-6-methylthio-tetrahydropyran-3,4,5-triol; and (2S,3R,4R,5S,6R)-2-[3-((5-(4-fluorophenyl)thienyl)-2-methylene)-4-chloro-phenyl)-6-methylsulfonyl-tetrahydropyran-3,4,5-triol, or a pharmaceutically acceptable salt thereof.

11. The compound of claim 1, or a pharmaceutically acceptable salt thereof, wherein each of $R^1$ and $R^2$ is independently selected from —OH, —SH, —$NH_2$, —$NO_2$, —CN, —COH, —COOH, —$CONH_2$, halogen, $C_1$-$C_4$alkyl, —O—$C_1$-$C_4$alkyl, —S—$C_1$-$C_4$alkyl, —SO—$C_1$-$C_4$alkyl, —$SO_2$—$C_1$-$C_4$alkyl, —CO—$C_1$-$C_4$alkyl, —$CO_2$—$C_1$-$C_4$alkyl, —CONH—$C_1$-$C_4$alkyl, —C≡C—$C_1$-$C_4$alkyl, —$NHSO_2$—$C_1$-$C_4$alkyl, —NHCO—$C_1$-$C_4$alkyl, and —$C_3$-$C_6$cycloalkyl.

12. A pharmaceutical composition, which contains the compound according to claim 1 or a pharmaceutically acceptable salt thereof and a pharmaceutically acceptable carrier.

13. A process for preparing the compound of general formula (I) according to claim 1, which comprises the steps of:

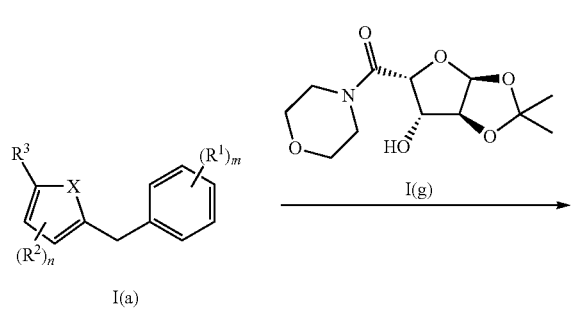

I(a)

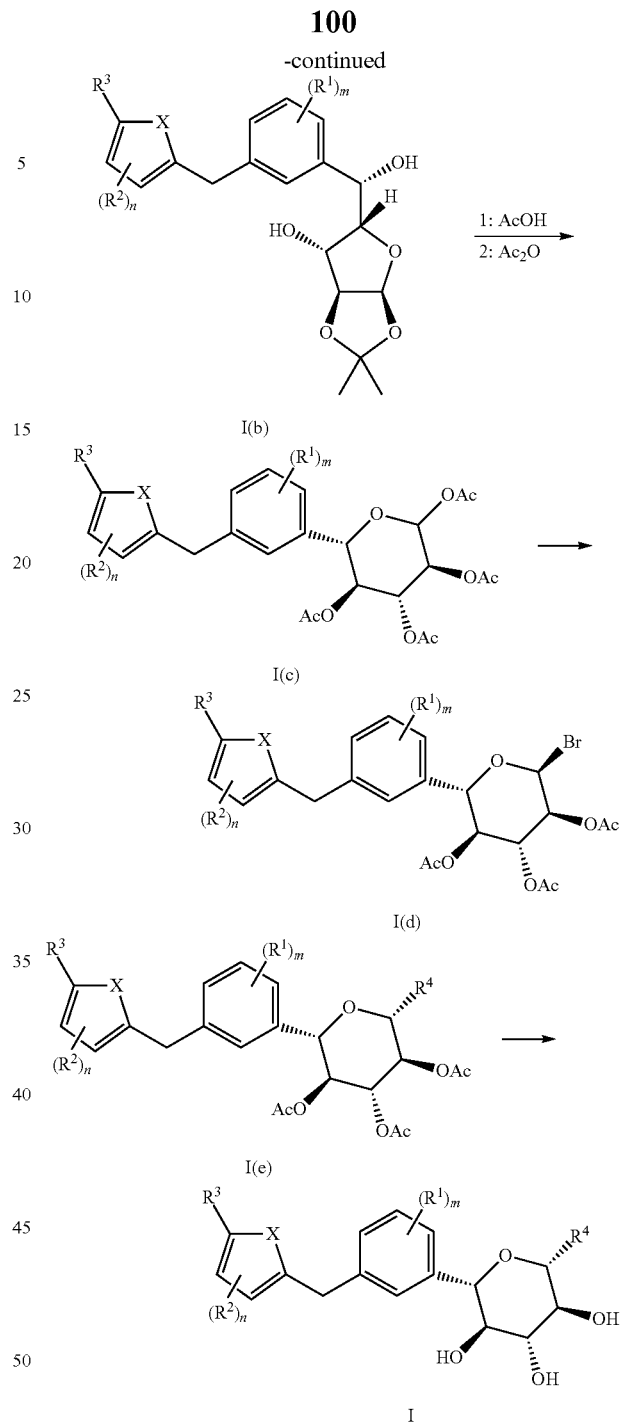

herein, X, $R^1$, $R^2$, $R^3$, $R^4$, m and n are defined as claim 1, (3aS,5R,6S,6aS)-[6-hydroxy-2,2-dimethyl-tetrahydrofuro[3,2-d][1,3]-dioxol-5-yl]-(morpholino)methanone I(g) is used as starting material, to which is added a halide of formula I(a), and then an alcohol I(b) is obtained; I(b) is treated with an alcohol and water in the presence of an acid, and acetylizad with acetic anhydride in the presence of an organic base to obtain a compound I(c); I(c) is added to an acetic acid solution containing bromide hydrogen to conduct the reaction to obtain a compound I(d), which is reacted with a nucleophilic reagent alkoxide, mercaptide or mercaptan without separation and purification to obtain a compound I(e)

directly (if $R^4$=—O—$R^5$, —S—$R^5$) or after the oxidation (if $R^4$=—SO—$R^5$ or —$SO_2$—$R^5$); and the acetyl of the saccharide moiety in the compound I(e) is hydrolyzed conventionally to obtain the target compound I.

14. A method for treating diabetes mellitus, the method comprising administering to a patient in need thereof a compound according to claim 1 or a pharmaceutically acceptable salt thereof.

* * * * *